US008237014B2

(12) United States Patent
Blaylock et al.

(10) Patent No.: US 8,237,014 B2
(45) Date of Patent: Aug. 7, 2012

(54) ENERGY CROPS FOR IMPROVED BIOFUEL FEEDSTOCKS

(75) Inventors: Michael J. Blaylock, Purcellville, VA (US); Bruce W. Ferguson, Great Falls, VA (US); David A. Lee, Washington, DC (US)

(73) Assignee: Edenspace Systems Corporation, Chantilly, VA (US)

( * ) Notice: Subject to any disclaimer, the term of this patent is extended or adjusted under 35 U.S.C. 154(b) by 1245 days.

(21) Appl. No.: 11/712,593

(22) Filed: Feb. 27, 2007

(65) Prior Publication Data

US 2007/0250961 A1    Oct. 25, 2007

Related U.S. Application Data

(60) Provisional application No. 60/777,191, filed on Feb. 27, 2006, provisional application No. 60/832,410, filed on Jul. 21, 2006.

(51) Int. Cl.
*C12N 15/82* (2006.01)
*C12N 15/10* (2006.01)
*C12N 15/00* (2006.01)

(52) U.S. Cl. ..... 800/278; 800/284; 800/288; 435/320.1; 435/440; 536/23.1; 536/23.7

(58) Field of Classification Search .......... None
See application file for complete search history.

(56) References Cited

U.S. PATENT DOCUMENTS

| | | | |
|---|---|---|---|
| 5,275,944 A | 1/1994 | Himmel et al. | 435/209 |
| 5,380,831 A | 1/1995 | Adang et al. | 536/23.71 |
| 5,436,391 A | 7/1995 | Fujimoto et al. | 800/292 |
| 5,563,055 A | 10/1996 | Townsend et al. | 800/294 |
| 5,591,616 A | 1/1997 | Hiei et al. | 435/469 |
| 5,625,136 A | 4/1997 | Koziel et al. | 800/302 |
| 5,670,356 A | 9/1997 | Sherf et al. | 435/189 |
| 5,693,518 A | 12/1997 | Kofod et al. | 435/200 |
| 5,874,304 A | 2/1999 | Zolotukhin et al. | 435/366 |
| 5,912,157 A | 6/1999 | von der Osten et al. | 435/209 |
| 6,127,160 A | 10/2000 | Yamanobe et al. | 435/209 |
| 6,197,564 B1 | 3/2001 | Kofod et al. | 435/200 |
| 6,323,023 B1 | 11/2001 | Shoseyov et al. | 435/320.1 |
| 6,441,272 B1 | 8/2002 | Ye | 800/298 |
| 6,455,762 B1* | 9/2002 | Chiang et al. | 800/298 |
| 6,580,230 B2 | 6/2003 | Hood et al. | 435/105 |
| 6,623,949 B1 | 9/2003 | Gualfetti et al. | 435/209 |
| 6,635,465 B1 | 10/2003 | Gualfetti et al. | 435/209 |
| 6,969,784 B2 | 11/2005 | Chiang et al. | 800/287 |
| 7,049,485 B2 | 5/2006 | Sticklen et al. | 800/288 |
| 7,102,057 B2 | 9/2006 | Lanahan et al. | 800/284 |
| 7,129,396 B2 | 10/2006 | Amasino et al. | 800/298 |
| 7,199,282 B2 | 4/2007 | Amasino et al. | 800/278 |
| 7,361,806 B2 | 4/2008 | Lebel | |
| 2003/0109011 A1 | 6/2003 | Hood et al. | 435/105 |
| 2004/0005674 A1 | 1/2004 | Duck et al. | 435/105 |
| 2004/0025203 A1* | 2/2004 | Singletary et al. | 800/284 |
| 2004/0098767 A1 | 5/2004 | Spangenberg et al. | 800/320 |
| 2005/0191736 A1* | 9/2005 | Brown et al. | 435/161 |
| 2005/0235379 A1 | 10/2005 | Luo et al. | 800/287 |
| 2006/0026715 A1 | 2/2006 | Hood et al. | 800/284 |
| 2006/0179513 A1 | 8/2006 | Sticklen et al. | 800/278 |
| 2006/0185036 A1 | 8/2006 | Sticklen et al. | 800/284 |
| 2006/0185037 A1 | 8/2006 | Sticklen et al. | 800/284 |
| 2006/0200877 A1 | 9/2006 | Lanahan et al. | 800/284 |
| 2008/0022425 A1 | 1/2008 | Lebel | |
| 2008/0078005 A1 | 3/2008 | Lebel | |
| 2009/0320831 A1 | 12/2009 | Lanahan et al. | |

FOREIGN PATENT DOCUMENTS

| | | |
|---|---|---|
| WO | WO 91/15588 | 10/1991 |
| WO | WO 94/14953 | 7/1994 |
| WO | WO 95/33837 | 12/1995 |
| WO | WO 96/00290 | 1/1996 |
| WO | WO 97/08325 | 3/1997 |
| WO | WO 00/71670 | 11/2000 |
| WO | WO 01/98469 | 12/2001 |
| WO | WO 02/24926 | 3/2002 |
| WO | WO 02/33091 | 4/2002 |
| WO | WO 02/079400 | 10/2002 |
| WO | WO 02/095014 | 11/2002 |
| WO | WO-03/018766 | 3/2003 |
| WO | WO 2005/019462 | 3/2005 |

OTHER PUBLICATIONS

Apel et al., "Cloning and targeted gene disruption of XYL1, a b-1,4-xylanase gene from the maize pathogen *Cochliobolus carbonum*", *Mol. Plant Microbe Interact.*, 1993, 6: 467-473.

Barnett et al., "Cloning and amplification of the gene encoding an extracellular beta-glucosidase from *Trichoderma reesei*: evidence for improved rates of saccharification of cellulosic substrates", *BioTechnology*, 1991, 9: 562-567.

Beguin, "Detection of cellulase activity in polyacrylamide gels using Congo red-stained agar replicas", *Anal. Biochem.*, 1983, 131: 333-336.

Cai et al., "Production and distribution of endoglucanase, cellobiohydrolase, and beta-glucosidase components of the cellulolytic system of *Volvariella volvacea*, the edible straw mushroom", *Appl. Environ. Microbiol.*, 1999, 65: 553-559.

Campbell and Gowri, "Codon Usage in Higher Plants, Green Algae, and Cyanobacteria", *Plant Physiol.*, 1990, 92: 1-11.

Cazemier et al., "A beta-1,4-endoglucanase-encoding gene from *Cellulomonas pachnodae*", *Appl. Microbiol. Biotechnol.*, 1999, 52: 232-239.

Cazzonelli and Velten, "An in Vivo Luciferase-Based Transient Assay System Using Agrobacteria-Infiltration: Implications for Post-Transcriptional Gene Silencing", *Planta*, 2006, 224: 582-597.

(Continued)

*Primary Examiner* — Brent T Page
(74) *Attorney, Agent, or Firm* — Choate Hall & Stewart LLP

(57) ABSTRACT

The present invention is directed to improved systems and methods for reducing costs and increasing yields of cellulosic ethanol. In particular, the present invention provides plants genetically transformed for increased biomass, expression of lignocellulolytic enzymes, and simplification of harvesting and downstream processing. Also provided are methods for using these transgenic plants in the production of clean, marketable feedstocks for production of renewable fuels and chemicals and in other applications including phytoremediation.

73 Claims, 20 Drawing Sheets
(4 of 20 Drawing Sheet(s) Filed in Color)

OTHER PUBLICATIONS

Chen et al., "Nucleotide Sequence and Deduced Primary Structure of Cellobiohydrolase II from *Trichoderma reesei*", *BioTechnology*, 1987, 5: 274-278.

Chow et al., "The cel3 gene of *Agaricus bisporus* codes for a modular cellulase and is transcriptionally regulated by the carbon source", *Appl. Environ. Microbiol.*, 1994, 60: 2779-2785.

Cohen et al., "Processive Endoglucanase Active in Crystalline Cellulose Hydrolysis by the Brown Rot Basidiomycete *Gloeophyllum trabeum*", *Appl. Environ. Microbiol.*, 2005, 71: 2412-2417.

Conesa et al., "Fungal peroxidases: molecular aspects and applications", *J. Biotechnol.*, 2002, 93: 143-158.

Dai et al., "Improved plant-based production of E1 endoglucanase using potato: expression optimization and tissue targeting", *Mol. Breeding*, 2000, 6: 277-285.

Dai et al., "Expression of *Acidothermus cellulolyticus* endoglucanase E1 in transgenic tobacco: biochemical characteristics and physiological effects", *Transg. Res.*, 2000, 9: 43-54.

Dai et al., "Optimization of *Acidothermus cellulolyticus* endoglucanase (E1) production in transgenic tobacco plants by transcriptional, post-transcription and post-translational modification", *Transg. Res.*, 2005, 14: 627-543.

Davies et al., "Structure and function of *Humicola insolens* family 6 cellulases: structure of the endoglucanase, Cel6B, at 1.6 Å resolution", *Biochem. J.*, 2000, 348: 201-207.

de Boer et al., "Analysis of nucleotide sequences of two ligninase cDNAs from a white-rot filamentous fungus", *Gene*, 1987, 60: 93-102.

de Boer et al., "Corrigendum", *Gene*, 1988, 69: 369.

De Groot et al., "An endo-1,4-β-xylanase-encoding gene from *Agaricus bisporus* is regulated by compost-specific factors", *J. Mol. Biol.*, 1998, 277: 273-284.

Denman et al., "Characterization of a *Neocallimastix patriciarum* cellulase cDNA (celA) homologous to *Trichoderma reesei* cellobiohydrolase II", *Appl. Environ. Microbiol.*, 1996, 62: 1889-1896.

de Oliviera Azevedo and Radford, "Sequence of cbh-1 gene of Humicola grisea var. thermoidea", *Nucleic Acids Res.*, 1990, 18: 668.

Garavaglia et al., "The structure of *Rigidoporus lignosus* Laccase containing a full complement of copper ions, reveals an asymmetrical arrangement for the T3 copper pair", J. Mol. Biol., 2004, 342: 1519-1531.

Gielkens et al., "Two cellobiohydrolase-encoding genes from *Aspergillus niger* require D-xylose and the xylanolytic transcriptional activator XlnR for their expression", *Appl. Environ. Microbiol.*, 1999, 65: 4340-4345.

Goedegebuur et al., "Cloning and relational analysis of 15 novel fungal endoglucanases from family glycosyl hydrolase", *Curr. Genet.*, 2002, 41: 89-98.

Grootjen et al., "Effects of the aeration rate on the fermentation of glucose and xylose by *Pichia stipitis*", *Enzyme Microb. Technol.*, 1990, 12: 20-23.

Haas et al., "Cloning and structural organization of a xylanase-encoding gene from *Penicillium chrysogenum*", *Gene*, 1993, 126: 237-242.

Horsch et al., "A simple and general method for transferring genes into plants", *Science*, 1985, 227: 1229-1231.

Inagaki et al., "Gene cloning and characterization of an acidic xylanase from *Acidobacterium capsulatum*", *Biosci. Biotechnol. Biochem.*, 1998, 62: 1061-1067.

Iwashita et al., "The bglA gene of *Aspergillus kawachii* encodes both extracellular and cell wall-bound beta-glucosidases.", *Appl. Environ. Microbiol.*, 1999, 65: 5546-5553.

Jefferson et al., "GUS fusions: beta-glucuronidase as a sensitive and versatile gene fusion marker in higher plants", *EMBO J.*, 1987, 6: 3901-3907.

Kawaguchi et al., "Cloning and sequencing of the cDNA encoding beta-glucosidase 1 from *Aspergillus aculeatus*", *Gene*, 1996, 173: 287-288.

Kiiskinen et al., "Laccase from *Melanocarpus albomyces* binds effectively to cellulose", *FEBS Letters*, 2004, 576: 251-255.

Kitamoto et al., "Molecular cloning, purification and characterization of two endo-1,4-beta-glucanases from *Aspergillus oryzae* KBN616", *Appl. Microbiol. Biotechnol.*, 1996, 46: 538-544.

Kotter and Ciriacy, "Xylose fermentation by *Saccharomyces cerevisiae*", *Appl. Microbiol. Biotechnol.*, 1993, 38:776-783.

Kwon et al., "Heterologous expression and characterization of endoglucanase I (EGI) from *Trichoderma viride* HK-75.", *Biosci. Biotechnol. Biochem.*, 1999, 63: 1714-1720.

Levy and Dean, "The transition to flowering", *Plant Cell*, 1998, 10: 1973-1990.

Lockington et al., "Regulation by carbon and nitrogen sources of a family of cellulases in *Aspergillus nidulans*", *Fungal Genet. Biol.*, 2002, 37: 190-196.

Machida et al., "Nucleotide sequences of *Saccharomycopsis fibuligera* genes for extracellular beta-glucosidases as expressed in *Saccharomyces cerevisiae*", *Appl. Environ. Microbiol.*, 1988, 54: 3147-3155.

MacKay et al., "Structure of a *Bacillus subtilis* endo-beta-1,4-glucanase gene", *Nucleic Acids Res.*, 1986, 14: 9159-9170.

Meinke et al., "Cellobiohydrolase A (CbhA) from the cellulolytic bacterium *Cellulomonas fimi* is a beta-1,4-exocellobiohydrolase analogous to *Trichoderma reesei* CBH II", *Mol. Microbiol.*, 1994, 12: 413-422.

Michaels and Amasino, "Flowering Locus C encodes a novel MADS domain protein that acts as a repressor of flowering", *Plant Cell*, 1999, 11: 949-956.

Moriya et al., "Molecular cloning of endo-beta-D-1,4-glucanase genes, rce1, rce2, and rce3, from *Rhizopus oryzae*", *J. Bacteriol.*, 2003, 185: 1749-1756.

Murray et al., "Codon usage in plant genes", *Nucleic Acids Res.*, 1989, 17: 477-498.

Nagai et al., "Purification and characterization of an extracellular laccase from the edible mushroom *Lentinula edodes*, and decolorization of chemically different dyes", *Applied Microbiol. and Biotechnol.*, 2002, 60: 327-335.

Ng et al., "A homodimeric laccase with unique characteristics from the yellow mushroom *Cantharellus cibarius*", *Biochem. and Biophys. Res. Comm.*, 2004, 313: 37-41.

Penttila et al., "Homology between cellulase genes of *Trichoderma reesei*: complete nucleotide sequence of the endoglucanase I gene", *Gene*, 1986, 45: 253-263.

Saloheimo et al., "A novel, small endoglucanase gene, eg15, from *Trichoderma reesei* isolated by expression in yeast", *Mol. Microbiol.*, 1994, 13: 219-228.

Sanchez et al., "Growth and endoglucanase activity of *Acetivibrio cellulolyticus* grown in three different cellulosic substrates", *Revista de Microbiologica*, 1999, 30: 310-314.

Sheppard et al., "The use of conserved cellulase family-specific sequences to clone cellulase homologue cDNAs from *Fusarium oxysporum*", *Gene*, 1994, 150: 163-167.

Tadege et al., "Control of flowering time by FLC orthologues in *Brassica napus*", *The Plant Journal*, 2001, 28: 545-553.

Tadege et al., "Reciprocal control of flowering time by OsSOC1 in transgenic Arabidopsis and by FLC in transgenic rice.", *Plant Biotechnol. J.*, 2003, 1: 361-369.

Takashima et al., "Isolation of the gene and characterization of the enzymatic properties of a major exoglucanase of humicola grisea without a cellulose-binding domain", *J. Biochem.*, 1998, 124: 717-725.

Teather and P. Wood, "Use of Congo Red-Polysaccharide Interactions in Enumeration and Characterization of Cellulolytic Bacteria from the Bovine Rument", *App. & Env. Microbiology*, 1982, 43: 777-780.

Teeri et al., "The Molecular Cloning of the Major Cellulase gene from *Trichoderma reesei*", *Nature Biotechnology*, 1983, 696-699.

Teeri et al., "Homologous domains in *Trichoderma reesei* cellulolytic enzymes: gene sequence and expression of cellobiohydrolase II", *Gene*, 1987, 51: 43-52.

Tempelaars et al., "Isolation, characterization, and analysis of the expression of the cbhII gene of *Phanerochaete chrysosporium*", *Appl. Environ. Microbiol.*, 1994, 60: 4387-4393.

Toivola et al., "Alcoholic Fermentation of d-Xylose by Yeasts", *Appl. Environ. Microbiol.*, 1984, 47: 1221-1223.

Tucker et al., "Ultra-thermostable cellulases from Acidothermus cellulolyticus comparison of temperature optima with previously reported cellulases", *Biotechnology*, 1989, 7: 817-820.

Wada et al., "Codon usage tabulated from the GenBank genetic sequence data", *Nucl. Acids Res.*, 1990, 18: 2367.

Wong et al., "Characterization and structure of an endoglucanase gene cenA of *Cellulomonas fimi*", *Gene*, 1986, 44: 315-324.

Wong et al., "The cloning, expression and characterization of a cellobiase gene encoding a secretory enzyme from *Cellulomonas biazotea*", *Gene*, 1998, 207: 79-86.

Wood et al., "The genome sequence of *Schizosaccharomyces pombe*", *Nature*, 2002, 415: 871-880.

Wu et al., "Purification, cloning and characterization of two xylanases from *Magnaporthe grisea*, the rice blast fungus", *Mol. Plant Microbe Interact.*, 1995, 8: 506-514.

Zhang, "Characterization of a *Thermomonospora fusca* exocellulase", *Biochemistry*, 1995, 34: 3386-3395.

Ziegelhoffer et al., "Dramatic effects of truncation and sub-cellular targeting on the accumulation of recombinant microbial cellulase in tobacco", *Mol. Breeding*, 2001, 8: 147-158.

M. Ziegler et al., "Accumulation of a thermostable endo-1,4-D-glucanase in the apoplast of *Arabidopsis thaliana* leaves", *Molecular Breeding*, 2000, 6: 37-46.

\* cited by examiner

ENERGY CROPS FOR IMPROVED BIOFUEL FEEDSTOCKS

RELATED APPLICATIONS

The present application claims priority from Provisional Application U.S. Ser. No. 60/777,191 filed on Feb. 27, 2006 and Provisional Application U.S. Ser. No. 60/832,410 filed on Jul. 21, 2006. Each of the Provisional Applications, entitled "Energy Crops for Improved Biofuel Feedstocks", is incorporated herein by reference in its entirety.

GOVERNMENT SUPPORT

The work described herein was funded by the U.S. Department of Energy (Grant No. DE-FG02-04ER86183). The United States government may have certain rights in the invention.

BACKGROUND OF THE INVENTION

In 2004, U.S. ethanol production attained a record 3.35 billion gallons, up 19% from 2003 (S. Hillgren, "An ambitious energy goal", Farm J., January 2005, p. 58). While it is still a small part of the total U.S. fuel market, representing less than 4% of the more than 140 billion gallons of gasoline sold in 2006, the recent rapid increase in oil prices has increased its cost-competitiveness and indicates that it can continue to capture market share. Federal agencies such as the U.S. Department of Agriculture (USDA) have begun to implement programs of preferred procurement of biofuels such as ethanol as a fuel additive. The potential market for the technology—transportation fuel—is one of the largest in the U.S. economy.

The ability to produce ethanol from low-cost biomass has been called the "key" to making ethanol competitive as a gasoline additive (J. DiPardo, "Outlook for biomass ethanol production and demand", EIA Forecasts, 2002), with joint USDA/DOE studies forecasting the ability to produce up to 50 billion gallons of ethanol per year from U.S. farmland (A. McAloon et al., "Determining the cost of producing ethanol from corn starch and lignocellulosic feedstocks", 2000, NREL/TP-580-28893) and approximately 100 billion gallons per year from forestland and agricultural land combined (R. D. Perlack et al., "Biomass as feedstock for a bioenergy and bioproducts industry: The technical feasibility of a billion-ton annual supply", 2005, ORNL/TM-2005/66). Lignocellulosic production would also help to increase the net energy balance of corn ethanol, recently estimated at an energy output/input of 1.67 (H. Shapouri et al., "2001 net energy balance of corn-ethanol (preliminary report)", 2004, USDA, Office of the Chief Economist). The conversion of lignocellulosic feedstocks into ethanol has the advantages of the ready availability of large amounts of feedstock, the desirability of avoiding burning or land filling the materials, and the relatively easy conversion of glucose, produced by hydrolysis of cellulose, into ethanol. As a result, most studies show substantial energy advantages from the use of cellulosic feedstocks (e.g., Farrell et al., Science, 2006, 311: 506-508).

Today most fuel ethanol is produced from corn (maize) grain, which is milled, pretreated with heat and acid to break down lignin and cellulose, treated with amylase enzymes to hydrolyze starch to sugars, fermented, and distilled. The possibility of increasing energy yields by hydrolyzing the cellulose in corn stover or other plant biomass has been studied intensively over the last decade. While substantial progress has been made in reducing costs, two substantial challenges remain. The first is to reduce the costs of pre-treating the biomass to remove lignin and hemicellulose. New techniques, such as ammonia fiber explosion (AFEX) provide high yields, but still impose high capital and operating costs, and pretreatments in general create the need to dispose of large quantities of byproducts such as calcium sulfate. Second, the cost of microbially-produced cellulase enzymes today range from $0.30 to more than $1.00 per gallon of ethanol. While current research may eventually bring this cost down to a target of $0.10 per gallon, even lower costs are desirable to improve ethanol's cost competitiveness with fossil fuels.

Clearly, improved techniques are still needed to reduce the cost of biofuel feedstocks for ethanol production.

SUMMARY OF THE INVENTION

The present invention is directed to new approaches that address the current limitations of bioenergy production. In particular, the present invention relates to improved systems and strategies for reducing costs and increasing yields of cellulosic ethanol. More specifically, the invention generally involves genetically engineering plants for both increased biomass and expression of lignocellulolytic enzymes, an approach that results in downstream process innovations in ethanol production. In addition to producing clean, marketable feedstocks for bioenergy, the inventive approach can significantly improve the current state-of-the-art in contaminant recovery from phytoremediation crops, allowing treatment of contaminated biomass to reduce the costs and liabilities associated with landfill disposal, and enabling the recycling of recovered metals.

More specifically, in one aspect, the present invention provides a transgenic plant, the genome of which is augmented with a recombinant polynucleotide encoding at least one lignocellulolytic enzyme operably linked to a promoter sequence, wherein the polynucleotide is optimized for expression in the plant, wherein the at least one lignocellulolytic enzyme is produced at a level greater than 5% total soluble protein, greater than 10% total soluble protein or greater than 20% total soluble protein.

The at least one lignocellulolytic enzyme may be a cellulase, a hemicellulase, a ligninase or a combination thereof. In some embodiments, the lignocellulolytic enzyme exhibits low activity at a temperature below 30° C., below 50° C. or below 60° C. The lignocellulolytic enzyme may be expressed constitutively or tissue-specifically. For example, the lignocellulolytic enzyme may be expressed in a plant tissue selected from the group consisting of stems and leaves. The lignocellulolytic enzyme may be expressed in a targeted subcellular compartment or organelle, such as apoplast, chloroplast, cell wall, or vacuole.

The plant may be a monocotyledonous plant or a dicotyledonous plant. In certain embodiments, the plant is a crop plant. The plant may be selected from the group consisting of corn, switchgrass, sorghum, miscanthus, sugarcane, poplar, pine, wheat, rice, soy, cotton, barley, turf grass, tobacco, bamboo, rape, sugar beet, sunflower, willow, and eucalyptus.

In some embodiments, the genome of a transgenic plant of the invention is further augmented with a recombinant polynucleotide encoding at least one amylase enzyme operably linked to a promoter sequence, wherein the polynucleotide is optimized for expression in the plant. The amylase enzyme may be alpha-amylase enzyme or glucoamylase enzyme. In certain embodiments, the at least one amylase is produced at a level greater than 10% total soluble protein, greater than 25% total soluble protein or greater than 50% total soluble protein. The amylase may be expressed constitutively or tissue-specifically (for example, in stems and/or leaves). The amylase may be expressed in a targeted sub-cellular compartment or organelle (for example, apoplast, chloroplast, cell wall, and/or vacuole).

In some embodiments, the genome of a transgenic plant of the invention is further augmented with a recombinant polynucleotide encoding at least one protein with anti-microbial properties operatively linked to a promoter sequence, wherein the polynucleotide is optimized for expression in the plant. The protein may comprise an antibiotic. In certain embodiments, the at least one protein with anti-microbial properties is produced at a level greater than 0.1% total soluble protein, greater than 1% total soluble protein or greater than 10% total soluble protein. The bacterial protein may be expressed constitutively or tissue-specifically (for example, in seeds, stems and/or leaves). The anti-microbial protein may be expressed in a targeted sub-cellular compartment or organelle (for example, apoplast, chloroplast, cell wall, and/or vacuole). The anti-microbial protein may be effective against bacterial or fungal species that reduce ethanol yields during processing by producing substances that are toxic to the fermenting microbes or by consuming glucose and reducing glucose available for fermentation to ethanol.

In some embodiments, the genome of a transgenic plant of the present invention is further augmented with a recombinant polynucleotide encoding at least one enzyme for converting hard-to-ferment sugars to more easily fermentable sugars operably linked to a promoter sequence, wherein the polynucleotide is optimized for expression in the plant. The enzyme may be an isomerase that converts xylose to xylanose. In certain embodiments, the enzyme is produced at a level greater than 0.5% total soluble protein, greater than 5% total soluble protein, greater than 10% total soluble protein or greater than 20% total soluble protein.

The genome of a transgenic plant of the invention may also be further altered so as to minimize dispersal of the transgenes through plant production. For example, the genome of inventive transgenic plants may be altered so as to introduce male sterility or total sterility in the plant or to delay plant flowering.

The genome of a transgenic plant of the invention may also be further altered so as to reduce the amount of one or more forms of lignin in the transgenic plant relative to cellulose and hemicellulose, or so as to increase the amount of one or more forms of cellulose in the transgenic plant relative to lignin and hemicellulose, or so as to increase the amount of one or more forms of hemicellulose in the transgenic plant relative to lignin and cellulose.

In another aspect, the present invention provides a transgenic plant, the genome of which is augmented with a recombinant polynucleotide encoding at least one lignocellulolytic enzyme operably linked to a promoter sequence, wherein the polynucleotide is optimized for expression in the plant, and a recombinant polynucleotide that reduces expression of a flower promoter gene or that increases a flower repressor gene, operably linked to a promoter. In such transgenic plant, plant flowering is delayed and/or biomass production is enhanced.

In certain embodiments, the at least one lignocellulolytic enzyme is produced at a level greater than 0.5% total soluble protein, greater than 5% total soluble protein, greater than 10% total soluble protein or greater than 20% total soluble protein. The at least one lignocellulolytic enzyme may be a cellulase, a hemicellulase, a ligninase, and a combination thereof. As mentioned above, the at least one lignocellulolytic enzyme may be expressed constitutively or tissue-specifically; and/or may be expressed in a targeted sub-cellular compartment or organelle.

As mentioned above, the plant may be a monocotyledonous plant or a dicotyledonous plant. In certain embodiments, the plant is a crop plant. The plant may be selected from the group consisting of corn, switchgrass, sorghum, miscanthus, sugarcane, poplar, pine, wheat, rice, soy, cotton, barley, turf grass, tobacco, bamboo, rape, sugar beet, sunflower, willow, and eucalyptus.

In another aspect, the present invention provides a method for the cost-effective preparation of ethanol. The inventive method comprises steps of: treating a plant part comprising at least one lignocellulolytic enzyme under conditions to activate the at least one lignocellulolytic enzyme thereby degrading lignocellulose to form a hydrolysate mixture, wherein the plant part is obtained from an inventive transgenic plant; and incubating the hydrolysate mixture under conditions that promote conversion of fermentable sugars of the hydrolysate mixture to ethanol. In some embodiments, the plant part is substantially free of soil dirt.

In certain embodiments, prior to the treating step, the plant part is hot pretreated or is pretreated under conditions of less heat or less acid, or conditions that are otherwise less harsh or produce fewer toxic by-products than conditions used in pretreatment of biomass from non-transgenic plants. For example, the plant part may be pretreated by heating the plant part to a temperature greater than 50° C., greater than 75° C. or greater than 100° C. Additionally or alternatively, the plant part may be pretreated by adding water to decrease viscosity of the hydrolysate mixture. Additionally or alternatively, the plant part is pretreated by chopping, grinding, shredding or pulverizing the plant part.

In some embodiments, the method further comprises adding external lignocellulolytic enzymes to the plant part prior to the treating step. Such a method will result in increased ethanol production compared to a method in which the plant part is obtained from a non-transgenic plant.

In certain embodiments, the inventive method further comprises removing at least one unfermentable component from the hydrolysate mixture prior to the incubating (fermentation) step. Removing at least one unfermentable component may speed up conversion of fermentable sugars to ethanol. The at least one unfermentable component may be selected from the group consisting of lignin, lignin-breakdown products, phenols, furans, and combinations thereof. Removing at least one unfermentable component from the hydrolysate mixture may comprise separating/isolating and/or purifying the unfermentable component. In certain embodiments, after removal, the at least one unfermentable component, or a derivative thereof, is burned to produce heat or electricity. Heat thus produced may be used in the inventive method of ethanol production, for example, to heat the hydrolysate mixture and/or to distill ethanol.

In some embodiments, the inventive method further comprises a step of: distilling the ethanol produced by conversion of fermentable sugars of the hydrolysate mixture so as to obtain distilled ethanol. One or more unfermentable components removed from the hydrolysate mixture may be added to the distilled ethanol as denaturant. The one or more unfermentable components may be added to ethanol prior to the distilling step, distilled with the ethanol, and may remain in the distilled ethanol as a denaturant. Alternatively or additionally, one or more unfermentable components may be processed into compounds (e.g., methanol, butanol, or other alcohols) that can be used as denaturants.

In some embodiments, the inventive method further comprises a step of: distilling the ethanol produced by conversion of fermentable sugars of the hydrolysate mixture so as to obtain distilled ethanol, wherein the distilled ethanol comprises one or more unfermentable components that act as denaturants.

In certain embodiments, the process of producing ethanol from transgenic plant biomass further produces a by-product, such as dried distillers grain solids (DDGS), that has higher food value, such as increased levels of protein and oil, resulting from hydrolysis and removal of cellulose or, hemicellulose, or breakdown or removal of lignin, present in the by-product from non-transgenic plants.

In certain embodiments, the method further comprises adding microorganisms, such as microorganisms that ferment six-carbon sugars (e.g., glucose) or five-carbon sugars (e.g., xylose) or both, to the plant part so as to induce simultaneous saccharification and fermentation. Alternatively or additionally, the genome of transgenic plants used in the inventive method may be augmented with yeast genes or genes of other fermentation organisms to promote simultaneous saccharification and fermentation. In other embodiments, the microorganisms are added to the hydrolysate mixture prior to fermentation.

In certain embodiments, the inventive method is carried out using plant parts obtained from transgenic plants of the same or different species, containing the same or different enzymes. These plants are co-processed so as to combine the enzymes in the desired proportion to increase ethanol yield, such as by achieving more efficient hydrolysis of polysaccharides and breakdown and removal of lignin.

In other embodiments, the inventive method is carried out using plant parts obtained from transgenic plants and non-transgenic plants using common equipment and facilities for harvesting, ensilement, chopping, crushing, milling, liquefaction, saccharification, fermentation, distillation, drying, storage or transportation. For example, the plant parts may be corn grain and corn stover.

In certain embodiments, the inventive method further comprises a step of treating the plant part under conditions that promote starch hydrolysis. Treating the plant part under conditions that promote starch hydrolysis may comprise using at least one amylase enzyme, such as a glucoamylase, an α-amylase or a combination thereof. In some embodiments, the step of treating the plant part under conditions to activate the at least one lignocellulolytic enzyme and the step of treating the plant part under conditions to promote starch hydrolysis are performed simultaneously. In other embodiments, the step of treating the plant part under conditions to activate the at least one lignocellulolytic enzyme and the step of treating the plant part under conditions to promote starch hydrolysis are performed sequentially. Plant parts used in such methods may be obtained from two or more transgenic plants of the invention, and the transgenic plants may be of the same or different species and may produce the same or different lignocellulolytic enzyme. Alternatively, plant parts may be obtained from transgenic plants of the invention and non-transgenic plants. In certain embodiments, the plant part comprises one or more of corn grain, corn fiber and corn stover. The inventive method may be carried out using common equipment and facilities for harvesting, ensilement, chopping, crushing, milling, liquefaction, saccharification, fermentation, distillation, drying, storage or transportation. In certain embodiments, the inventive method is part of a dry milling process.

In another aspect, the present invention provides screening methods for the rapid identification of microbial cellulase enzymes that can function in plants. Such methods comprise the use of transiently transformed plant tissues (e.g., leaves) for assessing enzymatic activity of microbial cellulase enzymes.

In another aspect, the present invention provides methods to modify gene sequences for increased expression of microbial cellulases in plants. More specifically, the methods of the invention comprises steps of: providing a microbial polynucleotide gene sequence encoding one lignocellulolytic enzyme; averaging the codon usage of each of at least one first plant and one second plant to obtain a composite codon usage template; and modifying the microbial polynucleotide gene sequence using the codon usage template to generate a codon optimized polynucleotide encoding the lignocellulolytic enzyme, wherein the polynucleotide is optimized for expression in more than one plant. In certain embodiments, the polynucleotide is optimized for expression in two plants, three plants, four plants or more than four plants. In certain embodiments, at least one of the plants is monocot plant and at least one of the plants is a dicot plant. In certain embodiments, the polynucleotide is optimized for expression in a group of plants comprising maize, *arabidopsis*, and tobacco.

In another aspect, the present invention provides codon-optimized sequences for several microbial genes. In some embodiments, such sequences lead to increased transcription in plants. In some embodiments, such sequences are optimized for the expression in more than one plant. More specifically, the present invention provides an isolated codon optimized polynucleotide encoding E1 endoglucanase comprising the sequence of SEQ ID NO. 1; an isolated codon optimized polynucleotide encoding family 48 glycoside hydrolase comprising the sequence of SEQ ID NO. 2; and an isolated codon optimized polynucleotide encoding family 10 glycoside hydrolase comprising the sequence of SEQ ID NO. 3, wherein each polynucleotide is optimized for expression in more than one plant, i.e., in maize, *arabidopsis*, and tobacco. The invention further provides a plant cell, a plant part and a plant that is transformed using one of these codon optimized polynucleotides.

In yet another aspect, the present invention provides a method for contaminant recovery in phytoremediation. The inventive method comprises steps of: introducing, in a contaminated area, seeds from an inventive transgenic plant; growing transgenic plants from the seeds; harvesting grown transgenic plants; treating a plant part comprising at least one lignocellulolytic enzyme under conditions to activate the at least one lignocellulolytic enzyme thereby degrading lignocellulose to form a biomass and liberating contaminant sequestered inside the plant part, wherein the plant part is obtained from harvested grown transgenic plants; and recovering the contaminant liberated from the plant part. The method may further comprise disposing the biomass as a non-hazardous waste.

The contaminant may comprise a metalloid such as arsenic or selenium a heavy metal such as lead, chromium, cadmium, zinc, copper, or uranium, or a persistent organic pollutant such as DDT or PCBs.

In certain embodiments, prior to the treating step, the plant part is not pre-treated or is pre-treated under conditions of heat and acid that are less harsh than conditions used in pretreatment of biomass from non-transgenic plants.

These and other objects, advantages and features of the present invention will become apparent to those of ordinary skill in the art having read the following detailed description.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 8(A) shows a FLC transgenic plant exhibiting delay in flowering, larger leaf size and shorter, sturdier habit as compared to a control untransformed plant. FIG. 8(B) shows control untransformed plant anthers in complete maturity and pollen shed, and not yet mature anthers of FLC plants.

DEFINITIONS

Figure 1:
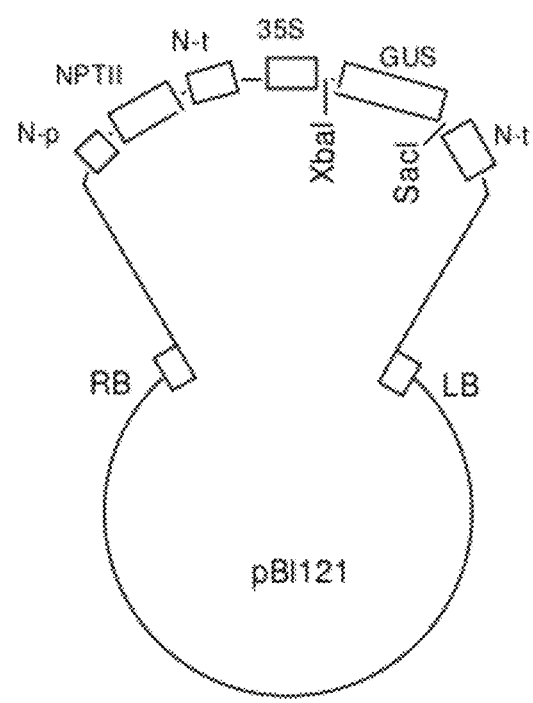
FIG. 1 is a map of the pBI121 vector used in the transformation of tobacco as reported in Example 1. The following sequences are abbreviated; NOS promoter (N-p), neomycin phospho-transferase II (NPTII), NOS terminator (N-t), cauliflower mosaic virus 35S promoter (35S), β-glucuronidase (GUS), agrobacteria right border sequence (RB), left border (LB).

Throughout the specification, several terms are employed that are defined in the following paragraphs.

As used herein, the term "nucleic acid construct" refers to a polynucleotide or oligonucleotide comprising nucleic acid sequences not normally associated in nature. A nucleic acid construct of the present invention is prepared, isolated, or manipulated by the hand of man. The terms "nucleic acid", "polynucleotide" and "oligonucleotide" are used herein interchangeably and refer to a deoxyribonucleotide (DNA) or ribonucleotide (RNA) polymer either in single- or double-stranded form. For the purposes of the present invention, these terms are not to be construed as limited with respect to the length of the polymer and should also be understood to encompass analogs of DNA or RNA polymers made from analogs of natural nucleotides and/or from nucleotides that are modified in the base, sugar and/or phosphate moieties.

As used herein, the term "gene" refers to a discrete nucleic acid sequence responsible for a discrete cellular product and/or performing one or more intracellular or extracellular functions. More specifically, the term "gene" refers to a nucleic acid that includes a portion encoding a protein and optionally encompasses regulatory sequences, such as promoters, enhancers, terminators, and the like, which are involved in the regulation of expression of the protein encoded by the gene of interest. The gene and regulatory sequences may be derived from the same natural source, or may be heterologous to one another. The definition can also include nucleic acids that do not encode proteins but rather provide templates for transcription of functional RNA molecules such as tRNAs, rRNAs, etc. Alternatively, a gene may define a genomic location for a particular event/function, such as the binding of proteins and/or nucleic acids.

As used herein, the term "gene expression" refers to the conversion of the information, contained in a gene, into a gene product. A gene product can be the direct transcriptional product of a gene (e.g., mRNA, tRNA, rRNA, antisense RNA, ribozyme structural RNA or any other type of RNA) or a protein produced by translation of an mRNA. Gene products also include RNAs that are modified by processes such as capping, polyadenylation, methylation, and editing, proteins post-translationally modified, and proteins modified by, for example, methylation, acetylation, phosphorylation, ubiquitination, ADP-ribosylation, myristilation, and glycosylation.

As used herein, the term "operably linked" refers to a relationship between two nucleic acid sequences wherein the expression of one of the nucleic acid sequences is controlled by, regulated by or modulated by the other nucleic acid sequence. Preferably, a nucleic acid sequence that is operably linked to a second nucleic acid sequence is covalently linked, either directly or indirectly, to such second sequence, although any effective three-dimensional association is acceptable. A single nucleic acid sequence can be operably linked to multiple other sequences. For example, a single promoter can direct transcription of multiple RNA species.

As used herein, the terms "promoter" and "promoter element" refer to a polynucleotide that regulates expression of a selected polynucleotide sequence operably linked to the promoter, and which effects expression of the selected polynucleotide sequence in cells. The term "plant promoter", as used herein, refers to a promoter that functions in a plant. Constitutive promoters as well as tissue-specific promoters which selectively function in a part of a plant body, including a flower, are preferable. Examples of plant promoters include, but are not limited to, Cauliflower mosaic virus (CaMV) 35S promoter and nopaline synthase promoter from *Agrobacterium tumefaciens*.

The term "transgene", as used herein, refers to an exogenous gene which, when introduced into a host cell through the hand of man, for example, using a process such as transformation, electroporation, particle bombardment, and the like, is expressed by the host cell and integrated into the cell's DNA such that the trait or traits produced by the expression of the transgene is inherited by the progeny of the transformed cell. A transgene may be partly or entirely heterologous (i.e., foreign to the cell into which it is introduced). Alternatively, a transgene may be homologous to an endogenous gene of the cell into which it is introduced, but is designed to be inserted (or is inserted) into the cell's genome in such a way as to alter the genome of the cell (e.g., it is inserted at a location which differs from that of the natural gene or its insertion results in a knockout). A transgene can also be present in a cell in the form of an episome. A transgene can include one or more transcriptional regulatory sequences and other nucleic acids, such as introns. Alternatively or additionally, a transgene is one that is not naturally associated with the vector sequences with which it is associated according to the present invention.

As will be clear from the context, the term "plant", as used herein, can refer to a whole plant, plant parts (e.g., cuttings, tubers, pollen), plant organs (e.g., leaves, stems, flowers, roots, fruits, branches, etc.), individual plant cells, groups of plant cells (e.g., cultured plant cells), protoplasts, plant extracts, seeds, and progeny thereof. The class of plants which can be used in the methods of the present invention is as broad as the class of higher plants amenable to transformation techniques, including both monocotyledonous and dicotyledonous plants, as well as certain lower plants such as algae. The term includes plants of a variety of a ploidy levels, including polyploid, diploid and haploid. In certain embodiments of the invention, plants are green field plants. In other embodiments, plants are grown specifically for "biomass energy". For example, suitable plants include, but are not limited to, corn, switchgrass, sorghum, miscanthus, sugarcane, poplar, pine, wheat, rice, soy, cotton, barley, turf grass, tobacco, bamboo, rape, sugar beet, sunflower, willow, and eucalyptus. Using transformation methods, genetically modified plants, plant cells, plant tissue, seeds, and the like can be obtained.

As used herein, the term "protoplast" refers to an isolated plant cell without cell walls which has the potency for regeneration into cell culture or a whole plant.

As used herein, the term "transformation" refers to a process by which an exogenous nucleic acid molecule (e.g., a vector or recombinant DNA molecule) is introduced into a recipient cell, callus or protoplast. The exogenous nucleic acid molecule may or may not be integrated into (i.e., covalently linked to) chromosomal DNA making up the genome of the host cell, callus or protoplast. For example, the exogenous polynucleotide may be maintained on an episomal element, such as a plasmid. Alternatively, the exogenous polynucleotide may become integrated into a chromosome so that it is inherited by daughter cells through chromosome replication. Methods for transformation include, but are not limited to, electroporation, magnetoporation, $Ca^{2+}$ treatment, injection, particle bombardment, retroviral infection, and lipofection.

As used herein, the term "stably transformed", when applied to a plant cell, callus or protoplast refers to a cell, callus or protoplast in which an inserted exogenous nucleic acid molecule is capable of replication either as an autonomously replicating plasmid or as part of the host chromosome. The stability is demonstrated by the ability of the transformed cells to establish cell lines or clones comprised of a population of daughter cells containing the exogenous nucleic acid molecule.

The terms "genetically modified" and "transgenic" are used herein interchangeably. A transgenic or genetically modified organism is one that has a genetic background which is at least partially due to manipulation by the hand of man through the use of genetic engineering. For example, the term "transgenic cell", as used herein, refers to a cell whose DNA contains an exogenous nucleic acid not originally present in the non-transgenic cell. A transgenic cell may be derived or regenerated from a transformed cell or derived from a transgenic cell. Exemplary transgenic cells in the context of the present invention include plant calli derived from a stably transformed plant cell and particular cells (such as leaf, root, stem, or reproductive cells) obtained from a transgenic plant. A "transgenic plant" is any plant in which one or more of the cells of the plant contain heterologous nucleic acid sequences introduced by way of human intervention. Transgenic plants typically express DNA sequences, which confer the plants with characters different from that of native, non-transgenic plants of the same strain. The progeny from such a plant or from crosses involving such a plant in the form of plants, seeds, tissue cultures and isolated tissue and cells, which carry at least part of the modification originally introduced by genetic engineering, are comprised by the definition.

As used herein, the term "regeneration" refers to the process of growing a plant from a plant cell (e.g., plant protoplast, plant callus or plant explant).

DETAILED DESCRIPTION OF CERTAIN PREFERRED EMBODIMENTS

As mentioned above, the present invention relates to improved systems and strategies for reducing costs and increasing yields of ethanol production from lignocellulosic biomass.

I. Lignocellulolytic Enzymes

In one aspect, the present invention provides plants engineered (i.e., genetically transformed) to produce one or more lignocellulolytic enzymes. Suitable lignocellulolytic enzymes include enzymes that are involved in the disruption and/or degradation of lignocellulose. Lignocellulosic biomass is a complex substrate in which crystalline cellulose is embedded within a matrix of hemicellulose and lignin. Lignocellulose represents approximately 90% of the dry weight of most plant material with cellulose making up between 30% to 50% of the dry weight of lignocellulose and hemicellulose making up between 20% and 50% of the dry weight of lignocellulose.

Disruption and degradation (e.g., hydrolysis) of lignocellulose by lignocellulolytic enzymes leads to the formation of substances including monosaccharides, disaccharides, polysaccharides and phenols. Lignocellulolytic enzymes include, but are not limited to, cellulases, hemicellulases and ligninases.

A—Cellulases

Cellulases are enzymes involved in cellulose degradation. Cellulase enzymes are classified on the basis of their mode of action. There are two basic kinds of cellulases: the endocellulases, which cleave the polymer chains internally; and the exocellulases, which cleave from the reducing and non-reducing ends of molecules generated by the action of endocellulases. Cellulases include cellobiohydrolases, endoglucanases, and β-D-glucosidases. Endoglucanases randomly attack the amorphous regions of cellulose substrate, yielding mainly higher oligomers. Cellubiohydrolases are exocellulases which hydrolyze crystalline cellulose and release cellobiose (glucose dimer). Both types of enzymes hydrolyze-1, 4-glycosidic bonds. β-D-glucosidases or cellulobiase converts oligosaccharides and cellubiose to glucose.

According to the present invention, plants may be engineered to comprise a gene encoding a cellulase enzyme. Alternatively, plants may be engineered to comprise more than one gene encoding a cellulase enzyme. For example, plants may be engineered to comprise one or more genes encoding a cellulase of the cellubiohydrolase class, one or more genes encoding a cellulase of the endoglucanase class, and/or one or more genes encoding a cellulase of the β-D-glucosidase class.

Examples of endoglucanase genes that can be used in the present invention can be obtained from *Acidothermus cellulolyticus* (U.S. Pat. No. 5,275,944; U.S. Pat. No. 5,536,655, Australian Patent No. AU 682125; Canadian Patent No. CA 2194478), *Aspergillus aculeatus* (U.S. Pat. No. 6,623,949; WO 94/14953), *Aspergillus kawachii* (U.S. Pat. No. 6,623, 949), *Aspergillus oryzae* (Kitamoto et al., Appl. Microbiol. Biotechnol., 1996, 46: 538-544; U.S. Pat. No. 6,635,465), *Aspergillus nidulans* (Lockington et al., Fungal Genet. Biol., 2002, 37: 190-196), *Cellulomonas fimi* (Wong et al., Gene, 1986, 44: 315-324), *Bacillus subtilis* (MacKay et al., Nucleic Acids Res., 1986, 14: 9159-9170), *Cellulomonas pachnodae* (Cazemier et al., Appl. Microbiol. Biotechnol., 1999, 52: 232-239), *Fusarium equiseti* (Goedegebuur et al., Curr. Genet., 2002, 41: 89-98), *Fusarium oxysporum* (Hagen et al., Gene, 1994, 150: 163-167; Sheppard et al., Gene, 1994, 150: 163-167), *Humicola insolens* (U.S. Pat. No. 5,912,157; Davies et al., Biochem J., 2000, 348: 201-207), *Hypocrea jecorina* (Penttila et al., Gene, 1986, 45: 253-263), *Humicola grisea* (Goedegebuur et al., Curr. Genet., 2002, 41: 89-98), *Micromonospora cellulolyticum* (Lin et al., J. Ind. Microbiol., 1994, 13: 344-350), *Myceliophthora thermophila* (U.S. Pat. No. 5,912,157), *Rhizopus oryzae* (Moriya et al., J. Bacteriol., 2003, 185: 1749-1756), *Trichoderma reesei* (Saloheimo et al., Mol. Microbiol., 1994, 13: 219-228), and *Trichoderma viride* (Kwon et al., Biosci. Biotechnol. Biochem., 1999, 63: 1714-1720; Goedegebuur et al., Curr. Genet., 2002, 41: 89-98).

In certain embodiments, plants are engineered to comprise the endo-1,4-β-glucanase E1 gene (GenBank Accession No. U33212). This gene was isolated from the thermophilic bacterium *Acidothermus cellulolyticus*. *Acidothermus cellulolyticus* has been characterized with the ability to hydrolyze and degrade plant cellulose. The cellulase complex produced by *A. cellulolyticus* is known to contain several different thermostable cellulase enzymes with maximal activities at temperatures of 75° C. to 83° C. These cellulases are resistant to inhibition from cellobiose, an end product of the reactions catalyzed by endo- and exo-cellulases.

The E1 endo-1,4-β-glucanase is described in detail in U.S. Pat. No. 5,275,944. This endoglucanase demonstrates a temperature optimum of 83° C. and a specific activity of 40 μmol glucose release from carboxymethylcellulose/min/mg protein. This E1 endoglucanase was further identified as having an isoelectric pH of 6.7 and a molecular weight of 81,000 daltons by SDS polyacrylamide gel electrophoresis. It is synthesized as a precursor with a signal peptide that directs it to the export pathway in bacteria. The mature enzyme is 521 amino acids (aa) in length. The crystal structure of the catalytic domain of about 40 kD (358 aa) has been described (J. Sakon et al., Biochem., 1996, 35: 10648-10660). Its pro/thr/ser-rich linker is 60 aa, and the cellulose binding domain (CBD) is 104 aa. The properties of the cellulose binding domain that confer its function are not well-characterized. Plant expression of the E1 gene has been reported (see for example, M. T. Ziegler et al., Mol. Breeding, 2000, 6: 37-46; Z. Dai et al., Mol. Breeding, 2000, 6: 277-285; Z. Dai et al., Transg. Res., 2000, 9: 43-54; and T. Ziegelhoffer et al., Mol. Breeding, 2001, 8: 147-158).

Examples of cellobiohydrolase genes that can be used in the present invention can be obtained from *Acidothermus cellulolyticus, Acremonium cellulolyticus* (U.S. Pat. No. 6,127,160), *Agaricus bisporus* (Chow et al., Appl. Environ. Microbiol., 1994, 60: 2779-2785), *Aspergillus aculeatus* (Takada et al., J. Ferment. Bioeng., 1998, 85: 1-9), *Aspergillus niger* (Gielkens et al., Appl. Environ. Microbiol., 65: 1999, 4340-4345), *Aspergillus oryzae* (Kitamoto et al., Appl. Microbiol. Biotechnol., 1996, 46: 538-544), *Athelia rolfsii* (EMBL accession No. AB103461), *Chaetomium thermophilum* (EMBL accession Nos. AX657571 and CQ838150), *Cullulomonas fimi* (Meinke et al., Mol. Microbiol., 1994, 12: 413-422), *Emericella nidulans* (Lockington et al., Fungal Genet. Biol., 2002, 37: 190-196), *Fusarium oxysporum* (Hagen et al., Gene, 1994, 150: 163-167), *Geotrichum* sp. 128 (EMBL accession No. AB089343), *Humicola grisea* (de Oliviera and Radford, Nucleic Acids Res., 1990, 18: 668; Takashima et al., J. Biochem., 1998, 124: 717-725), *Humicola nigrescens* (EMBL accession No. AX657571), *Hypocrea koningii* (Teeri et al., Gene, 1987, 51: 43-52), *Myceliopitera thermophila* (EMBL accession No. AX657599), *Neocallimastix patriciarum* (Denman et al., Appl. Environ. Microbiol., 1996, 62: 1889-1896), *Phanerochaete chrysosporium* (Tempelaars et al., Appl. Environ. Microbiol., 1994, 60: 4387-4393), *Thermobifida fusca* (Zhang, Biochemistry, 1995, 34: 3386-3395), *Trichoderma reesei* (Terri et al., Bio-Technology, 1983, 1: 696-699; Chen et al., BioTechnology, 1987, 5: 274-278), and *Trichoderma viride* (EMBL accession Nos. A4368686 and A4368688).

Examples of β-D-glucosidase genes that can be used in the present invention can be obtained from *Aspergillus aculeatus* (Kawaguchi et al., Gene, 1996, 173: 287-288), *Aspergillus kawachi* (Iwashita et al., Appl. Environ. Microbiol., 1999, 65: 5546-5553), *Aspergillus oryzae* (WO 2002/095014), *Cellulomonas biazotea* (Wong et al., Gene, 1998, 207: 79-86), *Penicillium funiculosum* (WO 200478919), *Saccharomycopsis fibuligera* (Machida et al., Appl. Environ. Microbiol., 1988, 54: 3147-3155), *Schizosaccharomyces pombe* (Wood et al., Nature, 2002, 415: 871-880), and *Trichoderma reesei* (Barnett et al., BioTechnology, 1991, 9: 562-567).

Transgene expression of cellulases in plants for the conversion of cellulose to glucose has been reported (see, for example, Y. Jin Cai et al., Appl. Environ. Microbiol., 1999, 65: 553-559; C. R. Sanchez et al., Revista de Microbiologica, 1999, 30: 310-314; R. Cohen et al., Appl. Environ., 2995, 71: 2412-2417; Z. Dai et al., Transg. Res., 2005, 14: 627-543).

B—Hemicellulases

Hemicellulases are enzymes that are involved in hemicellulose degradation. Hemicellulases include xylanases, arabinofuranosidases, acetyl xylan esterases, glucuronidases, mannanases, galactanases, and arabinases. Similar to cellulase enzymes, hemicellulases are classified on the basis of their mode of action: the endo-acting hemicellulases attack internal bonds within the polysaccharide chain; the exo-acting hemicellulases act progressively from either the reducing or non-reducing end of polysaccharide chains According to the present invention, plants may be engineered to comprise a gene encoding a hemicellulase enzyme. Alternatively, plants may be engineered to comprise more than one gene encoding a hemicellulase enzyme. For example, plants may be engineered to comprise one or more genes encoding a hemicellulase of the xylanase class, one or more genes encoding a hemicellulase of the arabinofuranosidase class, one or more genes encoding a hemicellulase of the acetyl xylan esterase class, one or more genes encoding a hemicellulase of the glucuronidase class, one or more genes encoding a hemicellulase of the mannanase class, one or more genes encoding a hemicellulase of the galactanase class, and/or one or more genes encoding a hemicellulase of the arabinase class.

Examples of endo-acting hemicellulases include endoarabinanase, endoarabinogalactanase, endoglucanase, endomannanase, endoxylanase, and feraxan endoxylanase. Examples of exo-acting hemicellulases include α-L-arabinosidase, β-L-arabinosidase, α-1,2-L-fucosidase, α-D-galactosidase, β-D-galactosidase, β-D-glucosidase, β-D-glucuronidase, β-D-mannosidase, β-D-xylosidase, exo-glucosidase, exo-cellobiohydrolase, exo-mannobiohydrolase, exo-mannanase, exo-xylanase, xylan α-glucuronidase, and coniferin β-glucosidase.

Hemicellulase genes can be obtained from any suitable source, including fungal and bacterial organisms, such as *Aspergillus, Disporotrichum, Penicillium, Neurospora, Fusarium, Trichoderma, Humicola, Thermomyces*, and *Bacillus*. Examples of hemicellulases that can be used in the present invention can be obtained from *Acidothermus cellulolyticus* (U.S. Pat. No. 7,112,429), *Acidobacterium capsulatum* (Inagaki et al., Biosci. Biotechnol. Biochem., 1998, 62: 1061-1067), *Agaricus bisporus* (De Groot et al., J. Mol. Biol., 1998, 277: 273-284), *Aspergillus aculeatus* (U.S. Pat. No. 6,197,564; U.S. Pat. No. 5,693,518), *Aspergillus kawachii* (Ito et al., Biosci. Biotechnol. Biochem., 1992, 56: 906-912), *Aspergillus niger* (EMBL accession No. AF108944), *Magnaporthe grisea* (Wu et al., Mol. Plant Microbe Interact., 1995, 8: 506-514), *Penicillium chrysogenum* (Haas et al., Gene, 1993, 126: 237-242), *Talaromyces emersonii* (WO 02/24926), and *Trichoderma reesei* (EMBL accession Nos. X69573, X69574, and AY281369).

In certain embodiments, plants are engineered to comprise the *Cochlibolus carbonum* endoxylanase (XYL1) (P. C. Apel et al., Mol. Plant Microbe Interact., 1993, 6: 467-473) (see the Examples section).

C—Ligninases

Ligninases are enzymes that are involved in the degradation of lignin. Lignin-degrading enzymes include, but are not limited to, lignin peroxidases, manganese-dependent peroxidases, hybrid peroxidases (which exhibit combined properties of lignin peroxidases and manganese-dependent peroxidases), and laccases. Hydrogen peroxide, required as co-substrate by the peroxidases, can be generated by glucose oxidase, aryl alcohol oxidase, and/or lignin peroxidase-activated glyoxal oxidase.

According to the present invention, plants may be engineered to comprise a gene encoding a ligninase enzyme. Alternatively, plants may be engineered to comprise more than one gene encoding a ligninase enzyme. For example, plants may be engineered to comprise one or more genes encoding a ligninase of the lignin peroxidase class, one or more genes encoding a ligninase of the manganese-dependent peroxidase class, one or more genes encoding a ligninase of the hybrid peroxidase class, and/or one or more genes encoding a ligninase of the laccase class.

Lignin-degrading genes may be obtained from *Acidothermus cellulolyticus, Bjerkandera adusta, Ceriporiopsis subvermispora* (see WO 02/079400), *Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride*.

Examples of genes encoding ligninases that can be used in the invention can be obtained from *Bjerkandera adusta* (WO 2001/098469), Ceriporiopsis subvermispora (Conesa et al., J. Biotechnol., 2002, 93: 143-158), *Cantharellus cibariusi* (Ng et al., Biochem. and Biophys. Res. Comm., 2004, 313: 37-41), *Coprinus cinereus* (WO 97/008325; Conesa et al., J. Biotechnol., 2002, 93: 143-158), *Lentinula edodes* (Nagai et al., Applied Microbiol. and Biotechnol., 2002, 60: 327-335, 2002), *Melanocarpus albomyces* (Kiiskinen et al., FEBS Letters, 2004, 576: 251-255, 2004), *Myceliophthora thermophila* (WO 95/006815), *Phanerochaete chrysosporium* (Conesa et al., J. Biotechnol., 2002, 93: 143-158; Martinez, Enz, Microb, Technol, 2002, 30: 425-444), *Phlebia radiata* (Conesa et al., J. Biotechnol., 2002, 93: 143-158), *Pleurotus eryngii* (Conesa et al., J. Biotechnol., 2002, 93: 143-158), *Polyporus pinsitus* (WO 96/000290), *Rigidoporus lignosus* (Garavaglia et al., J. of Mol. Biol., 2004, 342: 1519-1531), *Rhizoctonia solani* (WO 96/007988), *Scytalidium thermophilum* (WO 95/033837), *Tricholoma giganteum* (Wang et al., Biochem. Biophys. Res. Comm., 2004, 315: 450-454), and *Trametes versicolor* (Conesa et al., J. Biotechnol., 2002, 93: 143-158).

For example, plants may be engineered to comprise one or more lignin peroxidases. Genes encoding lignin peroxidases may be obtained from *Phanerochaete chrysosporium* or *Phlebia radiata*. Lignin-peroxidases are glycosylated heme proteins (MW 38 to 46 kDa) which are dependent on hydrogen peroxide for activity and catalyze the oxidative cleavage of lignin polymer. At least six (6) heme proteins (H1, H2, H6, H7, H8 and H10) with lignin peroxidase activity have been identified *Phanerochaete chrysosporium* in strain BKMF-1767. In certain embodiments, plants are engineered to comprise the white rot filamentous *Phanerochaete chrysosporium* ligninase (CGL5) (H. A. de Boer et al., Gene, 1988, 69(2): 369) (see the Examples section).

D—Other Lignocellulolytic Enzymes

In addition to cellulases, hemicellulases and ligninases, lignocellulolytic enzymes that can be used in the practice of the present invention also include enzymes that degrade pectic substances. Pectic substances are composed of homogalacturonan (or pectin), rhamnogalacturonan, and xylogalacturonan. Enzymes that degrade homogalacturonan include pectate lyase, pectin lyase, polygalacturonase, pectin acetyl esterase, and pectin methyl esterase. Enzymes that degrade rhamnogalacturonan include alpha-arabinofuranosidase, beta-galactosidase, galactanase, arabinanase, alpha-arabinofuranosidase, rhamnogalacturonase, rhamnogalacturonan lyase, and rhamnogalacturonan acetyl esterase. Enzymes that degrade xylogalacturonan include xylogalacturonosidase, xylogalacturonase, and rhamnogalacturonan lyase. Other enzymes that may enhance or promote lignocellulose disruption and/or degradation include, but are not limited to, amylases (e.g., alpha amylase and glucoamylase), esterases, lipases, phospholipases, phytases, proteases, and peroxidases.

E—Combinations of Lignocellulolytic Enzymes

According to the present invention, plants may be engineered to comprise a gene encoding a lignocellulolytic enzyme, e.g., a cellulase enzyme, a hemicellulase enzyme, or a ligninase enzyme. Alternatively, plants may be engineered to comprise two or more genes encoding lignocellulolytic enzymes, e.g., enzymes from different classes of cellulases, enzymes from different classes of hemicellulases, enzymes from different classes of ligninases, or any combinations thereof. For example, combinations of genes may be selected to provide efficient degradation of one component of lignocellulose (e.g., cellulose, hemicellulose, or lignin). Alternatively, combinations of genes may be selected to provide efficient degradation of the lignocellulosic material.

In certain embodiments, genes are optimized for the substrate (e.g., cellulose, hemicellulase, lignin or whole lignocellulosic material) in a particular plant (e.g., corn, tobacco, switchgrass). Tissue from one plant species is likely to be physically and/or chemically different from tissue from another plant species. Selection of genes or combinations of genes to achieve efficient degradation of a given plant tissue is within the skill of artisans in the art.

In some embodiments, combinations of genes are selected to provide for synergistic enzymes activity (i.e., genes are selected such that the interaction between distinguishable enzymes or enzyme activities results in the total activity of the enzymes taken together being greater than the sum of the effects of the individual activities).

Efficient lignocellulolytic activity may be achieved by production of two or more enzymes in a single transgenic plant. As mentioned above, plants may be transformed to express more than one enzyme, for example, by employing the use of multiple gene constructs encoding each of the selected enzymes or a single construct comprising multiple nucleotide sequences encoding each of the selected enzymes. Alternatively, individual transgenic plants, each stably transformed to express a given enzyme, may be crossed by methods known in the art (e.g., pollination, hand detasslling, cytoplasmic male sterility, and the like) to obtain a resulting plant that can produce all the enzymes of the individual starting plants.

Alternatively, efficient lignocellulolytic activity may be achieved by production of two or more lignocellulolytic enzymes in separate plants. For example, three separate lines of plants (e.g., corn), one expressing one or more enzymes of the cellulase class, another expressing one or more enzymes of the hemicellulase class and the third one expressing one or more enzymes of the ligninase class, may be developed and grown simultaneously. The desired "blend" of enzymes produced may be achieved by simply changing the seed ratio, taking into account farm climate and soil type, which are expected to influence enzyme yields in plants.

Other advantages of this approach include, but are not limited to, increased plant health (which is known to be adversely affected as the number of introduced genes increases), simpler transformations procedures and great flexibility in incorporating the desired traits in commercial plant varieties for large-scale production.

F—Methods of Identification of Microbial Cellulase Enzymes that can Function in Plants Currently it is a lengthy and labor-intensive process to determine if a microbial enzyme can be functionally expressed in plants through recombinant DNA techniques. Stable transgenic plants have to be generated and characterized, then the enzymes have to be extracted from the biomass and tested in vitro. The present invention provides screening methods for the rapid identification of microbial cellulase enzymes that can function in plants. In certain embodiments, screening methods of the present invention allow assessment of enzyme activity in plant tissues in a matter of days or hours rather than weeks.

More specifically, screening methods are provided herein that use plant tissues transiently transformed to express the transgene of a gene of interest and assess cellulase enzymatic activity. Transient expression of transgenes in plant tissues reduces the time necessary to produce enzymes from months to days. An embodiment of the inventive screening methods is described in Example 9. In this screening method, tobacco leaves are used. The soil bacterium *Agrobacterium tumefaciens* may be used to transfer the gene of interest contained in a standard plant transformation vector into the tobacco cells by infiltrating the bacteria into the leaf (Cazzanelli and Velten, Planta, 2006, 224: 582-597). Three to five days later the infiltrated tissue expresses the transgene at sufficient levels to analyze enzymatic activity.

Cellulase enzymatic activity can be analyzed using any suitable method. As described in Example 9, enzymatic activity may be assessed using carboxyl-methyl cellulose (CMC). Cellulase enzymes can rapidly hydrolyze the 1,4-glucan bonds linking glucan molecules together in cellulose. CMC can be stained with the dye Congo Red, however, when hydrolyzed by cellulase enzymes, such as E1 endoglucanase from *Acidothermus cellulolyticus*, CMC is no longer reactive to Congo Red. CMC can be used with agar to form a solid media that can be poured in Petri dishes to form CMC plates (M. Ziegler et al., Molecular Breeding, 200, 6: 37-46; T. Teather et al., App. & Env. Microbiology, 1982, 43: 777-780). Transgenic plants expressing the gene of interest can be placed directly on the surface of the CMC plates and allowed to incubate. After incubation and removal of the plant biomass, the CMC plate is flooded with Congo red to stain the cellulose in the media. Absence of staining by Congo Red on the plate (i.e., hydrolysis of CMC) is indicative of cellular enzymatic activity of the transgene.

G—Methods of Codon Optimization of Gene Sequences for Increased Expression of Microbial Cellulase Enzymes in Plants For optimal expression of microbial enzymes in plants, preferential changes in the codon sequences is important. The present invention provides a method to modify gene sequences for increased expression of microbial cellulases in plants. The inventive method comprises the construction of a composite codon usage table by averaging the codon usage of at least two different plants of known, sequenced genomes. The composite codon usage table is then used as a template to modify the polynucleotide sequence of a microbial polynucleotide gene sequence encoding a lignocellulolytic enzyme. This method allows for the generation of polynucleotide sequences that are better suited for expression of microbial enzymes in plants.

In the method of the invention, the averaging may be performed using the codon usage of two, three, four, or more than four different plants. As will be recognized by one skilled in the art, the inventive method may be performed using codon usage information from any number of plants and from any combination of plants. In certain embodiments, the plants are selected such as at least one is a monocot plant and at least one is a dicot plant. In certain embodiments, the plants are selected based on the intended purpose of the polynucleotide (e.g., a microbial gene sequence to be used for expression in maize and tobacco will preferably be codon optimized using a composite codon usage table constructed by averaging the codon usage of *Zea mays*, and *Nicotiana tabacum*.

Also provided herein are isolated polynucleotide sequences that have been codon optimized according the inventive method, as well as plant cells, plant parts and plants that have been transformed using these codon optimized polynucleotides.

An embodiment of the inventive method is described in Example 8 where a composite codon usage table was constructed by averaging the codon usages of *Zea mays*, *Arabidopsis thaliana*, and *Nicotiana tabacum*. Using this method, three codon optimized polynucleotide have been generated (see Example 8): a polynucleotide sequence encoding E1 endoglucanase, which comprises SEQ ID NO. 1; a polynucleotide sequence encoding family 48 glycoside hydrolase, which comprises SEQ ID NO. 2; and a polynucleotide sequence encoding family 10 glycoside hydrolase, which comprises SEQ ID NO. 3.

H—Other Properties

In certain embodiments, plants are engineered to express a lignocellulolytic enzyme (e.g., a cellulase, a hemicellulase or a ligninase) at a level greater than 0.5% total soluble protein (TSP). In other embodiments, plants are engineered to express a lignocellulolytic enzyme at a level greater than 5% TSP. In yet other embodiments, plants are engineered to express a lignocellulolytic enzyme at a level greater than 10% TSP. In still other embodiments, plants are engineered to express a lignocellulolytic enzyme at a level greater than 20% TSP. High levels of enzyme production will lead to more complete lignocellulosic material degradation, particularly when used in a "blend" of transgenic plant varieties, as described above, where each variety produces an enzyme that will hydrolyze target lignocellulose from the other varieties as well as from its own biomass.

For example, targeting cellulose, hemicellulose and lignin—which together represent approximately 75% of corn stover biomass—is expected to hydrolyze more than twice the lignocellulosic biomass compared to a cellulase-only approach.

Figure 18:
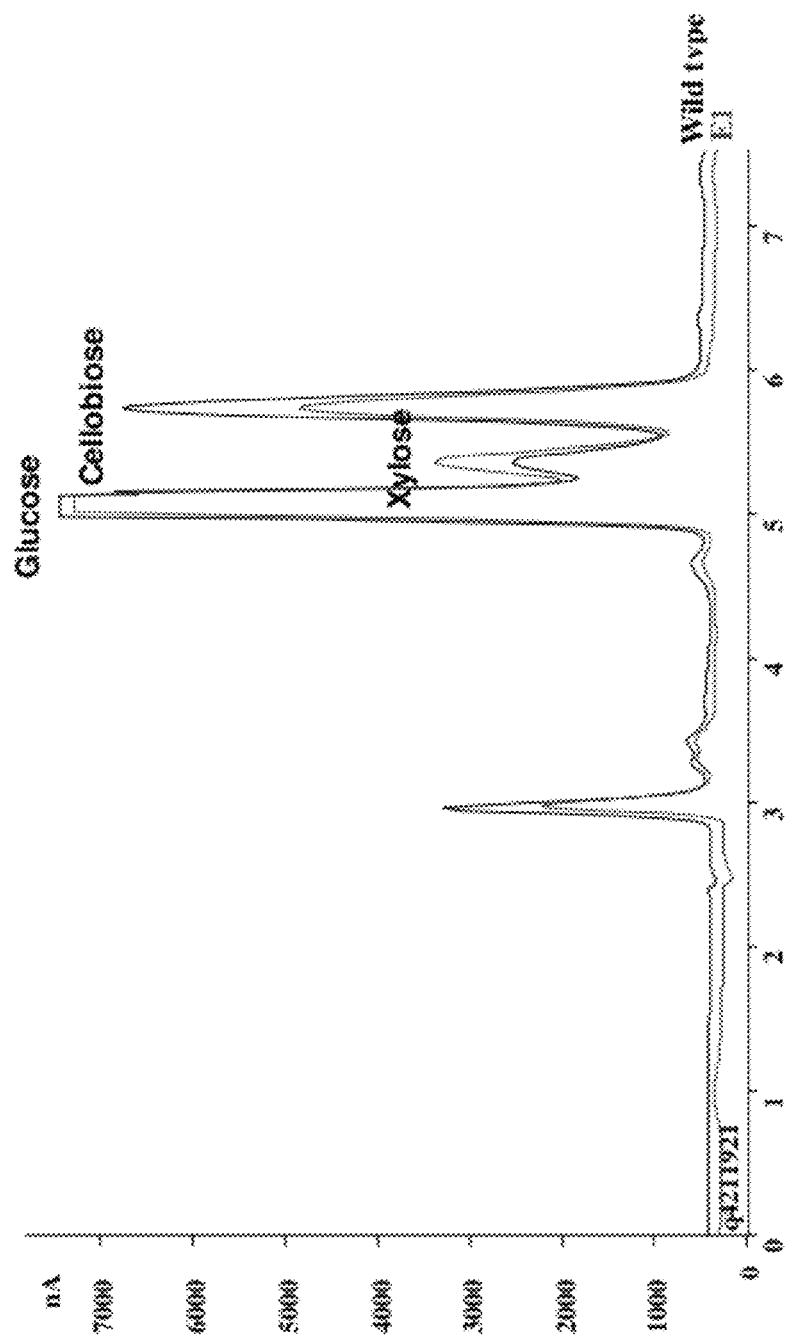
FIG. 18 shows IC chromatogram illustrating increased production of xylose in tobacco plants transformed with the E1 gene. E1 transformed or wild type tobacco plant tissue was incubated at 80° C. for 2 hours in citrate buffer (pH 5). The suspension was filtered and analyzed for soluble sugars. Xylose (a component of hemicellulose) concentration extract of E1 plants was substantially higher (14.8 g/kg) than the xylose concentrations in the wild-type extract (3 g/kg).

In addition to hydrolyzing the putative substrate, plant-expressed enzymes can also have a degrading/hydrolyzing effect on other polysaccharides as well. For example, FIG. 18 illustrates the ability of E1 expressed in plants to reduce the degree of polymerization (DP) not just of cellulose but of hemicellulose, increasing xylose levels as well as glucose levels.

Enzyme genes incorporated in plants according to the present invention preferably exhibit two properties: they are both heat stable and show optimum activity at desired ethanol production temperatures. Advantages include (1) low enzymatic activity under normal plant growing conditions, thus preventing or minimizing adverse effects to plant growth ("yield drag"), and (2) lower required enzyme expression in the plant and thus increased ability to add additional enzyme traits to the same plant.

Accordingly, the present invention also provides plants engineered to express one or more lignocellulolytic enzymes and to exhibit at least one desirable trait (see below).

II. Genes for Enhanced Biomass and Delayed Flowering

The present invention provides plants engineered (i.e., genetically transformed) to maximize plant production of biomass and/or cellulase, and/or to delay plant flowering.

After transition from vegetative plant growth (i.e., production of leaves) to a reproductive state (i.e., production of flowers), both biomass and cellulase production decreases. Therefore, if the onset of flowering could be delayed, this would give the plant a longer productive period. An additional benefit of a delay in flowering would be to reduce the likelihood of cross-pollination between genetically modified and native plants as their flowering times would be less likely to coincide (i.e., bioconfinement).

The control of flowering time in plants is an extremely complex, carefully regulated process of plant development, with approximately 80 genetic loci known to affect flowering time in *Arabidopsis thaliana* (Y. Y. Levy and C. Dean, Plant Cell, 1998, 10: 1973-1990). This multi-factorial control model attempts to account for the variety of flowering responses including phytohormones and environmental cues, and how they interact to control the development transition to flowering under the correct environmental and endogenous conditions. In *Arabidopsis*, which is a long-day facultative plant, at least four pathways that control flowering time have been identified. Two pathways mediate signals from the environment (day length and vernalization, cold temperature) and two are independent of external environmental signals (autonomous and Gibberellic acid-dependent) and appear to monitor the endogenous development status of the plant (Y. Y. Levy and C. Dean, Plant Cell, 1998, 10: 1973-1990).

Interaction of the key flowering time genes from *Arabidopsis* is now fairly well understood. In order to delay this development process it is necessary to upset the usual balance of the information flow, either by disrupting a promotional gene or by increasing the activity of an inhibitory one. A good candidate for this is the inhibitor Flowering Locus C gene, or FLC. This is a dosage-dependent repressor of flowering in *Arabidopsis* (S. D. Michaels and R. M. Amasino, Plant Cell, 1999, 11: 949-956), which operates by negatively regulating the expression of genes that promote flowering, such as SOC1 and FT.

FLC is one of the key regulatory genes in floral induction and integrates responses from both autonomous flowering pathway(s) (D. T. Rouse et al., The Plant Journal, 2002, 29: 183-191; H. Zhang and S. van Nocker, The Plant Journal, 2002, 31: 663-673) and the vernalization pathway (H. Zhang and S. van Nocker, The Plant Journal, 2002, 31: 663-673; J. Moon et al., The Plant Journal, 2003, 35: 613-623). Expression of *Arabidopsis* FLC (AtFLC) has been shown to delay flowering in both *Brassica napus* (M. Tadege et al., The Plant Journal, 2001, 28: 545-553) and rice, *Oryza sativa* (M. Tadege et al., Plant Biotechnol. J., 2003, 1: 361-369) and reciprocal experiments expressing *B. napus* orthologues of FLC (BnFLC1-5) in *Arabidopsis* also significantly delayed flowering (M. Tadege et al., The Plant Journal, 2001, 28: 545-553). The effectiveness of AtFLC in delaying flowering in species as diverse as *Brassica* (a dicot) and rice (a monocot) highlights the ubiquity of this gene product in floral induction. Importantly, when introduced to *Arabidopsis*, FLC produced massive leaves along with a long-term delay in flowering (S. D. Michaels and R. M. Amasino, Plant Cell, 1999, 11: 949-956). This increase in biomass is highly desirable for biofuels and phytoremediation applications.

As shown in the Examples section below, the Applicants have confirmed that expression of AtFLC in tobacco delayed flowering and significantly increased plant biomass. Therefore, the central role that FLC plays in repressing floral induction makes it an ideal choice to delay corn flowering as a method of bioconfinement and to increase corn plant biomass.

Accordingly, the present invention provide plants that are engineered to express FLC and to produce at least one lignocellulolytic enzyme (e.g., a cellulase, a hemicellulase or a ligninase), which can be used advantageously in ethanol production.

Also provided by the present invention are plants that are engineered to produce at least one lignocellulolytic enzyme and that are modified (e.g., engineered) for total sterility (i.e., bioconfinement). Genes and techniques for inducing plant total sterility are known in the art.

III. Fermentation Genes

In one aspect, the present invention provides plants engineered (i.e., genetically transformed) to express substances (e.g., enzymes) that are involved in the fermentation of plant sugars into alcohol and/or substances that can assist in the fermentation process.

For example, yeast genes may be incorporated into the genome 6f plants. Such genes can be obtained from different yeasts such as *Candida kefyr, Pichia stipitis*, respiratory deficient strains of *Saccharomyces cerevisiae, Hansenula anomala, Hansenula jadinii, Hansenula fabianii* and *Pachysolen tannophilus*.

It would be particularly advantageous to incorporate a gene expressing an enzyme that converts pentoses (e.g., xylose or arabinose resulting from hydrolysis of hemicellulose) to more easily fermented sugars. *S. cerevisiae*, which is generally used in the fermentation process involved in ethanol production, ferments the hexose sugars glucose, galactose and mannose, but is unable to ferment the pentose sugars xylose and arabinose due to the lack of one or more enzymatic steps. *S. cerevisiae* can ferment xylulose, an isomerization product of xylose, to ethanol (Wang et al., Biochem. Biophys. Res. Commun., 1980, 94: 248-254; Chiang et al., Appl. Environ. Microbiol., 1981, 42: 84-289; Senac and Hahn-Hagerdal, Appl. Environ. Microbiol. 56:120-126, 1990). Therefore, incorporating a gene for an isomerase that converts xylose to xylulose would allow more efficient use of hemicellulose for ethanol production and reduce the problems associated with unfermented sugars left in dried distilled grain (DDG).

In eukaryotic cells, the initial metabolism of xylose is catalyzed by a xylose reductase (XR), which reduces xylose to xylitol, and a xylitol dehydrogenase (XDH), which oxidizes xylitol to xylulose. Xylulose is then phosphorylated to xylulose 5-phosphate by a xylulose kinase (XK) and further metabolized through the pentose phosphate pathway and glycolysis to ethanol. Sources for XR and XHD include xylose-fermenting yeasts, *Pachysolen tannophilus* (Toivola et al., Appl. Environ. Microbiol., 1984, 47: 1221-1223), *Candida shehatae* (J. C. Dupreez and J. P. van der Walt, Biotechnol. Lett., 1983, 5: 357-362), and *Pichia stipitis* (Grootjen et al., Enzyme Microb. Technol., 1990, 12: 20-23), which have been extensively characterized. The genes for XR and XDH from the xylose fermenting yeast *Pichia stipitis* have been cloned (WO 91/15588; Kotter and Ciriacy, Appl. Microbiol. Biotechnol. 38:776-783, 1993 and references cited therein).

In certain embodiments, a transgenic plant according to the present invention is engineered to comprise one or more genes encoding one or more enzyme that convert xylose to xylulose (e.g., genes encoding XR or XDH).

Alternatively or additionally, a transgenic plant of the invention may be engineered to comprise one or more genes encoding substances that can assist in the fermentation process involved in ethanol production from biomass feedstocks. Examples of such genes include genes that provide increased plant uptake of nutrients needed by microorganisms used in the fermentation process, such as PHT1 or NRT1. Nutrients that allow growth of fermentation microorganisms include, for example, magnesium, nitrogen, potassium, phosphate, metals and vitamins. Other examples of suitable genes include genes that produce heat-resistant antibiotics or bacterial compounds to prevent bacterial contamination of the mash. Certain bacteria cause build-up of acetic acid and lactic acid that are toxic to yeast, which causes an important problem to ethanol producers. Other examples of suitable genes include genes that produce substances that alter the viscosity of the biomass mash during processing, such as the hydrolysis of polysaccharides and lignins by lignocellulolytic enzymes. Maintaining the target viscosity of the mash is an important objective of the ethanol producer.

IV. Nucleic Acid Constructs

Nucleic acid constructs to be used in the practice of the present invention generally encompass expression cassettes for expression in the plant of interest. The cassette generally includes 5' and 3' regulatory sequences operably linked to a nucleotide sequence encoding a lignocellulolytic enzyme (e.g., a cellulase, a hemicellulase or ligninase).

Expression Cassettes

Techniques used to isolate or clone a gene encoding an enzyme (e.g., a lignocellulolytic enzyme) are known in the art and include isolation from genomic DNA, preparation from cDNA, or a combination thereof. The cloning of a gene from such genomic DNA, can be effected, e.g., by using polymerase chain reaction (PCR) or antibody screening or expression libraries to detect cloned DNA fragments with shared structural features (Innis et al., "PCR: A Guide to Method and Application", 1990, Academic Press: New York). Other nucleic acid amplification procedures such as ligase chain reaction (LCR), ligated activated transcription (LAT) and nucleotide sequence-based amplification (NASBA) may be used.

The expression cassette will generally include in the 5'-3' direction of transcription, a transcriptional and translational initiation region, a coding sequence for a lignocellulolytic enzyme, and a transcriptional and translational termination region functional in plants. The transcriptional initiation region, i.e., the promoter, can be native or analogous (i.e., found in the native plant) or foreign or heterologous (i.e., not found in the native plant) to the plant host. Additionally, the promoter can be the natural sequence or alternatively a synthetic sequence.

In certain embodiments, the promoter is a constitutive plant promoter. Examples of plant promoters include, but are not limited to, the 35S cauliflower mosaic virus (CaMV) promoter, a promoter of nopaline synthase and a promoter of octopine synthase. Examples of other constitutive promoters used in plants are the 19S promoter, and promoters from genes encoding actin and ubiquitin. Promoters may be obtained from genomic DNA by using polymerase chain reaction (PCR), and then cloned into the construct.

Other sequences that can be present in nucleic acid constructs are sequences that enhance gene expression such as intron sequences and leader sequences. Examples of introns that have been reported to enhance expression include, but are not limited to, the introns of the Maize Adh1 gene and introns of the Maize bronze1 gene (J. Callis et. al., Genes Develop. 1987, 1: 1183-1200). Examples of non-translated leader sequences that are known to enhance expression include, but are not limited to, leader sequences from Tobacco Mosaic Virus (TMV, the "omegasequence"), Maize Chlorotic Mottle Virus (MCMV), and Alfalfa Mosaic Virus (AlMV) (see, for example, D. R. Gallie et al., Nucl. Acids Res. 1987, 15: 8693-8711; J. M. Skuzeski et. al., Plant Mol. Biol. 1990, 15: 65-79).

The transcriptional and translational termination region can be native with the transcription initiation region, can be native with the operably linked polynucleotide sequence of interest, or can be derived from another source. Convenient termination regions are available from the $T_i$-plasmid of *A. tumefaciens*, such as the octopine synthase and nopaline synthase termination regions (An et al., Plant Cell, 1989, 1: 115-122; Guerineau et al., Mol. Gen. Genet. 1991, 262: 141-144; Proudfoot, Cell, 1991, 64: 671-674; Sanfacon et al., Genes Dev. 1991, 5: 141-149; Mogen et al., Plant Cell, 1990, 2:1261-1272; Munroe et al., Gene, 1990, 91:151-158; Ballas et al., Nucleic Acids Res., 1989, 1-7: 7891-7903; and Joshi et al., Nucleic Acid Res., 1987, 15: 9627-9639).

Where appropriate, the gene(s) or polynucleotide sequence(s) encoding the enzyme(s) of interest may be modified to include codons that are optimized for expression in the transformed plant (Campbell and Gowri, Plant Physiol., 1990, 92: 1-11; Murray et al., Nucleic Acids Res., 1989, 17: 477-498; Wada et al., Nucl. Acids Res., 1990, 18: 2367, and U.S. Pat. Nos. 5,096,825; 5,380,831; 5,436,391; 5,625,136, 5,670,356 and 5,874,304). Codon optimized sequences are synthetic sequences, and preferably encode the identical polypeptide (or an enzymatically active fragment of a full length polypeptide which has substantially the same activity as the full length polypeptide) encoded by the non-codon optimized parent polynucleotide which encodes a lignocellulolytic enzyme.

Other Polynucleotide Sequences

Optional components of nucleic acid constructs include one or more marker genes. Marker genes are genes that impart a distinct phenotype to cells expressing the marker gene and thus allow transformed cells to be distinguished from cells that do not have the marker. Such genes may encode either a selectable or screenable marker. The characteristic phenotype allows the identification of cells, groups of cells, tissues, organs, plant parts or whole plants containing the construct. Many examples of suitable marker genes are known in the art. The marker may also confer additional benefit(s) to the transgenic plant such as herbicide resistance, insect resistance, disease resistance, and increased tolerance to environmental stress (e.g., drought).

Alternatively, a marker gene can provide some other visibly reactive response (e.g., may cause a distinctive appearance such as color or growth pattern relative to plants or plant cells not expressing the selectable marker gene in the presence of some substance, either as applied directly to the plant or plant cells or as present in the plant or plant cell growth media). It is now well known in the art that transcriptional activators of anthocyanin biosynthesis, operably linked to a suitable promoter in a construct, have widespread utility as non-phytotoxic markers for plant cell transformation.

Examples of markers that provide resistance to herbicides include, but are not limited to, the bar gene from *Streptomyces hygroscopicus* encoding phosphinothricin acetylase (PAT), which confers resistance to the herbicide glufosinate; mutant genes which encode resistance to imidazalinone or sulfonylurea such as genes encoding mutant form of the ALS and AHAS enzyme (Lee et al., EMBO J., 1988, 7: 1241; Miki et al., Theor. Appl. Genet., 1990, 80: 449; and U.S. Pat. No. 5,773,702); genes which confer resistance to glycophosphate such as mutant forms of EPSP synthase and aroA; resistance to L-phosphinothricin such as the glutamine synthetase genes; resistance to glufosinate such as the phosphinothricin acetyl transferase (PAT and bar) gene; and resistance to phenoxy propionic acids and cyclohexones such as the ACCAse inhibitor-encoding genes (Marshall et al., Theor. Appl. Genet., 1992, 83: 435).

Examples of genes which confer resistance to pests or disease include, but are not limited to, genes encoding a *Bacillus thuringiensis* protein such as the delta-endotoxin (U.S. Pat. No. 6,100,456); genes encoding lectins (Van Damme. et al., Plant Mol. Biol., 1994, 24: 825); genes encoding vitamin-binding proteins such as avidin and avidin homologs which can be used as larvicides against insect pests; genes encoding protease or amylase inhibitors, such as the rice cysteine proteinase inhibitor (Abe et al., J. Biol. Chem., 1987, 262: 16793) and the tobacco proteinase inhibitor I (Hubb et al., Plant Mol. Biol., 1993, 21: 985); genes encoding insect-specific hormones or pheromones such as ecdysteroid and juvenile hormone, and variants thereof, mimetics based thereon, or an antagonists or agonists thereof; genes encoding insect-specific peptides or neuropeptides which, upon expression, disrupts the physiology of the pest; genes encoding insect-specific venom such as that produced by a wasp, snake, etc.; genes encoding enzymes responsible for the accumulation of monoterpenes, sesquiterpenes, asteroid, hydroxamic acid, phenylpropanoid derivative or other non-protein molecule with insecticidal activity; genes encoding enzymes involved in the modification of a biologically active molecule (U.S. Pat. No. 5,539,095); genes encoding peptides which stimulate signal transduction; genes encoding hydrophobic moment peptides such as derivatives of Tachyplesin which inhibit fungal pathogens; genes encoding a membrane permease, a channel former or channel blocker (Jaynes et al., Plant Sci., 1993, 89: 43); genes encoding a viral invasive protein or complex toxin derived therefrom (Beachy et al., Ann. Rev. Phytopathol., 1990, 28: 451); genes encoding an insect-specific antibody or antitoxin or a virus-specific antibody (Tavladoraki et al., Nature, 1993, 366: 469); and genes encoding a developmental-arrestive protein produced by a plant, pathogen or parasite which prevents disease.

Examples of genes which confer resistance to environmental stress include, but are not limited to, mtld and HVA1, which are genes that confer resistance to environmental stress factors; rd29A and rd19B, which are genes of *Arabidopsis thaliana* that encode hydrophilic proteins which are induced in response to dehydration, low temperature, salt stress, or exposure to abscisic acid and enable the plant to tolerate the stress (Yamaguchi-Shinozaki et al., Plant Cell, 1994, 6: 251-264). Other genes contemplated can be found in U.S. Pat. Nos. 5,296,462 and 5,356,816.

Tissue-Specific Expression

In certain embodiments, lignocellulolytic enzyme expression is targeted to specific tissues of the transgenic plant. For example, tissue specific expression may be performed to preferentially express enzymes in leaves and stems rather than grain or seed (which can reduce concerns about human consumption of genetically modified organism (GMOs)). Tissue-specific expression has other benefits including targeted expression of enzyme(s) to the appropriate substrate.

Tissue specific expression may be functionally accomplished by introducing a constitutively expressed gene in combination with an antisense gene that is expressed only in those tissues where the gene product (e.g., lignocellulolytic enzyme) is not desired. For example, a gene coding for a lignocellulolytic enzyme may be introduced such that it is expression in all tissues using the 35S promoter from Cauliflower Mosaic Virus. Expression of an antisense transcript of the gene in maize kernel, using for example a zein promoter, would prevent accumulation of the lignocellulolytic enzyme in seed. Hence the enzyme encoded by the introduced gene would be present in all tissues except the kernel.

Moreover, several tissue-specific regulated genes and/or promoters have been reported in plants. Some reported tissue-specific genes include the genes encoding the seed storage proteins (such as napin, cruciferin, β-conglycinin, and phaseolin) zein or oil body proteins (such as oleosin), or genes involved in fatty acid biosynthesis (including acyl carrier protein, stearoyl-ACP desaturase, and fatty acid desaturases (fad 2-1)), and other genes expressed during embryo development, such as Bce4 (Kridl et al., Seed Science Research, 1991, 1: 209). Examples of tissue-specific promoters, which have been described include the lectin (Vodkin, Prog. Clin. Biol. Res., 1983, 138: 87; Lindstrom et al., Der. Genet., 1990, 11: 160), corn alcohol dehydrogenase 1 (Dennis et al., Nucleic Acids Res., 1984, 12: 983), corn light harvesting complex (Bansal et al., Proc. Natl. Acad. Sci. USA, 1992, 89: 3654), corn heat shock protein, pea small subunit RuBP carboxylase, Ti plasmid mannopine synthase, Ti plasmid nopaline synthase, petunia chalcone isomerase (van Tunen et al., EMBO J., 1988, 7:125), bean glycine rich protein 1 (Keller et al., Genes Dev., 1989, 3: 1639), truncated CaMV 35S (Odell et al., Nature, 1985, 313: 810), potato patatin (Wenzler et al., Plant Mol. Biol., 1989, 13: 347), root cell (Yamamoto et al., Nucleic Acids Res., 1990, 18: 7449), maize zein (Reina et al., Nucleic Acids Res., 1990, 18: 6425; Kriz et al., Mol. Gen. Genet., 1987, 207: 90; Wandelt et al., Nucleic Acids Res., 1989, 17 2354), PEPCase, R gene complex-associated promoters (Chandler et al., Plant Cell, 1989, 1: 1175), and chalcone synthase promoters (Franken et al., EMBO J., 1991, 10: 2605). Particularly useful for seed-specific expression is the pea vicilin promoter (Czako et al., Mol. Gen. Genet., 1992, 235: 33).

Cellular Specific Expression

In some embodiments, lignocellulolytic enzyme expression is targeted to specific cellular compartments or organelles, such as, for example, the cytosol, the vacuole, the nucleus, the endoplasmic reticulum, the mitochondria, the apoplast, the peroxisomes, or plastids. Directing the lignocellulolytic enzyme to a specific cell compartment or organelle will allow the enzyme to be localized such that it will not come into contact with the substrate during plant growth. The enzymatic action of the enzyme will not occur until the enzyme contacts its substrate, e.g., following physical disruption of the cell integrity by milling.

In particular, the present invention provides plants engineered to express one or more lignocellulolytic enzymes in the apoplast, the chloroplast and/or the vacuole. Targeting expression of a lignocellulolytic enzyme to the cell wall (as in the apoplast) can help overcome the difficulty of mixing hydrophobic cellulose and hydrophilic enzymes that makes it hard to achieve efficient hydrolysis with external enzymes.

The present invention provides plants engineered to express a lignocellulolytic enzyme (or several lignocellulolytic enzymes) at more than one cellular compartments or organelles. By using promoters targeted at different locations in the plant cell, one can increase the total enzyme produced in the plant. Thus, for example, using an apoplast promoter with the E1 gene, and a chloroplast promoter with the E1 gene, in a plant would increase total production of E1 compared to a single promoter/E1 construct in the plant. Furthermore, by using promoters targeted at different locations in the plant in the case of expression of multiple lignocellulolytic enzymes, one can minimize in vivo (pre-processing) deconstruction of the cell wall that occurs when multiple synergistic enzymes are present in a cell. For example, combining an endoglucanase with an apoplast promoter, a hemicellulase with a vacuole promoter, and an exoglucanase with a chloroplast promoter, sequesters each enzyme in a different part of the cell and achieves the advantages listed above. This method circumvents the limit on enzyme mass that can be expressed in a single organelle or location of the cell.

The localization of a nuclear-encoded protein (e.g., enzyme) within the cell is known to be determined by the amino acid sequence of the protein. The protein localization can be altered by modifying the nucleotide sequence that encodes the protein in such a manner as to alter the protein's amino acid sequence. The polynucleotide sequences encoding lignocellulolytic enzymes can be altered to redirect the cellular localization of the encoded enzymes by any suitable method (Dai et al., Trans. Res., 2005, 14: 627).

Expression Vectors

Nucleic acid constructs according to the present invention may be cloned into a vector, such as, for example, a plasmid. Vectors suitable for transforming plant cells include, but are not limited to, Ti plasmids from *Agrobacterium tumefaciens* (J. Darnell, H. F. Lodish and D. Baltimore, "*Molecular Cell Biology*", 2$^{nd}$ Ed., 1990, Scientific American Books: New York), a plasmid containing a β-glucuronidase gene and a cauliflower mosaic virus (CaMV) promoter plus a leader sequence from alfalfa mosaic virus (J. C. Sanford et al., Plant Mol. Biol. 1993, 22: 751-765) or a plasmid containing a bar gene cloned downstream from a CaMV 35S promoter and a tobacco mosaic virus (TMV) leader. Other plasmids may additionally contain introns, such as that derived from alcohol dehydrogenase (Adh1), or other DNA sequences. The size of the vector is not a limiting factor.

For constructs intended to be used in *Agrobacterium*-mediated transformation, the plasmid may contain an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction in plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of *Agrobacterium*, delimit the DNA region that will be transferred to the plant.

Methods of preparation of nucleic acid constructs and expression vectors are well known in the art and can be found described in several textbooks such as, for example, J. Sambrook, E. F. Fritsch and T. Maniatis, "*Molecular Cloning: A Laboratory Manual*", 1989, Cold Spring Harbor Laboratory: Cold Spring Harbor, and T. J. Silhavy, M. L. Berman, and L. W. Enquist, "*Experiments with Gene Fusions*", 1984, Cold Spring Harbor Laboratory: Cold Spring Harbor; F. M. Ausubel et al., "*Current Protocols in Molecular Biology*", 1989, John Wiley & Sons: New York.

Additional desirable properties of the transgenic plants may include, but are not limited to, ability to adapt for growth in various climates and soil conditions; well studied genetic model system; incorporation of bioconfinement features such as male (or total) sterile flowers; incorporation of phytoremediation features such as contaminant hyperaccumulation, greater biomass, or promotion of contaminant-degrading mycorrhizae.

V. Preparation of Transgenic Plants

Nucleic acid constructs, such as those described above, can be used to transform any plant including monocots and dicots. In some embodiments, plants are green field plants. In other embodiments, plants are grown specifically for "biomass energy" and/or phytoremediation. Examples of suitable plants for use in the methods of the present invention include, but are not limited to, corn, switchgrass, sorghum, miscanthus, sugarcane, poplar, pine, wheat, rice, soy, cotton, barley, turf grass, tobacco, bamboo, rape, sugar beet, sunflower, willow, and eucalyptus. Using transformation methods, genetically modified plants, plant cells, plant tissue, seeds, and the like can be obtained.

Transformation according to the present invention may be performed by any suitable method. In certain embodiments, transformation comprises steps of introducing a nucleic acid construct, as described above, into a plant cell or protoplast to obtain a stably transformed plant cell or protoplast; and regenerating a whole plant from the stably transformed plant cell or protoplast.

Cell Transformation

Delivery or introduction of a nucleic acid construct into eukaryotic cells may be accomplished using any of a variety of methods. The method used for the transformation is not critical to the instant invention. Suitable techniques include, but are not limited to, non-biological methods, such as microinjection, microprojectile bombardment, electroporation, induced uptake, and aerosol beam injection, as well as biological methods such as direct DNA uptake, liposomes and *Agrobacterium*-mediated transformation. Any combinations of the above methods that provide for efficient transformation of plant cells or protoplasts may also be used in the practice of the invention.

Methods of introduction of nucleic acid constructs into plant cells or protoplasts have been described. See, for example, "*Methods for Plant Molecular Biology*", Weissbach and Weissbach (Eds.), 1989, Academic Press, Inc; "*Plant Cell, Tissue and Organ Culture: Fundamental Methods*", 1995, Springer-Verlag: Berlin, Germany; and U.S. Pat. Nos. 4,945,050; 5,036,006; 5,100,792; 5,240,855; 5,302,523; 5,322,783; 5,324,646; 5,384,253; 5,464,765; 5,538,877; 5,538,880; 5,550,318; 5,563,055; and 5,591,616).

In particular, electroporation has frequently been used to transform plant cells (see, for example, U.S. Pat. No. 5,384,253). This method is generally performed using friable tissues (such as a suspension culture of cells or embryogenic callus) or target recipient cells from immature embryos or other organized tissue that have been rendered more susceptible to transformation by electroporation by exposing them to pectin-degrading enzymes or by mechanically wounding them in a controlled manner. Intact cells of maize (see, for example, K. D'Halluin et al., Plant cell, 1992, 4: 1495-1505; C. A. Rhodes et al., Methods Mol. Biol. 1995, 55: 121-131; and U.S. Pat. No. 5,384,253), wheat, tomato, soybean, and tobacco have been transformed by electroporation. As reviewed, for example, by G. W. Bates (Methods Mol. Biol. 1999, 111: 359-366), electroporation can also be used to transform protoplasts.

Another method of transformation is microprojectile bombardment (see, for example, U.S. Pat. Nos. 5,538,880; 5,550,318; and 5,610,042; and WO 94/09699). In this method, nucleic acids are delivered to living cells by coating or precipitating the nucleic acids onto a particle or microprojectile (for example tungsten, platinum or gold), and propelling the coated microprojectile into the living cell. Microprojectile bombardment techniques are widely applicable, and may be used to transform virtually any monocotyledonous or dicotyledonous plant species (see, for example, U.S. Pat. Nos. 5,036,006; 5,302,523; 5,322,783 and 5,563,055; WO 95/06128; A. Ritala et al., Plant Mol. Biol. 1994, 24: 317-325; L. A. Hengens et al., Plant Mol. Biol. 1993, 23: 643-669; L. A.

Hengens et al., Plant Mol. Biol. 1993, 22: 1101-1127; C. M. Buising and R. M. Benbow, Mol. Gen. Genet. 1994, 243: 71-81; C. Singsit et al., Transgenic Res. 1997, 6: 169-176).

The use of *Agrobacterium*-mediated transformation of plant cells is well known in the art (see, for example, U.S. Pat. No. 5,563,055). This method has long been used in the transformation of dicotyledonous plants, including *Arabidopsis* and tobacco, and has recently also become applicable to monocotyledonous plants, such as rice, wheat, barley and maize (see, for example, U.S. Pat. No. 5,591,616). In plant strains where *Agrobacterium*-mediated transformation is efficient, it is often the method of choice because of the facile and defined nature of the gene transfer. *Agrobacterium*-mediated transformation of plant cells is carried out in two phases. First, the steps of cloning and DNA modifications are performed in *E. coli*, and then the plasmid containing the gene construct of interest is transferred by heat shock treatment into *Agrobacterium*, and the resulting *Agrobacterium* strain is used to transform plant cells.

Transformation of plant protoplasts can be achieved using methods based on calcium phosphate precipitation, polyethylene glycol treatment, electroporation, and combinations of these treatments (see, e.g., I. Potrykus et al., Mol. Gen. Genet. 1985, 199: 169-177; M. E. Fromm et al., Nature, 1986, 31: 791-793; J. Callis et al., Genes Dev. 1987, 1: 1183-1200; S. Omirulleh et al., Plant Mol. Biol. 1993, 21: 415-428).

Alternative methods of plant cell transformation, which have been reviewed, for example, by M. Rakoczy-Trojanowska (Cell Mol. Biol. Lett. 2002, 7: 849-858), can also be used in the practice of the present invention.

The successful delivery of the nucleic acid construct into the host plant cell or protoplast may be preliminarily evaluated visually. Selection of stably transformed plant cells can be performed, for example, by introducing into the cell, a nucleic acid construct comprising a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Examples of herbicides which may be used include phosphinothricin and glyphosate. Potentially transformed cells then are exposed to the selective agent. Cells where the resistance-conferring gene has been integrated and expressed at sufficient levels to permit cell survival will generally be present in the population of surviving cells.

Alternatively, host cells comprising a nucleic acid sequence of the invention and which express its gene product may be identified and selected by a variety of procedures, including, DNA-DNA or DNA-RNA hybridization and protein bioassay or immunoassay techniques such as membrane, solution or chip-based technologies for the detection and/or quantification of nucleic acid or protein.

Plant cells are available from a wide range of sources including the American Type Culture Collection (Rockland, Md.), or from any of a number of seed companies including, for example, A. Atlee Burpee Seed Co. (Warminster, Pa.), Park Seed Co. (Greenwood, S.C.), Johnny Seed Co. (Albion, Me.), or Northrup King Seeds (Hartsville, S.C.). Descriptions and sources of useful host cells are also found in I. K. Vasil, "*Cell Culture and Somatic Cell Genetics of Plants*", Vol. I, II and II; 1984, Laboratory Procedures and Their Applications Academic Press: New York; R. A. Dixon et al., "*Plant Cell Culture—A Practical Approach*", 1985, IRL Press: Oxford University; and Green et al., "Plant Tissue and Cell Culture", 1987, Academic Press: New York.

Plant cells or protoplasts stably transformed according to the present invention are provided herein.

Plant Regeneration

In plants, every cell is capable of regenerating into a mature plant, and in addition contributing to the germ line such that subsequent generations of the plant will contain the transgene of interest. Stably transformed cells may be grown into plants according to conventional ways (see, for example, McCormick et al., Plant Cell Reports, 1986, 5: 81-84). Plant regeneration from cultured protoplasts has been described, for example by Evans et al., "*Handbook of Plant Cell Cultures*", Vol. 1, 1983, MacMilan Publishing Co: New York; and I. R. Vasil (Ed.), "*Cell Culture and Somatic Cell Genetics of Plants*", Vol. I (1984) and Vol. II (1986), Acad. Press: Orlando.

Means for regeneration vary from species to species of plants, but generally a suspension of transformed protoplasts or a Petri plate containing transformed explants is first provided. Callus tissue is formed and shoots may be induced from callus and subsequently roots. Alternatively, somatic embryo formation can be induced in the callus tissue. These somatic embryos germinate as natural embryos to form plants. The culture media will generally contain various amino acids and plant hormones, such as auxin and cytokinins. Glutamic acid and proline may also be added to the medium. Efficient regeneration generally depends on the medium, on the genotype, and on the history of the culture.

Regeneration from transformed individual cells to obtain transgenic whole plants has been shown to be possible for a large number of plants. For example, regeneration has been demonstrated for dicots (such as apple; *Malus pumila*; blackberry, *Rubus*; Blackberry/raspberry hybrid, *Rubus*; red raspberry, *Rubus*; carrot; *Daucus carota*; cauliflower; *Brassica oleracea*; celery; *Apium graveolens*; cucumber; *Cucumis sativus*; eggplant; *solanum melongena*; lettuce; *Lactuca sativa*; potato; *Solanum tuberosum*; rape; *Brassica napus*; soybean (wild); Glycine Canescens; strawberry; *Fragaria* x *ananassa*; tomato; *Lycopersicon esculentum*; walnut; *Juglans regia*; melon; *Cucumis melo*; grape; *Vitis vinifera*; mango; and *Mangifera indica*) as well as for monocots (such as rice; *Oryza sativa*; rye, *Secale cereale*; and Maize).

Primary transgenic plants may then be grown using conventional methods. Various techniques for plant cultivation are well known in the art. Plants can be grown in soil, or alternatively can be grown hydroponically (see, for example, U.S. Pat. Nos. 5,364,451; 5,393,426; and 5,785,735). Primary transgenic plants may be either pollinated with the same transformed strain or with a different strain and the resulting hybrid having the desired phenotypic characteristics identified and selected. Two or more generations may be grown to ensure that the subject phenotypic characteristics is stably maintained and inherited and then seeds are harvested to ensure that the desired phenotype or other property has been achieved.

As is well known in the art, plants may be grown in different media such as soil, growth solution or water.

Selection of plants that have been transformed with the construct may be performed by any suitable method, for example, with Northern blot, Southern blot, herbicide resistance screening, antibiotic resistance screening or any combinations of these or other methods. The Southern blot and Northern blot techniques, which test for the presence (in a plant tissue) of a nucleic acid sequence of interest and of its corresponding RNA, respectively, are standard methods (see, for example, Sambrook & Russell, "*Molecular Cloning*", 2001, Cold Spring Harbor Laboratory Press: Cold Spring Harbor).

VI. Uses of Inventive Transgenic Plants

The transgenic plants and plant parts disclosed herein may be used advantageously in a variety of applications. More specifically, the present invention, which involves genetically engineering plants for both increased biomass and expression of lignocellulolytic enzymes, results in downstream process innovations and/or improvements in a variety of applications including ethanol production, phytoremediation and hydrogen production.

A—Ethanol Production

Plants transformed according to the present invention provide a means of increasing ethanol yields, reducing pretreatment costs, by reducing acid/heat pretreatment requirements for saccharification of biomass; and/or reducing other plant production and processing costs, such as by allowing multi-applications and isolation of commercially valuable by-products.

Plant Culture. As already mentioned above, farmers can grow different transgenic plants of the present invention (e.g., different variety of transgenic corn, each expressing a lignocellulolytic enzyme or a combination of enzymes) simultaneously, achieving the desired "blend" of enzymes produced by changing the seed ratio.

Plant Harvest. Transgenic plants of the present invention can be harvested as known in the art. For example, current techniques may cut corn stover at the same time as the grain is harvested, but leave the stover lying in the field for later collection. However, dirt collected by the stover can interfere with ethanol production from lignocellulosic material. The present invention provides a method in which transgenic plants are cut, collected, stored, and transported so as to minimize soil contact. In addition to minimizing interference from dirt with ethanol production, this method can result in reduction in harvest and transportation costs.

Pretreatment. Conventional methods include physical, chemical, and/or biological pretreatments. For example, physical pretreatment techniques can include one or more of various types of milling, crushing, irradiation, steaming/steam explosion, and hydrothermolysis. Chemical pretreatment techniques can include acid, alkaline, organic solvent, ammonia, sulfur dioxide, carbon dioxide, and pH-controlled hydrothermolysis. Biological pretreatment techniques can involve applying lignin-solubilizing microorganisms (T.-A. Hsu, "*Handbook on Bioethanol. Production and Utilization*", C. E. Wyman (Ed.), 1996, Taylor & Francis: Washington, D.C., 179-212; P. Ghosh and A. Singh, A., Adv. Appl. Microbiol., 1993, 39: 295-333; J. D. McMillan, in "*Enzymatic Conversion of Biomass for Fuels Production*", M. Himmel et al., (Eds.), 1994, Chapter 15, ACS Symposium Series 566, American Chemical Society: B. Hahn-Hagerdal, Enz. Microb. Tech., 1996, 18: 312-331; and L. Vallander and K. E. L. Eriksson, Adv. Biochem. Eng./Biotechnol., 1990, 42: 63-95). The purpose of the pretreatment step is to break down the lignin and carbohydrate structure to make the cellulose fraction accessible to cellulolytic enzymes.

Simultaneous use of transgenic plants that express one or more cellulases, one or more hemicellulases and/or one or more ligninases according to the present invention reduces or eliminates expensive grinding of the biomass, reduces or eliminates the need for heat and strong acid required to strip lignin and hemicellulose away from cellulose before hydrolyzing the cellulose. Therefore, the present invention provides improvements over existing pretreatment methods. Such improvements may include one or more of: reduction of biomass grinding, elimination of biomass grinding, reduction of the pretreatment temperature, elimination of heat in the pretreatment, reduction of the strength of acid in the pretreatment step, elimination of acid in the pretreatment step, and any combination thereof.

In certain embodiments, the pretreated material is used for saccharification without further manipulation. In other embodiments, it may be desired to process the plant tissue so as to produce an extract comprising the lignocellulolytic enzyme(s). In this case, the extraction is carried out in the presence of components known in the art to favor extraction of active enzymes from plant tissue and/or to enhance the degradation of cell-wall polysaccharides in the lignocellulosic biomass. Such components include, but are not limited to, salts, chelators, detergents, antioxidants, polyvinylpyrrolidone (PVP), and polyvinylpolypyrrolidone (PVPP). The remaining plant tissue may then be submitted to a pretreatment process.

Saccharification. In saccharification (or enzymatic hydrolysis), lignocellulose is converted into fermentable sugars by lignocellulolytic enzymes present in the pretreated material. If desired, external cellulolytic enzymes (i.e., enzymes not produced by the transgenic plants being processed) may be added to this mixture. Extracts comprising lignocellulolytic enzymes obtained as described above can be added back to the lignocellulosic biomass before saccharification. Here again, external cellulolytic enzymes may be added to the saccharification reaction mixture.

Saccharification is generally performed in stirred-tank reactors or fermentors under controlled pH, temperature, and mixing conditions. A saccharification step may last up to 200 hours. Saccharification may be carried out at temperatures from about 30° C. to about 65° C., in particular around 50° C., and at a pH in the range of between about 4 and about 5, in particular, around pH 4.5. Saccharification can be performed on the whole pretreated material.

The present Applicants have shown that adding cellulases to E1-transformed plants increases total glucose production compared to adding cellulases to non-transgenic plants, which suggests that simply using transgenic E1 plants with current external cellulase techniques can substantially increase ethanol yields. The experiment also indicates that adding cellulases to E1 plants increases total glucose production compared to adding cellulases to non-transgenic plants. This is an important result since it suggests that simply using transgenic E1 plants with current external cellulase techniques can substantially increase ethanol yields in the presence or absence of pretreatment processes.

Fermentation. In the fermentation step, sugars, released from the lignocellulose as a result of the pretreatment and enzymatic hydrolysis steps, are fermented to one or more organic substances, e.g., ethanol, by a fermenting microorganism, such as yeasts and/or bacteria. The fermentation can also be carried out simultaneously with the enzymatic hydrolysis in the same vessels, again under controlled pH, temperature and mixing conditions. When saccharification and fermentation are performed simultaneously in the same vessel, the process is generally termed simultaneous saccharification and fermentation or SSF.

Fermenting microorganisms and methods for their use in ethanol production are known in the art (Sheehan, "The road to Bioethanol: A strategic Perspective of the US Department of Energy's National Ethanol Program" In: "*Glucosyl Hydrolases For Biomass Conversion*", ACS Symposium Series 769, 2001, American Chemical Society: Washington, D.C.). Existing ethanol production methods that utilize corn grain as the biomass typically involve the use of yeast, particularly strains of *Saccharomyces cerevisiae*. Such strains can be utilized in the methods of the invention. While such strains may be preferred for the production of ethanol from glucose that is derived from the degradation of cellulose and/or starch, the methods of the present invention do not depend on the use of a particular microorganism, or of a strain thereof, or of any particular combination of said microorganisms and said strains.

Yeast or other microorganisms are typically added to the hydrolysate and the fermentation is allowed to proceed for 24-96 hours, such as 35-60 hours. The temperature of fermentation is typically between 26-40° C., such as 32° C., and at a pH between 3 and 6, such as about pH 4-5.

A fermentation stimulator may be used to further improve the fermentation process, in particular, the performance of the fermenting microorganism, such as, rate enhancement and ethanol yield. Fermentation stimulators for growth include vitamins and minerals. Examples of vitamins include multivitamin, biotin, pantothenate, nicotinic acid, meso-inositol, thiamine, pyridoxine, para-aminobenzoic acid, folic acid, riboflavin, and vitamins A, B, C, D, and E (Alfenore et al., "Improving ethanol production and viability of *Saccharomyces cerevisiae* by a vitamin feeding strategy during fed-batch process", 2002, Springer-Verlag). Examples of minerals include minerals and mineral salts that can supply nutrients comprising phosphate, potassium, manganese, sulfur, calcium, iron, zinc, magnesium and copper.

Recovery. Following fermentation (or SSF), the mash is distilled to extract the ethanol. Ethanol with a purity greater than 96 vol. % can be obtained.

By-Products. The hydrolysis process of lignocellulosic raw material also releases by-products such as weak acids, furans, and phenolic compounds, which are inhibitory to the fermentation process. Removing such by-products may enhance fermentation. In particular, lignin and lignin breakdown products such as phenols, produced by enzymatic activity and by other processing activities, from the saccharified cellulosic biomass is likely to be important to speeding up fermentation and maintaining optimum viscosity.

Thus, in another aspect, the present invention provides methods of speeding up fermentation which comprise removing, from the hydrolysate, products of the enzymatic process that cannot be fermented. Such products comprise, but are not limited to, lignin, lignin breakdown products, phenols, and furans. In certain embodiments, products of the enzymatic process that cannot be fermented can be separated and used subsequently. For example, the products can be burned to provide heat required in some steps of the ethanol production such as saccharification, fermentation, and ethanol distillation, thereby reducing costs by reducing the need for current external energy sources such as natural gas. Alternatively, such by-products may have commercial value. For example, phenols can find applications as chemical intermediates for a wide variety of applications, ranging from plastics to pharmaceuticals and agricultural chemicals. Phenol condensed to with aldehydes (e.g., methanal) make resinous compounds, which are the basis of plastics which are used in electrical equipment and as bonding agents in manufacturing wood products such as plywood and medium density fiberboard (MDF).

Separation of by-products from the hydrolysate can be done using a variety of chemical and physical techniques that rely on the different chemical and physical properties of the by-products (e.g., lignin and phenols). Such techniques include, but are not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, distillation, or extraction.

Some of the hydrolysis by-products, such as phenols, or fermentation/processing products, such as methanol, can be used as ethanol denaturants. Currently about 5% gasoline is added immediately to distilled ethanol as a denaturant under the Bureau of Alcohol, Tobacco and Firearms regulations, to prevent unauthorized non-fuel use. This requires shipping gasoline to the ethanol production plant, then shipping the gas back with the ethanol to the refinery. The gas also impedes the use of ethanol-optimized engines that make use of ethanol's higher compression ratio and higher octane to improve performance. Using transgenic plant derived phenols and/or methanol as denaturants in lieu of gasoline can reduce costs and increase automotive engine design alternatives.

Reducing Lignin Content. Another way of reducing lignin and lignin breakdown products that are not fermentable in hydrolysate is to reduce lignin content in transgenic plant of the present invention. Such methods have been developed and can be used to modify the inventive plants (see, for example, U.S. Pat. Nos. 6,441,272 and 6,969,784, U.S. Pat. Appln. No. 2003-0172395, US and PCT publication No. WO 00/71670).

Combined Starch Hydrolysis and Cellulolytic Material Hydrolysis. The transgenic plants and plant parts disclosed herein can be used in methods involving combined hydrolysis of starch and of cellulosic material for increased ethanol yields. In addition to providing enhanced yields of ethanol, these methods can be performed in existing starch-based ethanol processing facilities.

Starch is a glucose polymer that is easily hydrolyzed to individual glucose molecules for fermentation. Starch hydrolysis may be performed in the presence of an amylolytic microorganism or enzymes such as amylase enzymes. In certain embodiments of the invention, starch hydrolysis is performed in the presence of at least one amylase enzyme. Examples of suitable amylase enzymes include $\alpha$-amylase (which randomly cleaves the $\alpha(1\text{-}4)$glycosidic linkages of amylose to yield dextrin, maltose or glucose molecules) and glucoamylase (which cleaves the $\alpha(1\text{-}4)$ and $\alpha(1\text{-}6)$glycosidic linkages of amylose and amylopectin to yield glucose).

In the inventive methods, hydrolysis of starch and hydrolysis of cellulosic material can be performed simultaneously (i.e., at the same time) under identical conditions (e.g., under conditions commonly used for starch hydrolysis). Alternatively, the hydrolytic reactions can be performed sequentially (e.g., hydrolysis of lignocellulose can be performed prior to hydrolysis of starch). When starch and cellulosic material are hydrolyzed simultaneously, the conditions are preferably selected to promote starch degradation and to activate lignocellulolytic enzyme(s) for the degradation of lignocellulose. Factors that can be varied to optimize such conditions include physical processing of the plants or plant parts, and reaction conditions such as pH, temperature, viscosity, processing times, and addition of amylase enzymes for starch hydrolysis.

The inventive methods may use transgenic plants (or plant parts) alone or a mixture of non-transgenic plants (or plant parts) and plants (or plant parts) transformed according to the present invention. Suitable plants include any plants that can be employed in starch-based ethanol production (e.g., corn, wheat, potato, cassaya, etc). For example, the present inventive methods may be used to increase ethanol yields from corn grains.

B—Phytoremediation

As already mentioned above, transgenic plants of the present invention which are genetically transformed for both expression of lignocellulolytic enzymes and increased biomass can be used simultaneously for bioenergy production and phytoremediation.

High biomass yields sought for bioenergy are also desirable in phytoremediation of metals, metalloids and radionuclides, because the rate of contaminant removal is a function of biomass as well as bioconcentration (the ratio of contaminant in the plants to contaminant in the soil). In addition, new ways of disposing of contaminated biomass are sought that minimize landfill burdens. Current treatment methods can remove 60-90% of recovered metals from plant biomass (Edenspace, unpublished data), which for some contaminants is insufficient to allow disposal of the treated biomass as nonhazardous waste. Metals are typically sequestered inside cell walls, which are difficult to break down cost-effectively using current techniques. Cellulose in primary and secondary cell walls typically accounts for 35 to 50% of plant dry weight (B. B. Buchanan et al., "Biochemistry & Molecular Biology of Plants, American Society of Plant Physiologists", 2000, Rockville, Md.).

The ability to degrade cell walls with low-cost cellulase can significantly improve the current state of the art in contaminant recovery from phytoremediation crops, allowing treatment of contaminated biomass to reduce the costs and liabilities associated with landfill disposal, enable the recycling of recovered metals, while producing clean, marketable feedstocks for bioenergy. Importantly, the marginal cost of producing cellulase and hydrolyzed bioenergy feedstocks according to the present invention can be quite low, because most of the biomass production and treatment costs would be borne by the phytoremediation project. The need to cover crop growing costs and provide a farmer with a profit of $150 to $200 an acre, while a significant cost challenge for dedicated biofuels crops (B. S. Hooker et al., in "*Glycosyl Hydrolases for Biomass Conversion*", ACS Symposium Series, 2001, 769: 55-90), represents only a tiny fraction of typical environmental remediation budgets of $10,000 or more per acre (D. J. Glass, U.S. and International Markets for Phytoremediation, 1999-2000, 1999, pp. 112-114).

As reported in the Examples section below, the present Applicants have demonstrated acceptable phytoremediation performance of E1 tobacco, including increased post-harvest recovery of metals from plant biomass and normal cellulase activity of material with heavy metals.

C—Hydrogen Production

A February 2002 report by the National Renewable Energy Laboratory on hydrogen production from biomass indicates that for the near- to mid-term, generation of hydrogen from biomass is more practicable than from other renewable-based processes such as solar- or wind-driven electrolysis or photobiological water splitting (T. A. Milne et al., Hydrogen from biomass: state of the art and research challenges. National Renewable Energy Lab, Technical Report IEA/H2—TR-02/001, Feb. 1, 2002). The report also observes that hydrogen production from biomass is currently not economically competitive with natural gas steam reforming for stand-alone hydrogen, in part because of the relatively low energy content and high oxygen content of biomass, and suggests that a focus of future research should be the identification and development of co-production opportunities, since multiple products improve production economics by providing additional sources of revenue while sharing costs. A 2004 report by the National Research Council also notes the importance of potential co-production opportunities, as well as the desirability of finding ways to use crop residue such as corn stover as feedstock, in order to reduce costs of hydrogen production from plant biomass (National Research Council. The hydrogen economy: Opportunities, costs, barriers, and R&D needs, 2004, National Academies Press, Washington, D.C., 101-103). In 2004, the Advisory Committee updated its recommended research plan, recommending specifically that the U.S. Department of Energy and U.S. Department of Agriculture significantly increase funding for cellulosic R&D programs (Biomass Research and Development Technical Advisory Committee (BRDTAC), Summary Statement and Recommendations, July 2004).

Accordingly, in another aspect, the present invention provides for using transgenic plants transformed for both expression of lignocellulolytic enzymes and increased biomass in production of biomass-based hydrogen. For example, the biomass produced by large-scale phytoremediation projects, as well as from switchgrass and other "barrier strip" crops widely used to reduce fertilizer runoff, can be a significant source of low-cost cellulase and bioenergy feedstock to producers of biomass-based hydrogen. By sharing biomass production and post-harvest treatment costs with phytoremediation, costs for producing hydrolyzed feedstocks for biofuels can be dramatically reduced, an important step toward increasing the cost-competitiveness of hydrogen fuel

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Some of the results reported in this section have been presented in manuscripts that have recently been accepted for publication (H. Salehi et al., "Delay in flowering and increase in biomass of plants expressing the *Arabidopsis* floral repressor gene FLC (FLOWERING LOCUS C)", J. Plant Physiol., 2005, 162: 711-717; and H. Salehi et al., "Expression of flowering locus C in an *Acidothermus cellulolyticus* endo-1, 4-β-D-glucanase (E1) transgenic tobacco (*Nicotiana tobacum* L.) and its effect on delay in flowering and increase in biomass", In Vitro Cellular and Developmental Biology—PLANT, 2005). Each of these manuscripts is incorporated herein by reference in its entirety.

Example 1

Generation of Transgenic Tobacco

To generate the transgenic tobacco, wild-type tobacco was transformed with the E1 and then AtFLC genes using *Agrobacterium tumefaciens* as described below.

Description of the Donor. The endo-1,4-β-glucanase E1 gene (GenBank Accession No. U33212) was isolated from the thermophilic bacterium *Acidothermus cellulolyticus*. This bacterium was originally isolated from decaying wood in an acidic, thermal pool at Yellowstone National Park and deposited with the American Type Culture Collection (ATCC, Manassas, Va.) under collection number 43068 (A. Mohagheghi et al., Int. J. System. Baceril., 1986, 36: 435-443; Tucker et al., Biotechnology, 1989, 7: 817-820). As already mentioned herein, the bacterium has been characterized with the ability to hydrolyze and degrade plant cellulose.

For transformation into tobacco, the E1 catalytic domain was isolated from the genomic sequence and contained bp 950-2020 listed in Accession No. U33212. To generate the E1-catalytic construct, a stop codon was introduced after the codon specifying Val-358 of E1 through Polymerase Chain Reaction (PCR), and the 5' end of the gene was fused to the 21 amino acids in the amino-terminal soybean vegetative storage protein VSPβ (GenBank Accession No. M76980) (Ziegelhoffer et al., Mol. Breed, 2001, 8: 147-158) in order to target the protein to the apoplast. For cloning purposes, a SacI site was added to the 3' end of the E1 gene following the stop codon and an XbaI site at the 5' end of the VSPβ sequence.

The inhibitor Flowering Locus C gene, or FLC (accession # BK000546) is a dosage-dependent repressor of flowering in Arabidopsis (S. D. Michaels and R. M. Amasino, Plant Cell, 1999, 11: 949-956), which operates by negatively regulating the expression of genes that promote flowering, such as SOC1 and FT. The 591 bp cDNA was isolated from Arabidopsis and used without modification for transformation into tobacco.

Description of the Recipient. The recipient organism was Nicotiana tabacum W38, a commonly used variety for laboratory studies. Tobacco is a very well characterized crop that has been cultivated for centuries.

Figure 2:
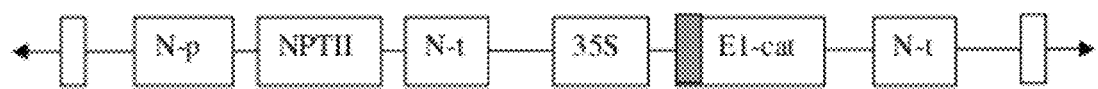
FIG. 2 is a map of the pBI121-E1 vector in between the right and left border sequences used in the transformation of tobacco as reported in Example 1. The E1 construct contains the VSPβ signal peptide fused to the N-terminus of the E1 catalytic domain. The following sequences are abbreviated; NOS promoter (N-p), neomycin phospho-transferase II (NPTII), NOS terminator (N-t), cauliflower mosaic virus 35S promoter (35S), β-glucuronidase (GUS), agrobacteria right border sequence (RB), left border (LB).

Description of the Vector and the Transformation Process. The E1 transformation vector was constructed from an existing pBI121 binary Ti vector used for agrobacteria mediated transformation (Jefferson et al., EMBO J., 1987, 6: 3901). Through standard agrobacteria transformation, DNA sequences in between the right and left borders are stably transferred into the plant genome. The complete sequence of pBI121 is 14,758 bp (GenBank Accession No. AF502128) and contains resistance to the antibiotic kanamycin and the GUS gene in between its right and left border sequence (as presented on FIG. 1). For the development of pBI121-E1, the β-glucuronidase gene was excised through digestion with XbaI and SacI and replaced with the VSPβ/E1 construct (as shown on FIG. 2).

Tobacco leaf explants were transformed with pBI121-E1 according to standard procedures (Horsch et al., Science, 1985, 227: 1229). Leaf explants were taken from the second and third fully expanded leaves of 3-week old in vitro shoot cultures of Nicotiana tabacum W38 maintained on MS medium. After pre-culture, explants were dropped into a suspension of Agrobacterium cells containing the modified pBI121 vector obtained from an overnight culture. Leaf pieces were selected on 100 mg/L kanamycin and plantlets (typically 2 or 3) developed 10-14 days later from callus formed along cut leaf edges. Plantlets were excised and rooted on MS media containing 100 mg/L kanamycin in Magenta GA7 boxes (Ziegelhoffer et al., Mol. Breed, 2001, 8: 147-158).

Transformed plants were confirmed through genomic PCR amplification of the E1 gene in parallel with measuring the hydrolysis of cellulose using leaf extracts (Ziegelhoffer et al., Mol. Breed, 2001, 8: 147-158). Plants positive for both the presence of the E1 gene and E1 activity were grown to maturity and seeds were collected for further work. Stable expression of the E1 gene and E1 activity were observed for multiple generations of tobacco after the transformation event.

Figure 3:
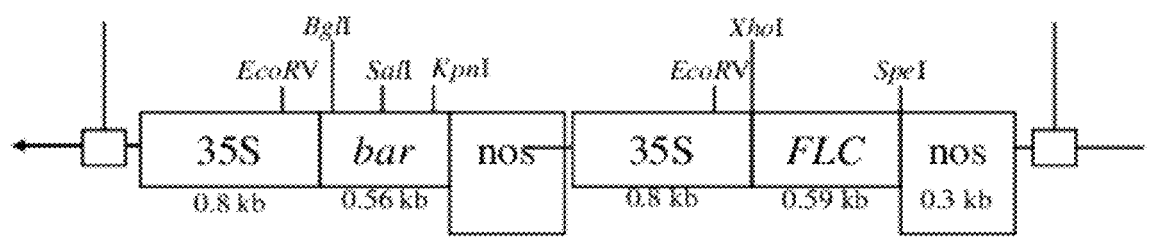
FIG. 3 shows a map pGreen. The construct contains two cassettes: (1) the *Arabidopsis* FLOWERING C (FLC) coding sequences regulated by CaMV 35S promoter (35S) and polyadenylation signal of nopaline synthase (nos) terminator, and (2) the phosphinothricin acetyltransferase coding region (bar) herbicide resistance selectable marker gene regulated by 35S promoter and nos terminator.

The AtFLC cDNA was isolated from and subcloned into the pGreen vector under the control of the Cauliflower Mosaic Viral 35S promoter (see FIG. 3) to transform E1 tobacco. The pGreen vector also contains the bar gene (phosphinothricin acetyltransferase coding region) for selection of the herbicide Basta in transformed plants in between the left and right border sequences. In order to increase the biomass of tobacco, and to delay flowering time as a method of preventing transfer of transgenic pollens to other field crops, AtFLC was transformed into the T4 generation of E1 tobacco developed above by the same method. Transformed plants were selected with 5 mg/L glufosinate ammonium, then confirmed with genomic PCR and RNA-blot analysis to measure the expression level of AtFLC. Seeds were collected from the line with the strongest phenotype and bulked up for use.

Presence of E1 gene. To verify the presence of the E1 gene, the third or fourth leaf from the shoot apex can be used for protein extraction. Leaf samples can be harvested at 2-3 hours into the light period. Leaf tissues can be cut into approximately 1 $cm^2$ pieces and pooled for homogenization. An enzyme assay, SDS-PAGE, and western blot can be carried out as described previously (Z. Dai et al., Transgenic Res., 2000, 9: 43-54).

E1 Activity. To assess E1 activity, the third or fourth leaf from the shoot apex of transgenic plants can be harvested. One half of the leaf tissues can be sliced into 1 cm×2 cm pieces and the other half used for direct extraction as described above. About 0.15 g of leaf pieces can be vacuum-infiltrated with 50 mM MES (pH 5.5) twice each for 10 minutes at 20 in. of mercury. The infiltrated leaf pieces can be transferred into 1.5 mL microcentrifuge tubes and centrifuged at 350 g for 10 minutes to obtain fluid from the intercellular space. About 15-25 μL of intercellular fluid can be used for E1 activity measurement and 30-50 μL of intercellular fluid can be used for protein quantification.

Example 2

Enzymatic Performance and Stability of E1 Tobacco

The stability properties of leaf protein concentrates and associated E1 cellulase activity in E1-FLC transgenic tobacco were characterized.

Figure 16:
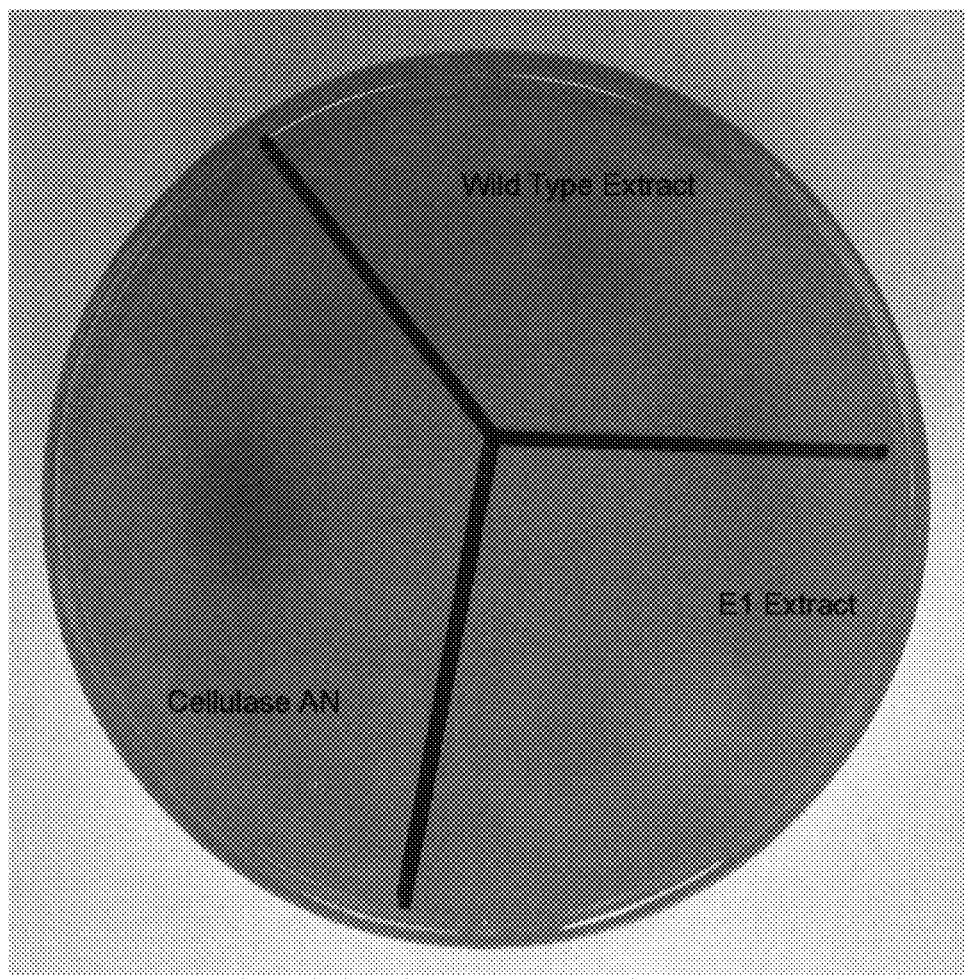
FIG. 16 shows the cellulase activity of crude extract from transgenic tobacco expressing E1. The red carboxy-methylcellulose in the Petri dish has been hydrolyzed by the application of E1 extract or commercially available cellulase enzymes (Cellulase AN, BIO-CAT) to form clear areas. No cellulase activity was observed from wild type tobacco extract.

Leaf protein concentrates were prepared by macerating the tobacco leaves with ice in a blender at a ratio of 8:1 (w/1). Samples of these extracts were analyzed for cellulase activity using carboxy-methyl cellulose. As shown in FIG. 16, extract from E1 plants but not wild-type tobacco can hydrolyze cellulase. Samples of these concentrates were also subjected to various conditions to determine the effect of refrigeration at 2° C., pre-heating the sample at 90° C., acidification to pH 4.0 with lactic acid, and drying the plant material prior to addition to external cellulase (Spezyme CP from Genencor International, Inc., Palo Alto, Calif.). Nine combinations of these variables were studied in the presence and absence of added cellulase (25 μL cellulase per mL).

The stability/activity of the cellulase enzymes (both added/external and endogenous) within these concentrates were measured as a function of the hydrolysis of cellulose and glucose production. One (1) mL aliquots of each sample were added to 0.25 g of microcrystalline cellulose. The solution was brought to 10 mL in a pH 4.5 citrate buffer. The solutions were allowed to hydrolyze for 5 days, and the concentration of glucose was measured to assess cellulase activity of the sample. Long-term studies are underway to determine cellulase activity measurements for various times for up to 6 months. Hydrolysis of cellulose as a function of glucose concentration in the samples is presented in Table 1. Table 1 presents the concentrations of glucose (g/L) from transgenic and non-transgenic tobacco after five (5) days of hydrolysis. These results show that E1 tobacco can self-hydrolyze and that exogenous cellulose is more efficient with E1 tobacco.

TABLE 1

| | | | | Tobacco Genotype and Treatment | | | |
|---|---|---|---|---|---|---|---|
| | | | | No Added Cellulase | | Added Cellulase | |
| Pretreatment | | | | Control | E1/FLC | Control | E1/FLC |
| 2° C. | 90° C. | pH 4.0 | Dry | glucose (g/L) | | | |
| | | | | 0 | 0 | 3.13 | 3.72 |
| x | | | | 0 | 1.43 | 3.11 | 4.19 |
| | x | | | 0 | 0 | 3.44 | 4.50 |
| x | x | | | 0 | 0 | 3.08 | 5.74 |
| | | x | | 0 | 0 | 1.33 | 0.57 |

TABLE 1-continued

| | Pretreatment | | | Tobacco Genotype and Treatment | | | |
|---|---|---|---|---|---|---|---|
| | | | | No Added Cellulase | | Added Cellulase | |
| | | | | Control | E1/FLC | Control | E1/FLC |
| 2° C. | 90° C. | pH 4.0 | Dry | glucose (g/L) | | | |
| x | | x | | 0 | 0 | 1.65 | 0.79 |
| x | x | x | | 0 | 0.40 | 0.82 | 1.57 |
| | | | x | 0 | 0.34 | 4.08 | 5.58 |
| | x | | x | 0 | 0 | 4.84 | 4.92 |

As is evident from Table 1, the addition of acid severely limits the activity of cellulase, which is greatest at about pH 4.9. Significantly, in all cases except those involving acid addition, the transgenic plant plus cellulase experiments produced more glucose that the control plus cellulase. This is strong evidence for the expression of cellulase activity in the transgenic tobacco. Some transgenic samples showed measurable glucose production even without added cellulase, whereas none of the controls showed such cellulase activity. Bacterial growth was seen in all room temperature acidified samples after only two weeks, and some growth was seen in one refrigerated sample after one month. As such, room temperature acidified storage is clearly unsuitable for long-term storage conditions.

This experiment indicates that E1 cellulase activity in a concentrate of E1 plants is quite stable, suggesting that the plant juice can be used as a source of cellulase to hydrolyze non-transgenic plant biomass, or added back to the transgenic plants themselves after pre-processing steps such as high heat or acid treatment are completed that might otherwise inactivate the enzyme. The experiment also indicates that adding cellulases to E1 plants increases total glucose production compared to adding cellulases to non-transgenic plants. This is an important result since it suggests that simply using transgenic E1 plants with current external cellulase techniques can substantially increase ethanol yields.

As mentioned above, the "cellulase" enzyme system is complex and comprises various activities, while the transgenic E1 tobacco plant only expresses one of these activities, namely the endoglucanase. Three samples in the experiment described above showed glucose event in the absence of a complex cellulose complex, which is an encouraging result.

Figure 4:
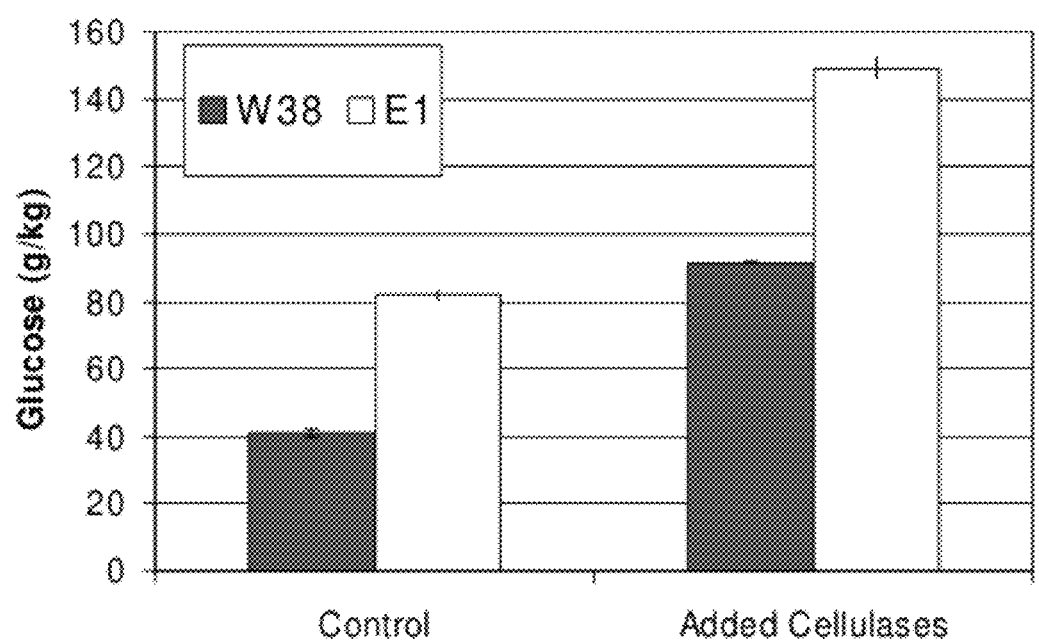
FIG. 4 is a graph showing glucose production from dried E1-FLC and W38 (wild-type) tobacco biomass equilibrated in citrate buffer (pH 4.5) for 24 hours at 50° C. with or without added Cellulase AN, glucoamylase, and hemicellulase. Error bars indicate ±1 standard deviation (n=3).

Adding additional members of the cellulase complex would be expected to increase hydrolysis of the E1 tobacco biomass. To test this hypothesis, an endoglucanase, glucoamylase and hemicellulase (obtained from BIO-CAT, Troy, Va.) were added to a non-transgenic tobacco and to an E1-FLC tobacco. As shown in FIG. 4, the results indicate that adding different enzyme types almost doubles glucose production in the transgenic tobacco, without chemical pre-treatment. The E1-FLC tobacco was also found to produce a higher level of glucose than the E1-only tobacco used in the previous experiment.

This result suggest that creating additional plant genotypes expressing different members of the cellulase complex, such as ligninase and hemicellulase, could multiply the hydrolysis yield of E1 plants. The result also suggests that the E1 activity is not restricted to that of an endoglucanase. The increased production of glucose in the absence of external cellulases indicates that additional enzymatic hydrolysis of polysaccharides and disaccharides is occurring in a manner similar to that observed with exoglucanases, indicating that E1 may be what has been termed a "processive" endoglucanase.

Example 3

Phytoremediation Performance of E1 Tobacco

The present Applicants have previously demonstrated the use of tobacco in the phytoremediation of metals such as lead and uranium (Edenspace Systems Corporation, 2002, USEPA SBIR Phase I Report, Transgenic Citrate Synthase, Grant No. 68-D-02-018). A baseline comparison was conducted of the phytoremediation performance of non-transgenic tobacco strain vs. the E1 tobacco. Three performance indicators were assessed: (1) plant uptake of lead (Pb), a common soil contaminant; (2) extractability of Pb from the post-harvested biomass; and (3) effect of Pb in plant tissue on post-harvested cellulase activity.

Plant Uptake of Heavy Metals. Uptake of Pb and zinc (Zn) by the transformed tobacco was compared with wild-type and other tobacco varieties in Pb-contaminated soil E1-FLC transformed tobacco and Xanthi (non-transformed) tobacco were seeded in pots containing 300 g of soil with a Pb concentration of 800 mg/kg collected from a site in the Northeast U.S. The plants were grown for six weeks in Edenspace's growth chamber using a 16 hour day/8 hour night cycle. After six weeks, the plants received soil applications of a chemical induction agent to promote lead uptake before being harvested and analyzed to determine differences in uptake between the transgenic and control tobacco plants. All plants were harvested by cutting the stem of each plant approximately one-half inch above the soil surface. The plants were dried at 70° C., ground to pass a 20 mesh screen and digested following EPA Method 2050 (USEPA, 1986) followed by analysis using inductively coupled plasma (ICP) spectrometry (EPA Method 6010; USEPA, 1986).

Figure 5:
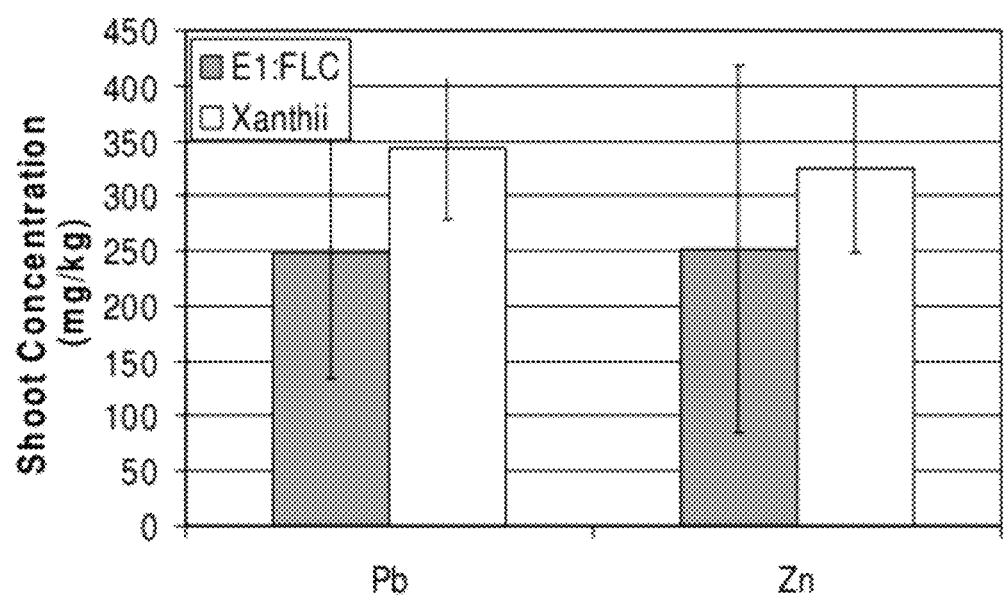
FIG. 5 is a graph showing shoot concentrations of Pb (lead) and Zn (zinc) in non-transformed and E1-FLC transformed tobacco grown in Pb contaminated soil. The results indicate comparable phytoremediation performance of the non-transformed and transformed tobacco.

As shown in FIG. 5, uptake of Pb and Zn were comparable in the transformed tobacco and non-transformed tobacco, indicating that the E1 plants could be used successfully for phytoremediation. This result is significant because it supports the possibility of growing transgenic plants for phytoremediation as well as for biofuel, creating opportunities for co-production cost savings.

Recovery of Plant-extracted Metals. Phytoextraction of metals removes metals from the soil (aluminosilicate matrix) and concentrates them in the plant tissue (lignocellulosic matrix). Recovery of metals from the biomass for recycling or efficient disposal should be improved if the cellulose can be effectively degraded to allow easy extraction and separation of the metals from the tissue.

This experiment demonstrates that application of exogenous cellulases to the dried biomass indeed resulted in improved extractability of metals from the plant tissue. Dried plant biomass from soils containing arsenic and lead was equilibrated in a citrate buffer (pH 4.5) with added cellulases, hemicellulases and glucoamylase. For lead and arsenic (As), greater than 95% of the elemental concentration was extractable from the dried biomass without the addition of cellulases, a result of great potential importance for biomass treatment and disposal in the phytoremediation industry. It is believed that the fine grinding (20 mesh) and heat are together responsible for this high extraction rate, which is superior to rates the Applicants have achieved using alternative extraction methods. Adding cellulases had no significant effect on this already high extraction rate.

Figure 6:
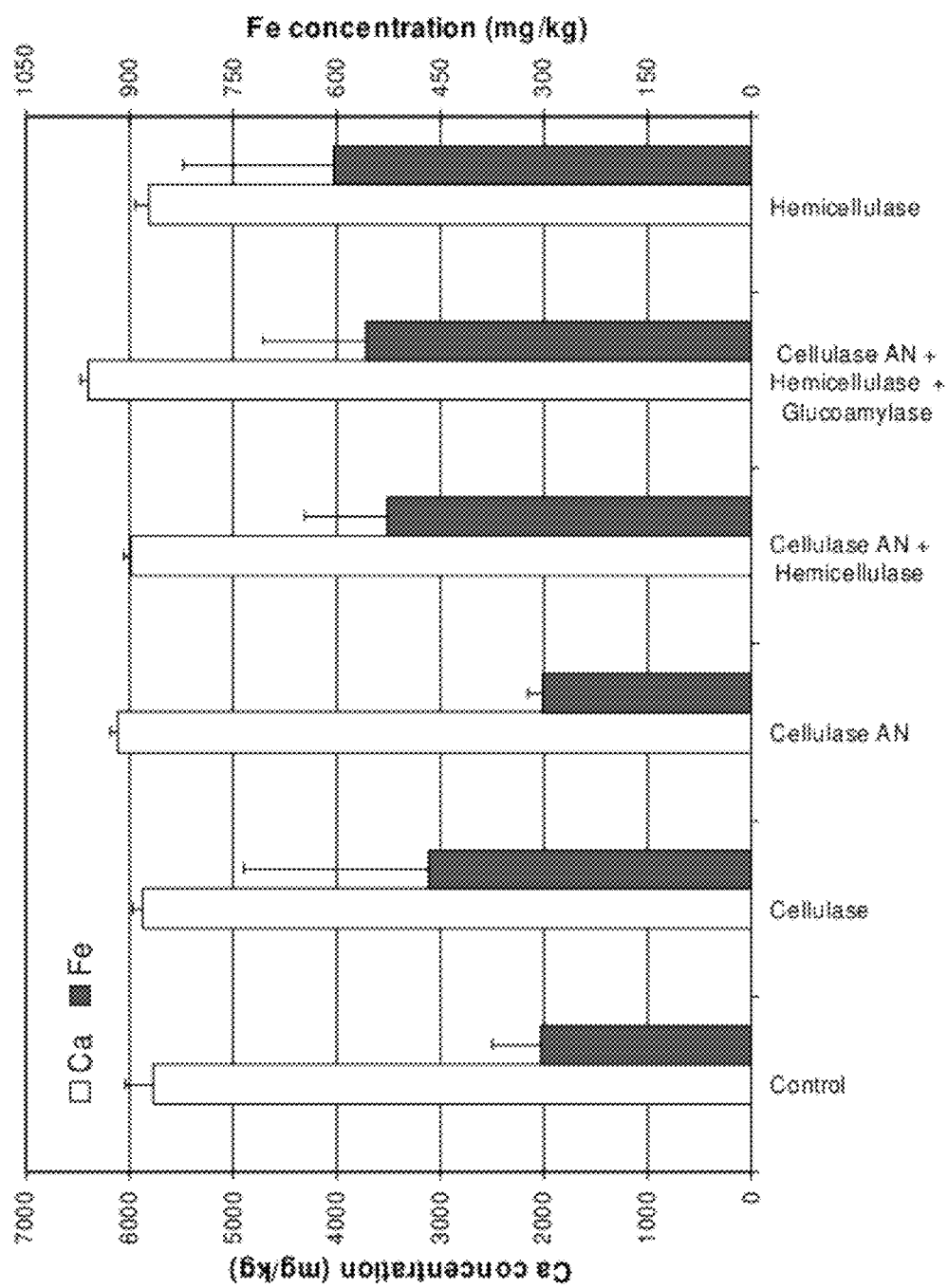
FIG. 6 is a graph showing the concentrations of extractable Ca (calcium) and Fe (iron) from dried and ground biomass incubated with pH 4.5 citrate buffer at 50° C. with various added cellulases.

Interestingly, as shown in FIG. 6, the application of cellulases did improve extractability of metals that are plant nutrients such as iron (Fe) and calcium (Ca), suggesting that these metals were more tightly bound in the lignocellulosic matrix than the contaminants, such as Pb and As. Variance in performance of the different members of the cellulase complex was observed; for example, hemicellulase, was more effective in releasing iron than calcium, suggesting that these metals are bound in different forms in the matrix.

Coarser grinding that is more indicative of likely production processes will be tested with the expectation that cellulase effects for metal extraction will become more pronounced as the plant particle size increases.

Effect of Extracted Metals on Cellulase Activity. To determine whether Pb concentrations in plant biomass would inhibit cellulase formation, E1 tobacco plants were grown in both uncontaminated and Pb-contaminated soils, then harvested and analyzed for Pb uptake as described above.

Figure 7:
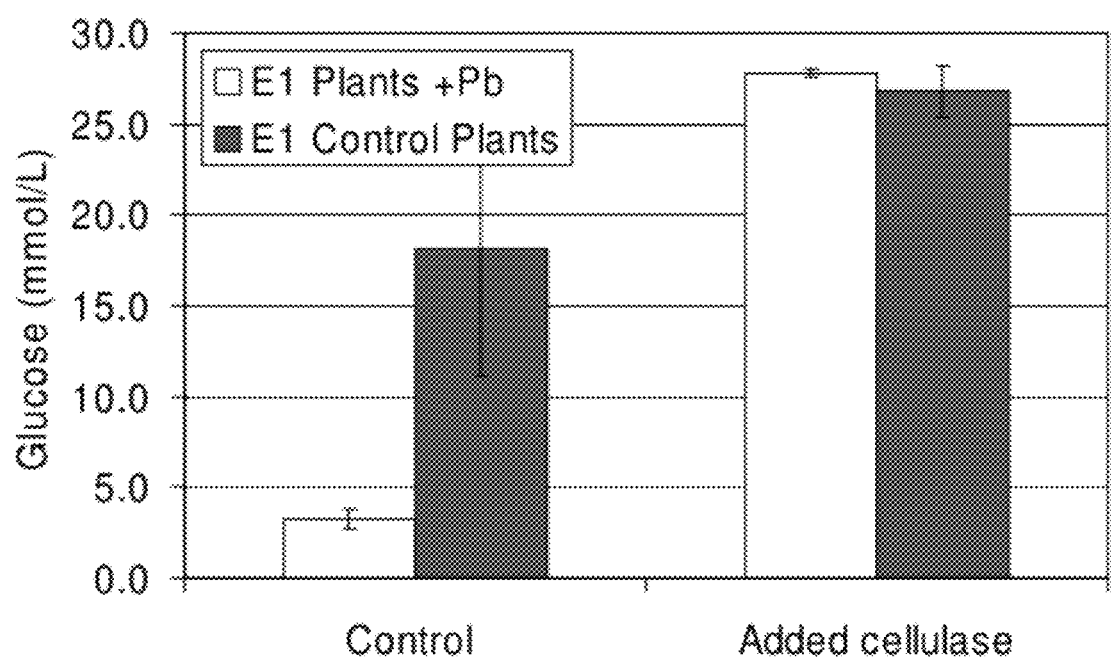
FIG. 7 is a graph showing results of glucose production from E1 tobacco grown in uncontaminated and Pb-contaminated soil in the presence or absence of exogenous cellulases. The results show that glucose production is lower in E1 tobacco containing approximately 300 mg/kg of Pb, but that this effect disappears when exogenous cellulases are added.

As shown in FIG. 7, glucose production was significantly lower in E1 plants grown in Pb contaminated soil. However, the application of exogenous cellulases resulted in similar glucose production from harvested dry biomass in both the presence and absence of Pb. There are several possible explanations for this result, including the possibility that Pb inhibits E1 activity but not the activity of other cellulases, and the possibility that the plant stress caused by chemically inducing metal uptake inhibits post-harvested glucose stability and/or E1 activity. Experiments will be performed to test these three possibilities.

Example 4

Transformation of Tobacco with FLC

The objectives in adding FLC to plants, as disclosed in the present invention, include increasing the biomass to improve bioenergy and phytoremediation performance, and delaying flowering time as a method of preventing transfer of transgenic pollens to other field crops. As AtFLC had not previously been expressed in tobacco, the first task was to perform the transformation in both wild-type control tobacco and E1 tobacco, and then test for successful integration and expression of AtFLC and continued expression of E1 in E1 tobacco.

The FLC construct (as described in Example 1) was transferred into an *Agrobacterium* vector for transformation of a non-transgenic tobacco and also to a T4 generation of an *Acidothermus cellulolyticus* E1 endo-1,4-β-glucanase-producing transgenic tobacco ($T_1$ seeds obtained from Dr. S. Austin-Phillips, University of Wisconsin).

Figure 8:
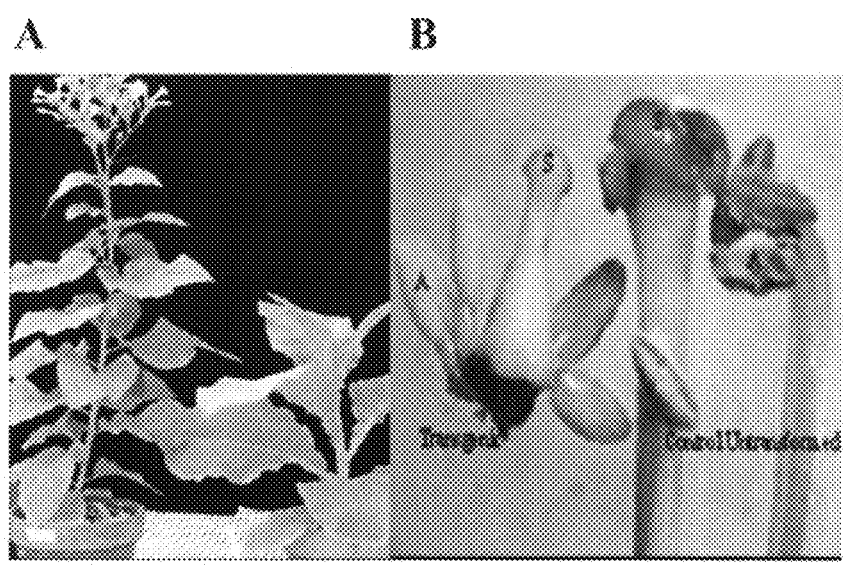
FIG. 8 presents two pictures illustrating delayed flowering and biomass increase in FLC-transformed tobacco.

Transformation of a non-E1 Tobacco with FLC. To observe the effects of FLC independent of E1, a non-E1 tobacco was first transformed with the FLC gene. The *Agrobacterium* strain GV 3101 containing the pGreen construct was used for transfer of the *Arabidopsis* FLC gene in tobacco (*Nicotiana tabacum* 'Samsun'). Five putative transgenic lines were selected and examined for the presence of FLC. Genomic DNA and the total RNA were isolated from the leaves and used for polymerase chain reaction (PCR) and RNA blot analysis, respectively. Both DNA and RNA tests confirmed the integration and transcription of FLC in all five lines and their $T_1$ progenies. Transgenic plants in one line showed an average of 36 days delay in flowering time compared to control plants (see FIG. 8) and the overall mean for all lines was 14 days delay. Transgenic plants also displayed increased leaf size and biomass yield and reduced height at flowering time. A manuscript presenting these results (H. Salehi et al., "Delay in flowering and increase in biomass of plants expressing the *Arabidopsis* floral repressor gene FLC (FLOWERING LOCUS C)", J. Plant Physiol., 2005).

Transformation of a Fourth-Generation E1 Tobacco with FLC. The $T_4$ generation of an *Acidothermus cellulolyticus* E1 endo-1,4-β-glucanase-producing transgenic tobacco was used for *Agrobacterium*-mediated transformation and expression of *Arabidopsis thaliana* FLC gene. Here too, the *Agrobacterium* strain GV 3101 containing the FLC and bar selectable marker cassettes (pGreen) was employed for transformation. Plants that showed the integration of both E1 and FLC were selected using bar selectable marker and PCR. Six E1 and FLC-positive putative transgenic lines, resistant to 5 mg/L glufosinate ammonium, were selected for further molecular analyses. Total RNA was isolated from leaves of 6-week old greenhouse plants, and used for the FLC RNA-blot analysis. The RNA test confirmed the transcription of FLC in all six E1cd-FLC lines.

Table 2a shows a comparison of control (non-transformed) and $T_o$ E1-FLC transgenic tobacco plants with regard to flowering delay and vegetative growth before flowering. Note that each line is a separate heterozygous genotype, with positional effects of the FLC gene in the tobacco genome creating variances in performance. Table 2b shows a comparison of control (non-transformed) and $T_o$ E1-FLC transgenic tobacco plants in fresh and dry weight biomass, thousand seed weight and seed yield per plant. As shown in Table 2a, transgenic E1cd-FLC plants showed an average of 9 to 21 days delay in flowering time compared to E1 cd-expressing control plants, and the overall mean for delay in flowering in all lines was 14 days. As did the FLC-only tobacco plants, E1cd-FLC plants also displayed statistically significant increases in leaf size and biomass yield (see Table 2b). All transgenic E1 cd-FLC plants were significantly shorter than control tobacco at flowering time. A manuscript presenting these results (H. Salehi et al., "Expression of flowering locus C in an Acidothermus cellulolyticus endo-1,4-β- D-glucanase (E1) transgenic tobacco (*Nicotiana tobacum* L.) and its effect on delay in flowering and increase in biomass", In Vitro Cellular and Developmental Biology - PLANT, 2005).

TABLE 2a

| Plants | Days to flowering after transfer to greenhouse | Flowering delay (d) | No. of leaves produced before flowering | Leaf area$^a$ ($cm^2$) | Plant height at flowering time (cm) |
|---|---|---|---|---|---|
| Control | 15 c$^b$ | 0 c | 19 ab | 187.5 d | 60 a |
| Transgenic: | | | | | |
| Line 1 | 22 b | 7 b | 18 ab | 213.8 c | 35 b |
| Line 2 | 23 b | 8 b | 20 a | 236.5 bc | 65 a |
| Line 3 | 24 b | 9 b | 21 a | 239.5 b | 35 b |
| Line 4 | 51 a | 36 a | 16 b | 369.7 a | 22 c |
| Line 5 | 23 b | 8 b | 20 a | 219.9 bc | 40 b |

$^a$Measured with second fully expanded leaf from the bottom.
$^b$in each column; means followed by the same letters are not significantly different using Tukey's test at 1% level.

TABLE 2b

| Plants | Biomass FW/plant | Biomass DW/plant | Thousand seed weight (mg) | Seed yield/plant |
|---|---|---|---|---|
| Control | 192.31 c | 35.22 bc | 66 c | 6.19 b |
| Transgenic: | | | | |
| Line 1 | 233.33 c | 33.47 c | 76 b | 3.18 d |
| Line 2 | 338.52 ab | 50.48 ab | 83 b | 7.12 a |
| Line 3 | 260.81 bc | 35.58 c | 81 b | 5.31 c |
| Line 4 | 335.03 ab | 51.65 a | 101 a | 0.17 e |
| Line 5 | 346.06 a | 45.79 abc | 81 b | 3.36 d |
| Average of 5 Lines | 377 | 43 | 84 | 4 |

In each column, means followed by the same letters are not significantly different using Tukey's test at P ≦ 0.01.

As shown in Table 2a, transgenic E1cd-FLC plants showed an average of 9 to 21 days delay in flowering time compared to E1cd-expressing control plants, and the overall mean for delay in flowering in all lines was 14 days. As did the FLC-only tobacco plants, E1cd-FLC plants also displayed statistically significant increases in leaf size and biomass yield (see Table 2b). All transgenic E1cd-FLC plants were significantly shorter than control tobacco at flowering time. A manuscript presenting these results (H. Salehi et al., "Expression of flowering locus C in an *Acidothermus cellulolyticus* endo-1,4-β-D-glucanase (E1) transgenic tobacco (Nicotiana tobacum L.) and its effect on delay in flowering and increase in biomass", In Vitro Cellular and Developmental Biology—PLANT, 2005).

The delay in flowering demonstrated in these experiments, particularly in open pollinated crops such as corn, could be a useful bioconfinement system to reduce the chance of cross-contamination of transgenic pollen with cross-breedable plants in the field. The substantial increase in biomass seen in three lines of the first-generation tobacco could be a useful trait to increase bioenergy content and phytoremediation performance.

Example 5

Transformation of Corn with E1-FLC

Figure 9:
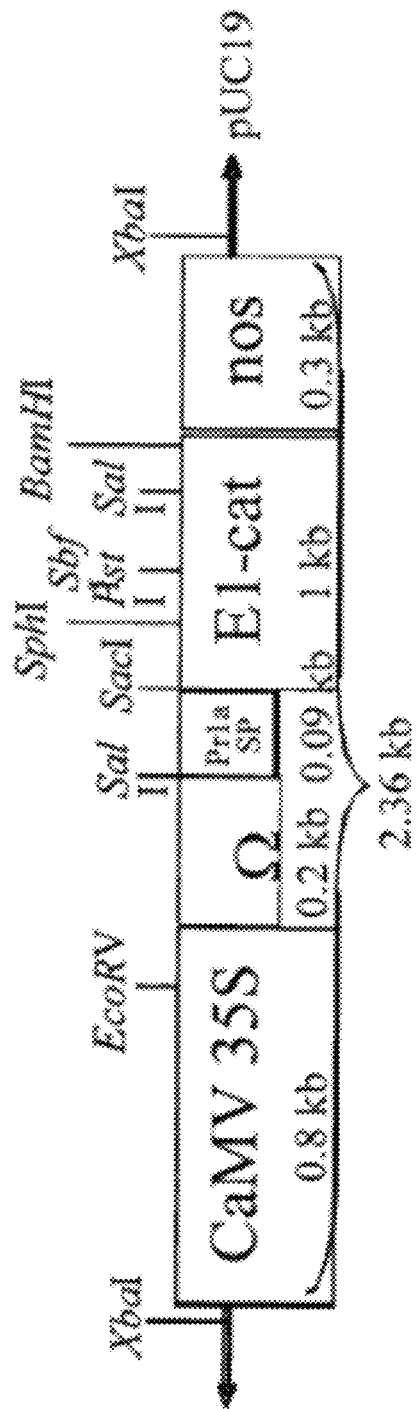
FIG. 9 shows the pMZ766E1-cat, a construct containing the *Acidothermus cellulolyticus* E1 catalytic domain driven by 35S promoter, and the sequence encoding the tobacco pathogenesis-related protein 1a (Pr1a) signal peptide for apoplast-targeting of the E1 enzyme. Abbreviations used in this scheme are as follows: CaMV 35S: Cauliflower Mosaic Virus 35S Promoter; Ω: Tobacco Mosaic Virus Ω translational enhancer; Pr1a SP: the sequence encoding the tobacco pathogenesis-related protein 1a (Pr1a) signal peptide; E1-cat: catalytic domain of the *A. cellulolyticus* E1; and nos: polyadenylation signal of nopaline synthase.

To develop a system for transforming corn, rice was used as cereal model plant system for transfer of the E1 and the bar genes. To do so, the pZM766E1-cat was inserted into pCAMBIA (purchased from pCAMBIA Co (Camberra, Australia) containing the bar selectable marker gene and the gus color indicator gene (see FIG. 9). The plasmid was obtained under a Material Transfer Agreement (MTA) from Dr. K. Danna of Colorado State University. The E1 transgenic rice plants showed the integration of all three transgenes (E1, bar and gus) by PCR. Furthermore, they showed E1 production as high as 24% total soluble proteins and enzymatic activity of the E1 transgene.

Several independent corn transgenic lines were then developed using biolistic bombardment. Lines showing confirmed integration, expression, enzymatic activity and accumulation of the transgene product inside of the apoplast were retained for further testing and development as described below.

Explant Preparation and Biolistic Bombardment of Corn. The Applicants produced multi-meristem apical shoot primordia for biolistic bombardment of a mixture of E1 and bar constructs. Corn was grown in greenhouses. Immature embryos were produced, cultured and callus lines were produced, and the immature embryo-derived callus lines were bombarded with a 1:1 ratio of a plasmid containing the E1 gene and one of the three plasmids, each containing the bar selectable marker gene.

Figure 10:
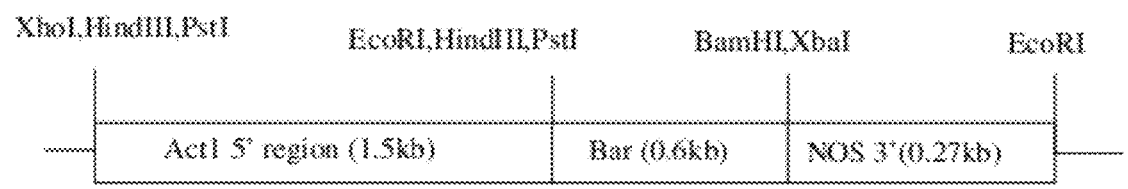
FIG. 10 shows the pDM302, a construct containing the bar-herbicide selectable marker gene controlled by rice actin 1 promoter and nos terminator. Abbreviations used in this scheme are as follows: bar: Phosphinothricin acetyl transferase (selectable marker/herbicide resistance) coding sequences; nos: Nopaline synthase terminator.
Figure 11:
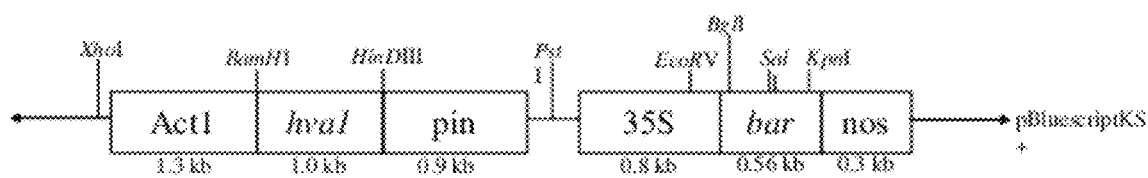
FIG. 11 shows the pBY520, a construct the barley Hva1 coding sequences regulated by rice actin 1 (Act1) promoter and potato proteinase inhibitor II terminator. It also contains the bar herbicide resistance selectable marker regulated by 35S promoter and Nos terminator. Abbreviations used in this scheme are as follows: Act1-5': Rice acting 1 promoter; Hva1: Barley Leah Protein coding sequences; PinII-3': Potato proteinase inhibitor terminator; 35S-5': Cauliflower mosaic virus 35S promoter; bar: Phosphinothricin acetyl transferase (selectable marker/herbicide resistance) coding sequences; and nos: Nopaline synthase terminator.

For the E1 plasmid, the pMZ766E1-cat (see FIG. 9) was selected because in *Arabidopsis* this construct produced the E1 enzyme up to 26% of the total soluble proteins (M. T. Ziegler et al., Mol. Breeding, 2000, 6: 37-46). This construct contains the strong promoter and enhancer and an apoplast targeting element. Corn multi-meristems and the immature embryo-derived callus lines were co-transformed with the pZM766E1-cat and either the pGreen (Fig. XX0, pDM 302 (FIG. 10), or the pBY520 (FIG. 11), as each has its own potential advantages.

Figure 12:
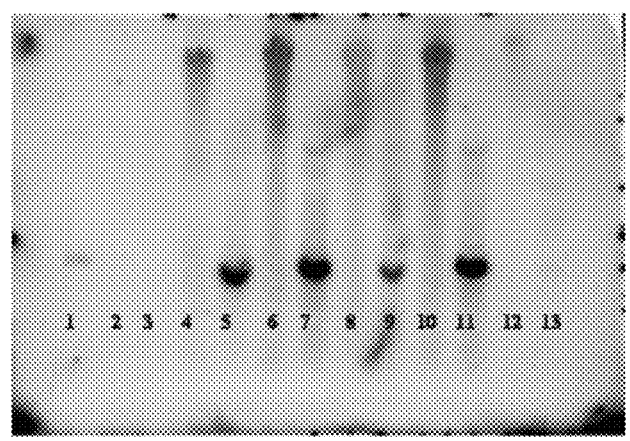
FIG. 12 shows the results of Southern blot analysis of genomic DNA from corn plants, probed with the E1-cat. Lane 1: 10 pg of Sac 1 E1 fragment from pMZ766; Lanes 2-3: untransformed corn control (lane 2: DNA undigested and lane 3: DNA digested); Lanes 4-13: five independent pMZ766 transformants; (lanes 4, 6, 8, 10, and 12: DNA not digested; lanes 5, 7, 9, 11, and 13: DNA digested with Sac I). Size of bands is 1 kb.
Figure 13:
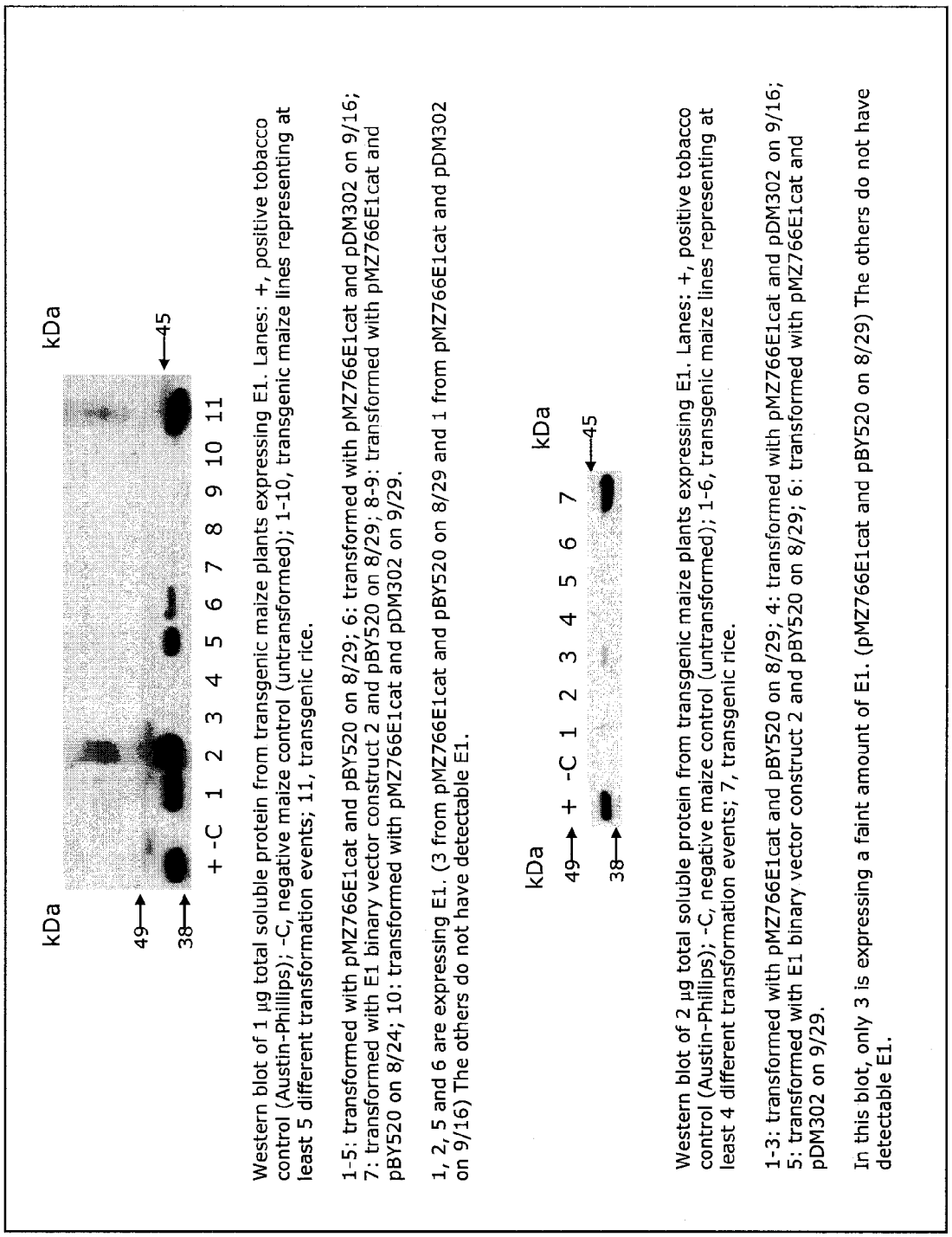
FIG. 13 shows Western blots of transgenic corn as compared to transgenic rice and transgenic tobacco.

Confirmation Analysis of E1 Transgenic Corn. PCR was used on a few PPT-selected plantlets and confirmed the presence of the E1 and bar genes. Those plantlets which showed positive signals were selected for further studies. Although the copy numbers of E1 in corn plants using the gene unique site has not yet been determined, Southern blot analysis confirmed the stable integration of E1 transgene in several PCR positive corn lines (see FIG. 12). The translation of E1 transgene in corn was confirmed using Western blots and compared to E1 translation in tobacco and rice (see FIG. 13).

Figure 14:
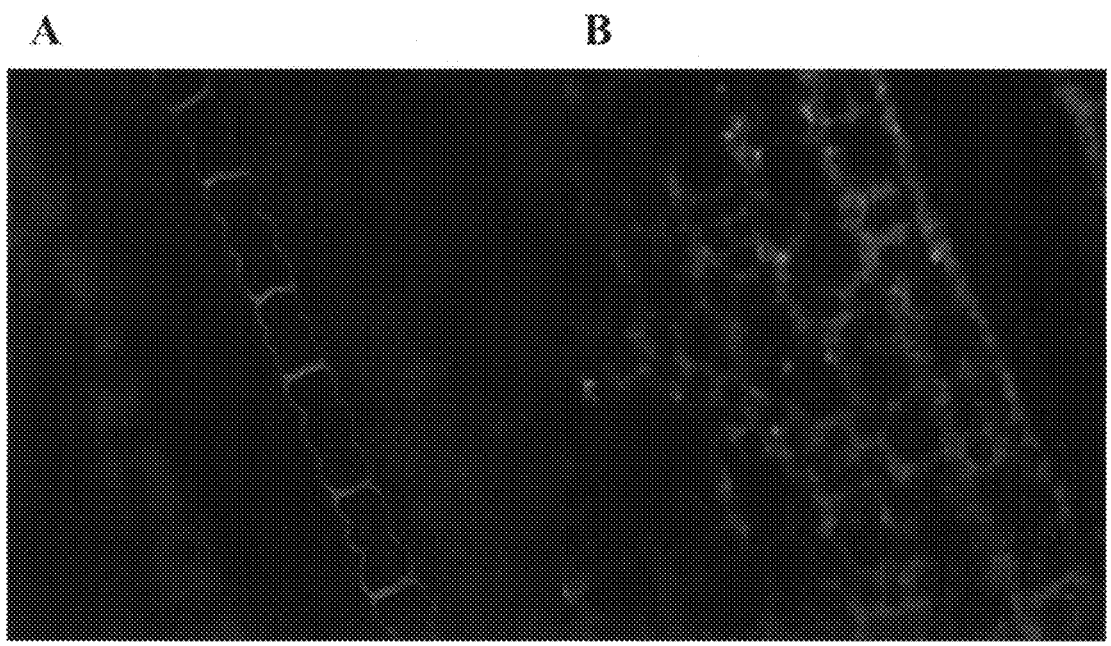
FIG. 14(A) is a picture of E1 transgenic maize leaf tissue obtained by immunofluorescent confocal laser microscopy image microscopy using the E1 primary antibody and the FITC anti-mouse secondary antibody. This picture shows that E1 transgenic leaf tissue exhibits apparent storage of E1 in the plant apoplast.
FIG. 14(B) is a confocal microscopy image of leaf tissue from an untransformed control maize leaf showing no expression of E1 enzyme.

Preliminary Work on Apoplast Localization of E1 in Transgenic Corn. Based on previous experience with localization studies of other gene products (polyhydroxybutyrate) in corn via confocal microscopy, an E1 primary antibody and an appropriate secondary antibody were used to perform localization of E1 in transgenic corn tissue. Although most samples showed strong non-specific binding of the fluorescence conjugate to plant tissues, some samples showed possible localization of E1 in apoplast (FIG. 14). None of the plant lines generated as described herein appeared to show adverse growth effects from the non-specific binding of E1 in their tissues. Increased localization of E1 in apoplast will be pursued using several different blocking agents to reduce any potential non-specific binding.

Level of E1 Production and E1 Biological Activity in Transgenic Plants. Table 3 shows E1 enzymatic activity and percentage E1 in total soluble proteins in $T_O$ corn $T_4$ tobacco and $T_O$ rice. Corn lines for which results are reported in this table are the same as studied by Western blot in FIG. 13. Several strains of $T_0$ corn were grown, the amount of E1 enzyme produced and its biological activity were measured and compared with its performance in a $T_4$ E1 tobacco and $T_0$ E1 rice. Performance between the $T_0$ strains varies because of positional differences in the insertion point of E1 in the corn genome. On strain, Corn 1-2, showed excellent E1 production and activity, with E1 accounting for 9.07% of total soluble proteins (TSP), or approximately 1% of the corn total dry weight. In comparison, one line of rice produced E1 at 24.13% of TSP, and a line of tobacco 3.8% of TSP (see Table 3). The high productivity of the rice line observed in the present study is comparable to the result achieved earlier in *Arabidopsis*, and suggests that higher yields can be achieved in corn than obtained here. Accordingly, new E1 corn lines will be created to seek enzyme yields of more than 20% of TSP.

TABLE 3

| Plant lines | Activity (nmol/ug/min) | % E1 in total soluble proteins |
|---|---|---|
| Control corn | 0.00 | 0.00 |
| Corn 1-1 | 0.1044 | 0.261% |
| Corn 1-2 | 3.629 | 9.07% |
| Corn 1-4 | 0.0798 | 0.199% |
| Corn 1-6 | 0.0735 | 0.184% |
| Corn 1-10 | 0.0124 | 0.031% |
| Corn 1-11 | 0.186 | 0.465% |
| Corn 1-13 | 0.0331 | 0.083% |
| Corn 2-3 | 0.0727 | 0.182% |
| +transgenic tobacco | 1.521 | 3.8% |
| Rice 8 | 9.654 | 24.134% |

Summary of Results Obtained

The results obtained in the Examples reported herein provide strong support for the contention that tailoring crop plant traits can significantly improve biofuel yields and reduce biofuel production costs. Robust activity by a key cellulase enzyme, E1 endoglucanase, was demonstrated in transformed tobacco and corn. One E1 corn line has shown E1 production at more than 9% of total soluble proteins, a level approximately equal to the level of exogenous enzyme today added to cellulosic biomass for hydrolysis. Significantly, addition of exogenous enzymes led to higher glucose yields from E1 tobacco than non-transformed tobacco, suggesting that higher ethanol yields can be achieved simply by using today's hydrolysis techniques on E1 crop plants. The results obtained also showed that the FLC gene delays flowering in tobacco, as it had earlier been shown to do in *Arabidopsis*, a trait that is likely to be useful in bioconfinement of transgenes in bioenergy crops. FLC may also confer greater biomass. From the standpoint of co-production of crops for bioenergy and phytoremediation, the present results showed that E1-FLC plants can extract as much contaminant as the plants normally used in phytoremediation, and that two of the most contaminants, arsenic and lead, can be extracted from the harvested biomass at levels exceeding 95%, facilitating metals recycling as well as downstream bioenergy use of the hydrolyzed sugars.

Future Work

Future work will build on these results. The existing E1 lines of corn will be grown and bred to produce reliable, high-yield lines for field testing and pilot ethanol production in cooperation with the National Renewable Energy Laboratory. New E1 lines will be created with the goal of further boosting E1 yields. In addition, two new corn genotypes will be created, both having the FLC gene, one further containing a ligninase directed at lignin and the other containing a hemicellulase directed at xylan to follow up the demonstration that combinations of different types of cellulase enzymes achieve greater total hydrolysis than single enzymes. Additional research will also be conducted on how the transformed corn can simplify current process technologies, for example by reducing pre-treatment requirements. Continuation of phytoremediation experiments will provide additional information on the constraints and opportunities of co-production. As planned, future work should provide the basis for introducing a multi-trait crop plant with substantial near-term fuel ethanol and phytoremediation market potential, and create a biomass production, transportation and processing infrastructure that is vital to creation of renewable feedstocks for the hydrogen economy. More specifically, future work will include the studies described below.

Development of Three Separate Corn Lines Producing E1 Endoglucanase, a Hemicellulase and Ligninase at Levels Greater than 15% Total Soluble Protein (TSP)

Targeting cellulase, hemicellulose and lignin, which together comprise approximately 75% of corn stover biomass, is expected to hydrolyze more than double the lignocellulosic biomass compared to a cellulase-only approach. While a TSP of greater than 4% E1 is sufficient to hydrolyze cellulose in corn biomass, and a level of 10% is approximately equal to current loading rates of exogenous cellulases, levels of approximately 25% have been demonstrated in rice and *Arabidopsis*, making a 10% to 20% goal in corn a realistic target. Higher levels of enzyme production will lead to more complete hydrolysis, particularly when used in a "blend" of the corn varieties where each variety must hydrolyze the target lignocellulose from the other varieties as well as in its own biomass. The three separate corn genotypes, each producing a different enzyme, will provide flexibility in growing any desired proportion of enzymes simply by adjusting the seed mix at planting.

Transformation of Corn with Xylanase and Ligninase Genes. To maximize sugar production from the biomass, a high biomass corn will be transformed to produce xylanase (using a gene provided by Dr. Jonathan Walton, Michigan State University) or to produce a ligninase (using a gene provided by Dr. C. A. Reddy, Michigan State University). Transgenic plants will be tested for integration, copy number, and transcription of the transgenes, translation levels, enzymatic activity and apoplast localization of enzymes, overall plant health, and biomass production.

Figure 15:
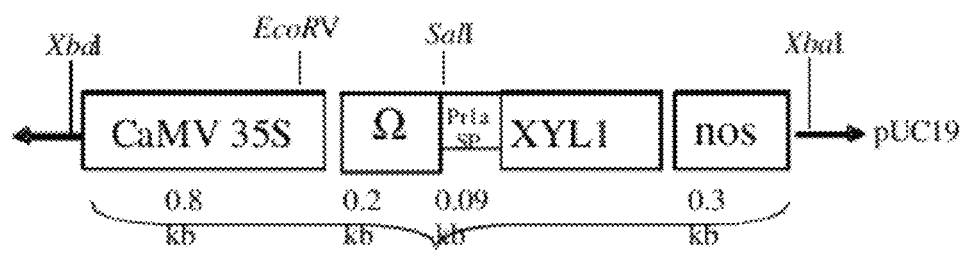
FIG. 15 shows a construct containing the *Cochliobolus carbonum* endoxylanase/hemicellulase cDNA regulated by the 35S promoter and enhancer. This construct contains the sequences encoding the tobacco pathogenesis-related protein 1a (Pr1a) signal peptide for targeting of XYL1 into plant apoplast. Abbreviations used in this scheme are as follows: CaMV 35S: Cauliflower Mosaic Virus 35S Promoter; Ω: Tobacco Mosaic Virus translational enhancer; and Pr1a SP: the sequence encoding the tobacco.

Creation of Xylanase and Ligninase Gene Constructs. Two new gene constructs will be developed, one containing the *Cochlibolus carbonum* endoxylanase (XYL1) (P. C. Apel et al., Mol. Plant Microbe Interact., 1993, 6: 467-473), and the other containing the white rot filamentous *Phanerochaete chrysosporium* ligninase (CGL5) (H. A. de Boer et al., Gene, 1988, 69(2): 369). Each will contain cDNA sequences regulated by the tobacco mosaic virus 35S promoter and enhancer, and the tobacco pathogenesis-related protein 1a (Pr1a) signal peptide to target the enzyme inside the corn apoplast where pH of about 5.5 is ideal for stability of these three enzymes (need pH of 4.8 to 5.5). These constructs (see FIG. 15) will be similar to the construct containing the NREL's *Acidothermus cellulolyticus* endo-1,4-β-D-glucanase (E1) gene (see FIG. 9) that was used in the experiments presented in the Examples reported above. Using this E1-containing plasmid, production of E1 enzyme in transgenic plants ranged from 0.1% to 25% of TSP (a variation that is due to a position effect) (M. T. Ziegler et al., Mol. Breeding, 2000, 6: 37-46). As reported above, transgenic corn and transgenic rice were created that produced up to 3.8% and 24% of TSP, respectively.

Transformation of Corn with the Gene Constructs. HI II corn lines will be grown to maturity in greenhouses. Immature embryos will be collected to produce immature embryo-derived cell lines in vitro as described in the corn transformation reported above. The HI II corn immature embryo-derived cell lines will then be co-transformed with each of the above three constructs and another construct (pGreen) containing the bar herbicide resistance selectable marker and the *Arabidposis* Flowering Locus C (FLC) genes as performed for producing E1 transgenic corn (see above). Plants will be separately transformed with a 1:1 ratio of XYL1 and FLC, or the CGL5 and FLC so that each transgenic plant will express with the endoxylanase and FLC or the ligninase and FLC.

Embryonic cell lines will be bombarded with tungsten particles coated with 1:1 ratio of each of the cell wall degrading plasmids and the plasmid containing bar-FLC genes, as described above. The bombarded explants will be transferred onto selection medium containing 6-10 mg/L glufosinate ammonium (PPT) for another 6-8 weeks. Chemically selected cells will be regenerated into somatic embryos, germinated into plantlets in appropriate media containing the same concentration of PPT. Ten (10) centimeter plantlets will be transferred to pots, acclimated, and transferred to Edenspace corn greenhouses where they will be grown to maturity.

Test Cellulase Production in the Transformed Corn

The transformed corn will be tested for cellulase production and stability under different operating conditions and pre-treatments.

Confirmation of Corn Transgenesis. Corn plants produced in the greenhouse will be evaluated to confirm the integration, copy number and transcription of the above transgenes as performed for E1 transgenic corn gene integration (FIG. 12) and expression (FIG. 13) and FLC transgenic tobacco (H. Salehi et al., "Delay in flowering and increase in biomass of plants expressing the *Arabidopsis* floral repressor gene FLC (FLOWERING LOCUS C)", accepted for publication in J. Plant Physiol., 2005 and H. Salehi et al., "Expression of flowering locus C in an *Acidothermus cellulolyticus* endo-1, 4-β-D-glucanase (E1) transgenic tobacco (*Nicotiana tobacum* L.) and its effect on delay in flowering and increase in biomass", accepted for publication in In Vitro Cellular and Developmental Biology—PLANT, 2005). Herbicide resistance will be used as the initial selection criteria for successful transformation. Plantlets exhibiting herbicide resistance will be subjected to further characterization using PCR, Southern blot, Western blot, and Northern blot analyses.

PCR will be used to confirm the presence of foreign genes in plants. Those shoots/plantlets which show positive signals will be considered putatively transformed. To determine the copy numbers of transgenes in plants, genomic DNA will be isolated from greenhouse-grown putatively transgenic and control (untransformed) plants, then Southern blot analysis will be performed. A Southern blot analysis using the unique site of the plasmid will determine the copy number of each transgene in transgenic plants. Western blots will be performed to find the translation of transgenes in transgenic plants. The translation of E1 transgene in corn was already confirmed (see FIG. 13) and compared to the translation of the same E1 transgene in transgenic tobacco and transgenic rice. To confirm the expression of genes at the transcription level total cellular RNA will be isolated from plant tissues. The mRNA coding the foreign genes will be detected by RNA blot analysis using the same probes used Southern blot hybridization, labeled as above. The mRNA will be electrophoresed on a denaturing formaldehyde agarose gel, transferred to nitrocellulose or nylon filters, hybridized with the appropriate probe, and then exposed to X-ray film. After exposure of the probed RNA-containing filter to X-ray film, the hybridization bands will be scanned using a densitometer to determine the levels of specific mRNA present.

Characterization of Enzymatic Expression and Identification of High-expression Lines. The production level of each of the E1, XYL1, and CGL5 heterologous proteins as a fraction of plant total soluble proteins, along with the enzymatic activity of each of the above three enzymes in each transgenic line, will be determined in a manner similar to that performed for E1 transgenic corn plants described above. High production lines will be preserved for future bulking up of seed and testing. The production and biological activity of E1 enzyme in transgenic corn, rice and tobacco plants was determined in the Examples reported above. Further evaluation of enzyme production activity for the XYL1 and CGL5 transformed corn will performed using procedures provided by Drs. Walton and Reddy (Michigan State University).

Confirmation of Enzyme Storage in Plant Apoplast. The localization of each of the above three heterologous enzymes in plant apoplast, the area between the cell wall and cell membrane (vs. the chloroplast or vacuole, as achieved in other transgenic cellulase plants) will be confirmed via the use of each of their primary antibodies and secondary antibodies followed by confocal microscopy as described above (see FIG. 14). While no adverse effects to plant growth from E1 expression were observed in E1 transformed plants generated so far, apoplast expression is desirable to segregate stored E1 from plant metabolism.

Antibodies to XYL1 and to CGL5 will be prepared to perform immunofluorescent antibody staining to determine the localization of the XYL1 and CGL5 in transgenic corn apoplast. The transgenic leaf section samples will be incubated in a solution containing the primary antibody of each of the above two enzymes. After washing to remove unbound antibodies, the tissues will be incubated in the secondary antibody-fluorophore conjugate (goat anti rabbit IgG-Alexa conjugate). After washing to remove unbound antibody-conjugate, the tissues will be mounted on microscope slides and viewed with a laser scanning confocal fluorescence microscope to determine the localization of these heterologous enzymes in transgenic plants.

Determination of Biomass Production and Time of Flowering. The results obtained showed a significant delay in flowering and an improvement in plant biomass production in tobacco transformed with FLC. The level of FLC heterologous protein production and its effects on delay in flowering and increased biomass production will be determined in transformed corn. A high performance E1 corn line will be used to validate the project goals in a small field trial.

Production of a $T_1$ (R2) E1 Corn Seed for Field and Production Testing. Seed for small scale field studies using E1 transformed corn (and other promising transgenic lines will be obtained using T1 plants that will be grown to maturity and crossed and/or selfed to bulk seed. Transgenic plants will be confirmed by scoring for herbicide resistance and the intactness and number of transgene insertion events will be determined using DNA blots.

Evaluation of the Use of Biomass from Transformed Plants for Feedstocks Production and Multi-Use Applications Transgenic corn and transgenic tobacco will be assessed for bioenergy use as well as for potential uses such as phytoremediation applications (e.g., barrier strips, controlling runoff, remediation of contaminated soils). One of the primary goals is to develop a crop that has the necessary characteristics of a high yielding biofuel feedstock; however, in some cases, the crop production costs may be leveraged with applications, such as phytoremediation, that provide additional benefits. As shown in the Examples above, an E1-FLC tobacco was developed that has the capability to function as a phytoremediation crop for lead as well as to express significant levels of E1 activity. In addition, the accumulation of lead in the biomass was observed to result in moderate suppression of glucose production in E1 transformed plants in the absence of applied external cellulases. However, when external cellulases were added, glucose production was observed to be similar to that of non-transformed plants. The potential of using the transformed tobacco and transformed corn will be further evaluated.

Seed of transformed tobacco and transformed corn (obtained as described herein) and a variety of conventional corn will be seeded in lead contaminated soil from a site in Baltimore, Md. and in potting mix and grown in the growth chamber and greenhouse at Edenspace. The plants will be grown for ten (10 weeks before harvesting. One week prior to harvest, half of the plants growing in each soil will receive a soil application of citric acid to enhance uptake of Pb and other metals in the soil. The biomass will then be harvested and split into two subsamples for each treatment combination. One biomass subsample from each treatment will be dried at 70° C. and ground to pass a 20 mesh screen using a Wiley mill. The remaining biomass subsamples will be homogenized individually in a blender with water at a 1:2 plant (fresh wt.):water ratio. The suspension will then be filtered to remove coarse solids and the resulting extract used for analysis of E1 activity (glucose production).

Feedstock Production Assessment. The quantity and quality (fermentation suitability) of sugars produced by the enhanced plants will be compared to sugars produced by conventional plants using commercially available cellulase and hemicellulase mixtures. Extracts and dried plant biomass will be incubated with a citric acid buffer (pH 4.5) at 50° C. for 24 and 48 hours in the presence and absence of added cellulase and hemicellulase mixtures. Sugar content of the resulting extracts will then be determined using HPLC to assess cellulase activity.

Determination of the effect of metal uptake on cellulase activity. The plant extracts and dried plant biomass will be analyzed for Pb and other metals prior to incubation with the added cellulases. After incubation the extracts will be filtered to 0.45 µm and analyzed for total metals to determine the effect of cellulase activity on the release of metals from the plant biomass as well as quantify any reduction in cellulase activity as a result of metal uptake by the plant.

Field Scale Production of a Biofuel Crops

A site has been selected to host the demonstration conducted by Edenspace. The field demonstration will be performed under a USDA APHIS permit. Edenspace has obtained such permits for other fieldwork with transgenic plants. The site will be selected in a manner to isolate experimental corn spatially from any wild relatives or other corn crops, a 3 m wide non-transgenic pollen trap crop will be planted around the experimental plants, and the sites will be visited periodically for one year after harvest to ensure that no plants have survived the demonstration.

Based on the provisions of the APHIS permit, a 10,000 square foot demonstration site will be prepared (with an appropriate buffer area), fertilized and seeded with a E1-FLC (or other promising lines) transformed corn, control (wild type), and an existing variety of high starch corn. The plot area will be seeded with the selected genotypes and grown for a full season to maturity. Growth parameters such as germination rate, plant population, days to flowering, grain yield and total biomass yield will be monitored for each of the genotypes.

At maturity, but before senescence, the grain and remaining biomass (stover) will be harvested and segregated for each of the genotypes. Representative samples of the biomass and grain will be analyzed for total starch, sugars and cellulose content.

Testing of Ethanol Yield of the Transformed Corn in the NREL Pilot Production Facility The National Bioenergy Center at the National Renewable Energy Laboratory, (NREL) has agreed to assist this part of the project with evaluation of ethanol production using enhanced corn in its Bioethanol Pilot Plant facility in Golden, Colo. Three lines of corn (transformed corn (e.g., E1-FLC corn); wild-type control corn, and non-transformed control corn) will be each grown in test plots, producing three biomass sample types. Each of these corn samples will be used as described below.

Comparison of Ethanol Yields from Transgenic Biomass to those Obtained from Exogenous Cellulase Applied to Control Biomass. Approximately 2.5 kg fresh weight biomass, excluding grain, of transformed corn (e.g., E1-FLC corn) grown on uncontaminated soil (Sample Type 1) will be ground to 10 mesh. Water will be added to bring the total volume of the slurry to 5 L. The slurry will be heated in the pilot production vessel at a temperature of 50° C. for 48 hours. Fermentation microorganisms will then be added, with the heat reduced to 40° C. for a period of 48 hours. During the entire period of 96 hours, 10 mL samples will be taken at 6 hour intervals for hexose and pentose sugar composition analysis and ethanol analysis.

This procedure will be repeated for Samples 2 and 3 but with wild-type control corn, and non-transformed control corn, an external cellulase (Celluclast™) will be added at t=0.

The slurry residue will be dried and weighed to determine what proportion of the biomass remains after processing. The results will be analyzed to compare performance of transgenic and non-transgenic corn with respect to ethanol production.

Evaluation of Ethanol Yield from Transgenic Biomass to Which Exogenous Cellulase has been Added. Following the above procedure, transgenic corn (e.g., E1-FLC corn) from the test site (Sample 1) will be processed together with Celluclast. Ethanol yield will be compared to yields from the transgenic corn only and Celluclast-only processes.

Evaluation of Ethanol Yield from Transgenic Biomass Combined with Control Biomass. Following the above procedure, 1.25 kg fresh weight transgenic corn (e.g., E1-FLC corn) from the site (Sample 1) will be combined with 1.25 kg fresh weight of control corn (Sample 2) and processed with the addition of exogenous cellulase. The results obtained will allow to determine the extent to which target production levels of enzyme (e.g., E1) (20% of TSP) in the transgenic (e.g., E1-FLC) biomass are sufficient to hydrolyze cellulose in added biomass not containing the enzyme (e.g., E1).

Evaluation of Ethanol Yield of Simultaneous Hydrolysis and Fermentation. Following the above procedure, transgenic corn (e.g., E1-FLC corn) from the site (Sample 1), including dry milled corn seed, will be processed together with two amylase enzymes (α-amylase and glucoamylase). This will be repeated for control corn from the uncontaminated site (Sample 2). The results will be compared to demonstrate the ability to co-process lignocellulosic biomass and starch.

Evaluation of the Effects of Pre-processing on Cellulase Performance. NREL will perform an initial screening study of Edenspace-supplied cellulosic biomass feedstock. This work will investigate a variety of pre-processing conditions with the intent of identifying conditions that maximize conversion yields (i.e., conversion of polymeric material into monomeric sugars). NREL will process samples at ambient and higher temperature and pressure conditions and assess conversion yields in shake flask experiments, and assess enzymatic activity before and after preprocessing.

Evaluation of the Ability of Ligninase and Hemicellulase Application to Substitute for Chemical/Heat Pre-treatment. Based on results of the evaluations described above, NREL will conduct performance testing in 5 L bench scale fermentors to generate performance results backed up by rigorous material balance data. Sufficient material for this work will be produced at those conditions that maximized conversion yields in the earlier shake flask experiments. Conversion results with the pretreatment will then be compared to results using corn containing ligninase and hemicellulase as a substitute for pretreatment.

Evaluation of Economic Performance

A preliminary estimate of the cost of producing ethanol from the enhanced corn will be prepared. Factors to be assessed include cost differentials in exogenous cellulases, pretreatment methods, fermentation and other production methods and plant cultivation, together with ethanol yield differentials. Recommendations for integration of transgenic plants in existing ethanol production facilities will be provided, together with recommendations for future use of the techniques in production of hydrogen fuel.

Example 6

Co-Processing of Cellulosic Material and Starch for Enhanced Ethanol Production

Background. In the U.S., fuel ethanol is produced through the fermentation of glucose from the starch in corn grain, but limited grain supply and competing uses for food and animal feed will constrain future growth in ethanol production from this source. The present invention provides a method to increase ethanol yields from corn grain by engineering corn to express cellulase enzymes, facilitating hydrolysis of cellulosic material in the grain into fermentable sugars. Production of enzymes in the grain offers significant potential advantages over current manufacturing technology, including low variable cost for the enzymes and excellent mixing of the enzymes and cellulosic substrates. Successful completion of this project could produce an additional 1.1. billion gallons of ethanol from corn grain annually by 2012. This project will also lay the foundation for broader application of this "endoplant enzyme" approach to much larger sources of cellulosic biomass that include corn stover, switchgrass and other renewable energy crops.

In the U.S., ethanol is produced from corn grain, which is primarily made up of starch, a glucose polymer that is easily hydrolyzed to individual glucose molecules for fermentation (yeasts can then be used to convert the glucose to ethanol through alcohol fermentation). There are two large scale methods for converting corn kernels to ethanol, the wet mill and dry mill processes. Wet mills process the kernels by wet-grinding and fractionating them into starch, oil, fiber, and protein components (M. R. Ladisch and J. A. Swarczkopf, Biores. Technol., 1991, 36: 83-95; and M. Gulati et al., Biores. Technol., 1996, 58: 253-264). While only the starch fraction is used for ethanol, the other components are used to produce such valuable products as animal feed and corn oil. In dry milling, the entire kernel is ground to flour and processed together to produce ethanol through a series of steps. The corn kernel is ground up and liquefied, releasing the starch in the grain, which is then hydrolyzed and fermented to produce ethanol and dried distillers grain used as animal feed (M. R. Ladisch and J. A. Swarczkopf, Biores. Technol., 1991, 36: 83-95; and M. Gulati et al., Biores. Technol., 1996, 58: 253-264). In 2000, approximately 54% of the ethanol production in the U.S. came from wet mills (M. Graboski, "Fossil Energy Use in the Manufacture of Corn Ethanol", Prepared for the National Corn Growers' Association, 2002), but the dry milling process is a technically simpler process for producing ethanol, and a dry milling plant is less expensive to build (V. Singh and S. Eckhoff, Cereal Chem., 1996, 73: 716-720). Consequently, the majority of ethanol plants currently under construction are dry milling plants and by the year 2012 80% of the ethanol produced in the U.S. will be from dry milling plants (M. Graboski, "Fossil Energy Use in the Manufacture of Corn Ethanol", Prepared for the National Corn Growers' Association, 2002).

As reported herein, the present Applicants have demonstrated that tobacco plants expressing E1 produce higher levels of glucose when incubated at temperatures that activate E1. While the goal of engineering cellulase enzymes into plants is to directly convert the transgenic biomass into glucose, the transgenic plants can also be used as a source of cellulase that can be added to other plant biomass for cellulose hydrolysis. While the majority of the corn kernel is made of starch, the hull of kernel is primarily cellulose. Overall, approximately 9% of the biomass in corn kernels is cellulosic material (4% cellulose, 5% hemicellulose) (M. Gulati et al., Biores. Technol., 1996, 58: 253-264) and can be efficiently hydrolyzed by dilute acid treatment (B. Dien et al., J. Industrial Microbio. Biotech., 1999, 22: 575-581) or cellulase enzymes to provide additional glucose and pentose sugars for fermentation (D. Irwin et al., Appl. Microbio. Biotech., 2003, 61: 352-358) and increase ethanol yields (V. Singh et al., ASAE/CSAE Meeting Paper No. 046056, 2004, St. Joseph, Mich.). In addition, the cellulose in corn kernels is an attractive cellulose feedstock because there is almost no lignin present to shield the cellulose from enzymatic hydrolysis.

Figure 17:
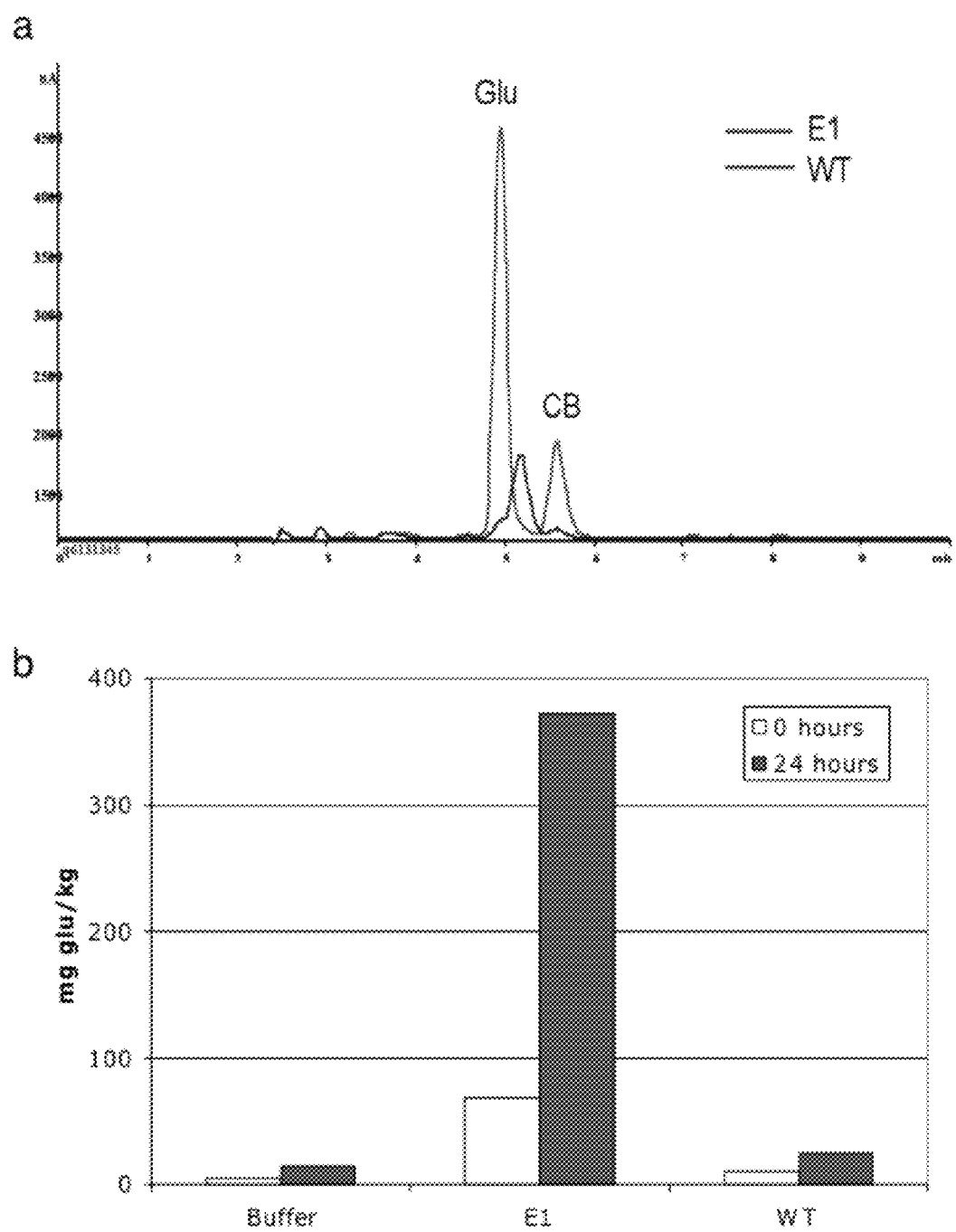
FIG. 17(*a*) shows IC chromatograms from corn kernels incubated with E1 or WT tobacco extract indicating various sugar molecules present in the solution (see Example 6). Peaks are labeled as follows: Glu: glucose; CB: cellobiose. There is a small cellobiose peak observed in the WT extract incubation, but no glucose. Instead, incubation with the WT extract produced an unknown carbohydrate peak FIG. 17(*b*) is a graph showing concentrations of glucose from corn grain samples incubated in either a citrate buffer control, E1 tobacco extract, or wild type tobacco extract. Glucose readings were taken at 0 and 24 hours after the addition of the extracts.

Preliminary Results and Technical Objectives. In preliminary experiments, the present Applicants have investigated whether the plant produced E1 enzyme will be useful in converting the cellulose in corn kernels into glucose using extracts from E1 tobacco. Wild type corn kernels dried and ground to 20 mesh were incubated with E1 tobacco extract at 65° C. to activate the E1 enzyme. Analysis by ion chromatography coupled with carbohydrate analysis identify high sugar concentrations present in the corn kernel solution after incubation that were not present in samples incubated with wild type tobacco extracts not containing E1 (see FIG. 17($a$)). The glucose peak in the corn sample incubated with E1 extracts is noticeably larger than the peak found in the corn sample incubated with wild type tobacco extract, though the wild type sample contains small amounts of an unidentified sugar. The small quantity of glucose produced from corn kernels incubated with wild type tobacco extract for 24 hours was not appreciably greater in kernels incubated in a citrate buffer (FIG. 17($b$)). The glucose dimer cellobiose was expected to be observed as the E1 endoglucanase functions by randomly cleaving the $\beta$-1,4-glycosidic bonds linking glucose molecules in cellulose. However, E1 does not effectively cleave the glycosidic bond linking two glucose molecules together, leaving a significant level of cellobiose intact. To maximize glucose yield in this experiment, a microbial cellobiose (Novo 188, Novozymes) was added to the E1 and wild type tobacco extracts to hydrolyze cellobiose to glucose.

To avoid the extra processing step of adding external cellulases to hydrolyze the cellulose in corn kernels, it is more efficient to produce the enzymes directly in the corn kernels. The present Applicants have developed transgenic corn lines expressing the E1 enzyme under the control of a constitutively active promoter. Western blot analysis clearly showed the presence of E1 protein in corn tissue from multiple lines (FIG. 13, lanes 1, 2, 5 and 6, top panel), and due to the nature of the promoter directing expression of the transgene E1 is also expected to be expressed and accumulate in the kernels.

The cellulose in corn grain is a more attractive feedstock than most lignocellulosic biomass due to its absence of lignin and the fact that harvesting and processing costs can be shared with existing ethanol production from starch in corn grain. The potential of increasing ethanol yields from corn grain has been demonstrated with a yield of 2.84 gallons of ethanol per bushel of corn when the cellulose was processed with starch, as compared with a yield of 2.58 gallons/bushel; from starch along (V. Singh et al., ASAE/CSAE Meeting Paper No. 046056, St. Joseph, Mich., 2004, ASAE), for a 10% increase in yield. A mid-sized ethanol plant can produce on the order of 100 million gallons of ethanol a year. If the cellulose fraction in corn kernels is also able to be converted to glucose and then fermented to ethanol, an additional 9 million gallons of ethanol could be produced each year, assuming an 80% efficiency of conversion (M. Gulati et al., Biores. Technol., 1996, 58: 253-264). Furthermore, by utilizing the cellulose to produce ethanol, the dried distillers grain with solubles (DDGS) will have a lower fiber and higher protein and fat content, making it more valuable. These benefits should be of significant interest to ethanol to co-ops and corn growers, as the increased ethanol production will lead to significant revenues at little additional cost to the producer if ethanol prices continue to remain around the current price of $2.90 a gallon as reported on Jun. 4, 2006. In addition, the use of corn crops containing cellulases to increase ethanol yields by also utilizing cellulose in corn grain will provide an important first market for enhanced crops engineered for cellulosic ethanol production.

One of the technical objectives to support this project is to demonstrate cellulose hydrolysis in corn grain engineered to express E1 endoglucanase. Preliminary data using E1 extracts from tobacco indicate that the E1 enzyme has the capability of hydrolyzing the cellulose fraction in corn kernels. Transgenic corn lines have been generated to express E1 under the control of a constitutive promoter, accumulating the enzyme in the kernel as well as in the rest of the plant. These E1 corn lines will be tested for conversion of cellulose in the corn kernel to glucose.

Another technical objective is to achieve a 4% increase in glucose yield by combining cellulose hydrolysis and starch hydrolysis in E1 corn. E1 corn grain will be processed under conditions standard for starch hydrolysis in the dry milling process. Treatment variables include physical processing of the kernel (e.g., particle mesh size), and reaction conditions such as pH, temperature, viscosity, processing times, and addition of amylase enzymes for starch hydrolysis. Successful results will demonstrate that the cellulose in corn kernels can be processed directly with the starch fraction, as opposed to being initially fractionated as in the wet milling process and then hydrolyzed separately, producing a target increase in glucose yield of 4% in comparison to wild type kernels. This demonstration is key to illustrating that glucose production from the cellulose from corn kernels can be incorporated relatively easily into the dry milling process.

Another technical objective is to produce ethanol from both the cellulosic and starch components in the E1 corn kernels. The glucose produced from the digestion of cellulose and starch in corn kernels will be used in a laboratory scale fermentation reaction to synthesize ethanol. Both positive and negative effects of cellulose hydrolysis by-products, such as pentose sugars, on ethanol yield will be determined.

More specifically, future work will include the following:
1. Characterization of the Level of Glucose Production from Cellulose in E1 Corn Kernels from Cellulosic Treatment Confirmation of the E1 activity from corn kernel extracts in vitro. E1 cellulase activity has been demonstrated in vitro in extracts from transgenic E1 tobacco and E1 corn leaves. E1 corn kernels have not yet been analyzed due to the immediate need to bulk up seeds of the transgenic corn lines, but transgenic corn plants are currently growing and will provide sufficient grain for these analyses. Carboxy-methyl-cellulose (CMC) is a synthetic cellulose molecule that is commercially available and commonly used to analyze cellulase activity (P. Beduin, Anal. Biochem., 1983, 131: 333-336) in conjunction with Congo Red, a dye that binds cellulose. When CMC is incorporated into agar plates in Petri dishes, cellulases can be applied to the plate that will degrade the CMC. These areas of degradation can clearly be seen by their lack of red staining when incubated with Congo Red. E1 corn kernels will be harvested from individual cobs so that each line can be analyzed separately. The cobs will be dried at 40° C. and then the kernels removed and ground to 20 mesh. Extracts from three 100 mg samples of E1 corn kernels from each cob will be assayed on CMC plates at 70° C. for cellulase activity, and all lines that demonstrate cellulase activity will be used for further characterization. The individual corn lines have already been analyzed for levels of E1 protein expression and the levels of cellulase activity will be compared with protein expression to investigate whether there is a direct correlation between enzyme levels and cellulase activity.

Analysis of glucose yield from E1 corn. As suggested by preliminary results showing that extracts from E1 tobacco increase glucose yields from corn kernels (FIG. 17(b)), the incorporation of the E1 endoglucanase into corn kernels is predicted to increase glucose recovery. This hypothesis will be tested by measuring levels of glucose after the ground corn kernels have incubated in citrate buffer, pH 5.0 at 80° C. for 24 hours. Glucose will be measured spectrophotometrically at a wavelength of 400 nm using a commercial test kit (Raichem) and through ion chromatography (Metrohm), which can also measure cellulose degradation products. Transgenic corn kernels will be compared with wild type kernels as a negative control and with cellulase AN, a commercially available cellulase cocktail (Novozymes) incubated under the recommended temperature of 55° C. Conditions such as temperature and incubation time will be investigated to identify conditions that produce the optimal yield of glucose.

2. Determination of Combined Glucose Production from Cellulose and Starch in E1 Corn Kernels Determination of E1 activity under typical reaction conditions for starch hydrolysis. The anticipated benefit from transgenic corn expressing E1 comes from the hypothesis that the cellulosic biomass can be processed without significant modifications to existing starch hydrolysis reaction conditions. The present Applicants will determine the optimal bench-scale reaction conditions and feedstock requirements necessary for the starch saccharification. The present Applicants will then determine the optimal way to incorporate the cellulase incubation step into the starch processing, which might involve modifying the cellulase reaction conditions. These conditions will be examined using E1 corn kernels as the feedstock to determine the amount of glucose that can be produced from the cellulose in corn kernels. Glucose production will be measured spectrophotometrically and by IC. To investigate whether starch and cellulose can be hydrolyzed simultaneously, E1 corn kernels will be incubated under conditions optimized for starch amylase activity, which are typically at a higher temperature and pH than E1's optimal conditions, and glucose levels measured.

Measurement of levels of glucose from E1 corn kernels treated to hydrolyze both cellulose and starch. The starch in corn grain is hydrolyzed in ethanol plants using a combination of glucoamylase and α-amylase enzymes. If the results obtained indicate that E1 is unable to function under the reaction conditions optimal for starch hydrolysis, then the cellulose in corn kernels will be hydrolyzed before amylase treatment to avoid possible denaturation of E1 at the higher temperature. Following incubation of the ground corn kernels under the conditions determined as previously described, α-amylase will be added to the reaction and after the α-amylase is complete glucoamylase will be added to complete the starch digestion. If results obtained indicate that the E1 enzyme can function effectively under the reaction conditions necessary for starch hydrolysis then the corn kernels will solely undergo the incubation steps necessary for amylase activity. The E1 corn kernels will be used as a feedstock to evaluate the yield of glucose obtained from utilizing both starch and cellulose as sources of glucose. The use of the endogenous E1 enzyme will be compared with the addition of external cellulase AN enzymes and the basal level of glucose production from wild type corn kernels without the presence of cellulases.

3. Production of Ethanol from E1 Corn Kernels at a Benchtop Scale.

To confirm that cellulose in E1 corn kernels can be converted to glucose without interfering with downstream processes to synthesize ethanol, biomass from E1 corn kernels will be used to produce laboratory scale quantities of ethanol. Following glucose quantification from E1 corn kernels, the remaining solution will be autoclaved, and then incubated in an anaerobic fermentation system with an innoculum of *Saccharomyces cerevisiae* to convert the glucose to ethanol. Samples from the fermentation reaction will be removed after 48 hours and ethanol concentrations determined spectrophotometrically using alcohol dehydrogenase (L. Kristoffersen et al., J. Anal. Tox., 2005, 29: 66-79). In the presence of ethanol, the alcohol dehydrogenase enzyme reduces nicotinamide adenine dinucleotide (NAD) to NADH, which can be measured spectrophotometrically at 340 nm.

Future work will also include: (1) screening multiple corn lines for high cellulase and hemicellulase expression; (2) demonstrating a total increase of 9% in ethanol yield over current dry mill production by combining cellulase and hemicellulase traits in corn grain; (3) investigating the possibility of using corn cobs as a source of cellulosic material; (4) conducting a field trial with the engineered corn to demonstrate good grain yields under field conditions and to bulk up grain for subsequent processing; and (5) testing engineered corn seed for ethanol yield under actual dry mill processing conditions.

Example 7

Increased Glucose Conversion from Transgenic Biomass

E1 and wild-type samples were air-dried to a moisture content of 16% and then subsets of the biomass were AFEX (i.e., Ammonia Fiber Explosion) pre-treated according to standard techniques. The untreated and AFEX treated samples underwent concurrent hydrolysis reaction with the addition of the external cellulase enzymes, Spezyme and Novo 188. The reactions were incubated at 50° C. for 24 hours before determination of the glucose levels present.

Figure 19:
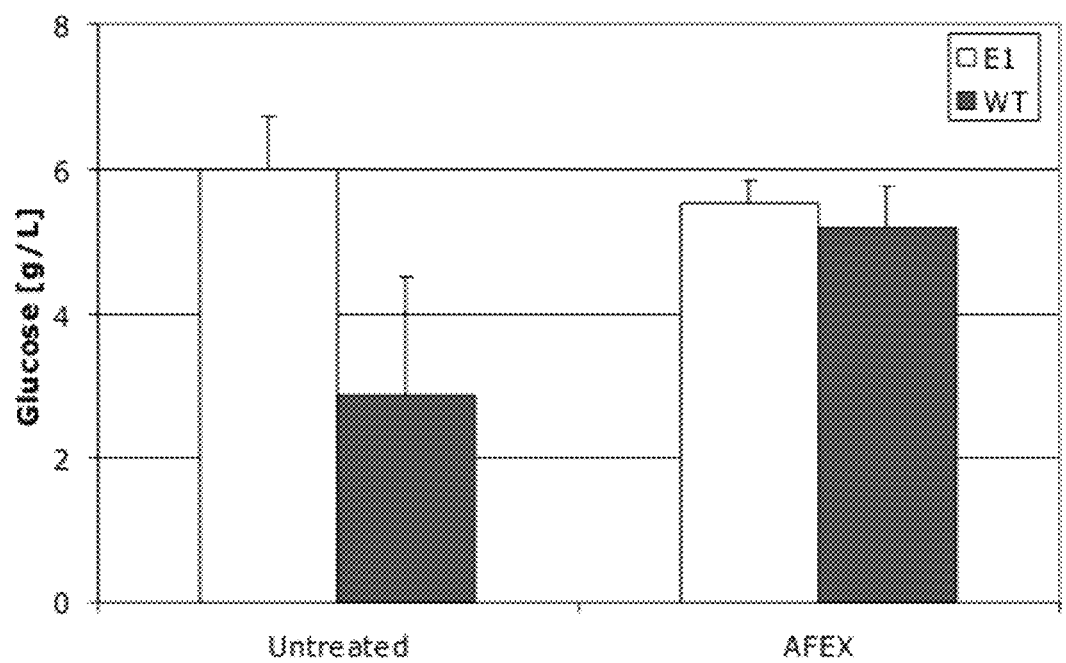
FIG. 19 is a graph illustrating the increased production of glucose from hydrolysis of transgenic tobacco biomass expressing the E1 endoglucanase compared to wild-type biomass. Glucose levels were measured from E1 and wild-type samples (see Example 7) before and after AFEX (ammonia fiber explosion) treatment.

Results are presented on FIG. 19. Increased levels of glucose were observed from hydrolysis of transgenic tobacco biomass expressing the E1 endoglucanase compared with wild-type biomass. Untreated E1 tobacco produced a greater level of glucose compared to wild-type biomass (6.0 g/L vs. 2.9 g/L). The level of glucose produced from untreated E1 tobacco was similar to that of AFEX pre-treated biomass, suggesting that the incorporation of cellulase enzymes could lessen or eliminate the need for chemical pre-treatment. (ammonia fiber explosion)

Example 8

Codon Optimized Gene Sequences for Expression of Microbial Cellulases in Plants

As already mentioned above, a method was developed to modify microbial genes for increased expression in plants. A composite plant codon usage table was constructed from the analysis of the sequenced genomes of *Zea mays*, *Arabidopsis thaliana*, and *Nicotiana tabacum*. The codon usage of each of those genomes were averaged together to obtain a composite codon usage from monocot and dicot plants, and this composite table was used as a template to modify microbial DNA sequences so that the microbial sequences have a codon usage better suited for expression in plants.

For increased transcriptional expression of the E1 endoglucanase from *Acidothermus cellulolyticus* (accession number U33212) in plants, the microbial sequence of the gene was optimized using a composite plant codon usage table. The average codon usages in *Zea mays* and *Arabidopsis thaliana* were obtained from the Kazusa Codon Usage Database and averaged together to produce the composite plant codon usage table. With optimization, the E1 sequence used for transformation into plants had SEQ ID NO. 1 as follows:

ATGGGCTTCGTTCTCTTTTCTCAACTCCCCTCCTTCCTTCTCGTTTCTAC

TCTTCTTCTGTTCCTCGTAATCTCACATTCATGTCGCGCCGCAGGCGGTG

GTTATTGGCATACTTCCGGCAGAGAGATACTTGACGCTAACAACGTTCCC

GTACGCATCGCTGGTATTAATTGGTTTGGTTTCGAGACGTGCAATTATGT

CGTTCACGGTCTTTGGTCTCGCGATTACCGTTCAATGCTGGATCAAATAA

AATCTCTCGGCTACAATACAATTCGCCTTCCCTACTCGGATGATATCTTG

AAACCAGGTACTATGCCCAACTCAATTAATTTTTATCAAATGAATCAAGA

CCTTCAAGGCCTGACATCCCTTCAAGTTATGGACAAGATAGTTGCTTACG

CAGGACAAATAGGACTTAGGATTATTCTCGACAGACACAGACCCGACTGC

TCTGGCCAAAGCGCTCTCTGGTATACTTCATCCGTCAGTGAAGCTACCTG

GATCTCTGATCTTCAAGCACTTGCCCAACGTTACAAAGGAAACCCTACTG

TTGTTGGTTTCGATCTTCACAACGAACCTCACGATCCCGCCTGTTGGGGC

TGCGGAGACCCATCTATTGACTGGAGATTGGCCGCCGAACGTGCTGGCAA

CGCAGTGCTGTCCGTAAATCCCAACCTGCTTATATTTGTCGAAGGCGTAC

AATCCTATAATGGTGACTCCTATTGGTGGGGCGGAAACTTGCAAGGCGCA

GGACAGTATCCAGTTGTCCTCAATGTCCCGAATCGTCTCGTTTACTCAGC

ACACGACTACGCTACTTCCGTATACCCGCAAACTTGGTTCAGCGACCCGA

CATTCCCAAATAACATGCCCGGTATCTGGAATAAAAATTGGGGTTATCTC

TTCAACCAAAACATCGCGCCCGTTTGGCTTGGAGAATTCGGCACTACTCT

GCAATCGACTACAGACCAAACTTGGCTCAAGACTCTTGTCCAGTACCTCA

GACCTACAGCACAATACGGAGCAGACTCATTTCAATGGACATTTTGGTCC

TGGAACCCGGATTCTGGCGATACTGGCGGTATTCTTAAAGATGATTGGCA

AACTGTTGACACTGTCAAGGACGGCTACCTCGCACCTATCAAATCCTCGA

TATTCGATCCAGTTGGC

Genes encoding putative family 48 glycoside hydrolase (accession number YP872376) and family 10 glycoside hydrolase (accession number YP871941) enzymes, which were identified from the sequencing of the *Acidothermus cellulolyticus* genome, were also codon-optimized for increased transcriptional expression in corn. After optimization using the average codon usage table for *Zea mays*, the following sequence (SEQ ID NO. 2) for the family 48 enzyme was used for expression in plants:

ATGCCCGGCCTCCGAAGACGCCTGAGAGCTGGAATCGTGAGCGCGGCTGC

ACTTGGGTCTCTGGTCTCTGGGCTCGTCGCTGTCGCGCCCGTCGCCCACG

CCGCTGTTACGTTGAAAGCACAATATAAGAATAATGATTCCGCCCCCTCC

GACAATCAGATTAAGCCTGGACTCCAGCTTGTGAATACTGGTTCTTCCTC

AGTTGATCTCTCAACGGTCACTGTAAGGTACTGGTTTACTCGTGATGGCG

GTTCATCAACGCTCGTGTACAATTGCGACTGGGCCGCGATGGGCTGCGGT

AACATCCGCGCGTCATTCGGATCAGTTAACCCTGCCACGCCCACTGCCGA

CACGTACCTGCAGCTGTCCTTCACTGGTGGCACACTGGCTGCAGGAGGCT

CTACTGGCGAAATCCAAAACCGGGTGAACAAGAGCGATTGGTCTAACTTC

GATGAGACCAATGACTACTCTTATGGCACTAACACCACTTTCCAGGATTG

GACTAAGGTAACCGTGTACGTGAATGGTGTCCTCGTCTGGGGAACAGAAC

CGTCAGGAGCTACCGCATCCCCTTCAGCTTCAGCTACTCCTTCGCCATCC

AGCTCGCCGACAACAAGTCCATCTTCATCTCCCAGTCCAAGCAGTTCACC

```
TACGCCAACACCTTCCTCAAGTTCTCCACCCCCATCCAGCAATGATCCAT
ATATTCAAAGGTTTCTCACCATGTACAACAAGATTCACGATCCAGCCAAC
GGCTACTTCTCACCCCAGGGCATACCCTACCACAGCGTCGAAACTCTCAT
CGTCGAGGCTCCTGACTACGGGCACGAAACTACATCGGAAGCCTACTCGT
TTTGGCTCTGGCTAGAGGCTACCTACGGTGCGGTTACCGGCAATTGGACT
CCGTTCAACAACGCGTGGACGACCATGGAGACGTACATGATTCCACAACA
TGCCGATCAACCGAACAATGCCTCTTATAACCCGAACAGTCCTGCTTCAT
ATGCACCAGAAGAACCGCTGCCATCTATGTATCCCGTCGCAATCGATTCT
TCAGTGCCAGTTGGTCATGATCCACTCGCAGCAGAGTTGCAATCTACATA
TGGAACCCCCGATATTTATGGGATGCACTGGTTGGCCGACGTGGACAACA
TTTATGGCTATGGCGACTCTCCAGGAGGCGGATGCGAGCTTGGTCCTTCA
GCGAAAGGCGTATCTTATATCAACACCTTCCAGCGGGGTAGTCAAGAGAG
TGTCTGGGAAACAGTTACACAGCCTACGTGCGACAACGGAAAGTACGGTG
GGGCTCATGGTTACGTCGATCTTTTCATCCAGGGATCAACACCACCGCAA
TGGAAATATACGGACGCACCCGATGCTGACGCGCGGGCCGTGCAGGCAGC
ATACTGGGCGTACACCTGGGCAAGTGCGCAAGGCAAAGCTTCCGCAATCG
CCCCTACAATAGCCAAGGCTGCTAAATTGGGTGACTATCTTCGATACTCT
CTCTTCGATAAATACTTCAAACAGGTGGGCAACTGTTATCCTGCCAGTTC
GTGCCCAGGCGCCACCGGAAGACAGTCTGAAACATACCTGATTGGATGGT
ATTATGCTTGGGGTGGAAGTTCTCAGGGCTGGGCTTGGCGCATCGGTGAT
GGCGCTGCTCATTTTGGATACCAAAACCCACTTGCGGCCTGGGCCATGTC
AAACGTCACTCCACTTATCCCGCTGTCCCCCACCGCAAAGAGCGACTGGG
CCGCCTCTCTCCAGCGCCAATTGGAGTTCTACCAGTGGCTGCAATCAGCA
GAAGGTGCTATTGCGGGCGGGGCTACCAATTCCTGGAACGGCAACTATGG
CACACCTCCAGCTGGTGACTCTACATTTTACGGCATGGCGTACGATTGGG
AACCTGTTTATCACGACCCCCCTTCTAATAATTGGTTCGGCTTTCAAGCA
TGGTCCATGGAGAGAGTCGCTGAGTACTACTACGTTACAGGCGACCCAAA
AGCCAAGGCCCTGCTAGATAAGTGGGTTGCTTGGGTCAAGCCAAACGTAA
CTACAGGCGCATCATGGTCTATCCCATCCAATCTGTCCTGGTCTGGCCAA
CCAGATACCTGGAATCCATCCAACCCGGGGACCAACGCGAACCTCCATGT
CACTATAACCTCTTCGGGACAAGATGTCGGCGTGGCCGCGGCTCTTGCAA
AAACGTTGGAGTACTACGCCGCGAAGTCCGGAGACACCGCGTCCAGAGAT
TTGGCCAAAGGCCTCCTCGATAGCATTTGGAACAATGATCAAGACAGCTT
GGGAGTAAGCACGCCAGAGACAAGGACTGACTATTCCCGCTTTACTCAAG
TTTACGACCCGACCACCGGCGATGGCCTCTATATTCCTTCTGGCTGGACA
GGTACTATGCCCAACGGCGACCAAATCAAGCCAGGCGCTACATTTCTTTC
CATTCGCTCGTGGTATACGAAGGACCCTCAATGGTCAAAGGTTCAGGCAT
ATCTTAACGGCGGCCCTGCACCAACCTTTAATTACCACAGGTTCTGGGCC
GAATCTGATTTCGCCATGGCTAACGCTGACTTCGGTATGCTCTTCCCATC
TGGAAGCCCGTCACCAACCCCCTCACCTACTCCTACATCTTCGCCCTCCC
CGACGCCTTCGTCTTCACCAACACCCTCTCCCTCCCCCTCTCCTACCGGC
GACACAACTCCGCCTAGTGTGCCCACCGGGCTCCAGGTCACCGGCACCAC
AACGTCATCAGTCAGCCTGTCTTGGACCGCATCTACCGACAACGTTGGTG
TGGCTCATTACAACGTTTATAGGAATGGCACTTTGGTCGGACAGCCAACC
GCGACATCTTTCACCGACACTGGTTTGGCGGCGGGAACCTCTTACACTTA
TACAGTAGCTGCTGTGGACGCTGCAGGTAATACCTCTGCACAATCTAGCC
CAGTGACCGCCACAACCGCCTCTCCCTCCCCTTCACCATCGCCTTCTCCC
ACACCTACTTCATCACCATCCCCCACACCTAGCCCTACCCCCTCTCCAAC
ATCAACATCGGGCGCATCGTGCACCGCCACATACGTAGTCAACTCCGATT
GGGGCTCCGGTTTCACCACAACTGTTACTGTGACCAACACTGGCACCCGT
GCGACTTCCGGCTGGACGGTTACGTGGTCCTTCGCTGGCAATCAAACCGT
TACAAACTACTGGAATACCGCACTCACGCAGTCGGGCAAGAGTGTCACGG
CCAAAAACCTCAGCTATAATAATGTTATCCAACCAGGGCAGTCTACGACC
TTCGGATTCAACGGTTCCTATTCGGGACAAATACCGCTCCTACACTCAG
TTGTACTGCCTCCTAA
```

After codon optimization the following sequence (SEQ ID NO. 3) for the family 10 enzyme was used for expression in plants:

```
ATGCACCATGCTATGCGGCGTATGGTAACATCTGCCTCAGTTGTCGGCGT
CGCTACTCTGGCGGCCGCTACCGTCCTTATCACAGGAGGAATCGCCCATG
CCGCATCTACTCTAAAGCAGGGAGCCGAAGCTAATGGAAGATATTTTGGA
GTCTCAGCTTCCGTGAATACCCTTAACAATAGTGCCGCAGCAAATCTTGT
CGCAACCCAATTCGACATGCTTACCCCAGAGAACGAGATGAAATGGGATA
CAGTGGAAAGCTCCAGAGGTTCCTTTAATTTCGGGCCAGGAGATCAAATC
GTTGCATTTGCTACAGCCCATAATATGCGCGTTAGAGGGCATAATCTGGT
ATGGCATTCTCAACTTCCAGGATGGGTCTCGTCACTTCCACTGAGCCAGG
TGCAGTCTGCTATGGAGAGTCATATCACAGCAGAGGTCACGCACTACAAG
GGCAAAATATACGCATGGGACGTTGTGAACGAGCCTTTTGATGACTCTGG
TAACCTTCGTACAGATGTTTTCTACCAGGCAATGGGTGCAGGGTACATCG
CTGACGCTCTGCGAACTGCGCATGCTGCTGACCCAAACGCAAAGCTCTAC
CTTAACGACTATAATATTGAGGGTATTAACGCTAAAAGTGACGCTATGTA
CAACCTCATCAAACAACTTAAGTCACAGGGAGTCCCTATTGATGGCGTAG
GATTCGAAAGCCACTTCATTGTGGGCCAAGTGCCCTCCACACTCCAACAG
AATATGCAGCGTTTTGCTGATCTCGGAGTCGATGTTGCCATAACAGAATT
AGATGACAGGATGCCTACTCCGCCTTCCCAACAAAACCTTAATCAACAGG
CCACCGATGATGCTAACGTGGTAAAAGCTTGCTTGGCGGTTGCTCGATGT
GTAGGAATTACACAGTGGGATGTAAGCGACGCAGATTCTTGGGTTCCTGG
CACCTTCTCAGGTCAGGGCGCCGCAACTATGTTTGATAGCAATTTACAAC
CAAAGCCTGCTTTCACTGCCGTCTTGAACGCGCTTTCTGCATCCGCCTCT
GTATCACCTTCTCCGTCCCCGTCACCCTCCCCTTCTCCAAGCCCATCTCC
GTCACCATCACCTTCACCTAGCCCATCACCATCTCCATCACCTTCCCCTT
CCTCTTCTCCAGTCAGTGGCGGTGTTAAAGTTCAATATAAGAATAACGAT
```

```
TCCGCTCCGGGAGACAACCAGATAAAACCTGGCCTGCAAGTAGTTAATAC

TGGATCGTCATCGGTTGATCTGAGTACGGTTACCGTTAGATACTGGTTCA

CACGAGACGGAGGATCTTCCACATTGGTTTACAATTGCGACTGGGCTGTT

ATGGGTTGTGGTAATATTCGCGCTAGCTTTGGATCAGTTAATCCAGCAAC

CCCTACGGCTGATACGTATCTACAACTCTCCTTCACAGGAGGCACACTAC

CCGCAGGAGGATCAACCGGTGAGATACAGTCCAGGGTTAACAAAAGCGAC

TGGTCAAACTTCACTGAGACCAATGACTACAGCTATGGTACTAACACCAC

CTTCCAAGATTGGTCAAAGGTCACTGTATACGTTAATGGTCGATTGGTCT

GGGGCACCGAACCTTCCGGAACATCCCCCTCTCCAACACCATCTCCTAGT

CCAACCCCATCTCCAAGCCCTTCCCCATCTCCCAGTCCTTCACCTTCGCC

ATCCCCCTCACCATCCCCATCTCCGTCTTCTTCTCCGAGTTCGGGCTGCG

TGGCATCTATGAGAGTTGATTCTAGCTGGCCTGGCGGTTTTACAGCCACT

GTTACTGTGTCCAACACTGGAGGCGTCTCTACTTCAGGCTGGCAAGTTGG

CTGGAGCTGGCCTTCAGGCGATAGTTTAGTAAACGCGTGGAATGCAGTTG

TTTCTGTTACAGGTACCAGTGTTAGAGCTGTGAATGCAAGCTATAATGGA

GTGATCCCCGCAGGAGGATCAACCACTTTCGGTTTCCAGGCGAATGGCAC

ACCAGGCACACCGACGTTTACTTGTACTACCTCAGCAGATCTCTAA.
```

Example 9

Figure 20:
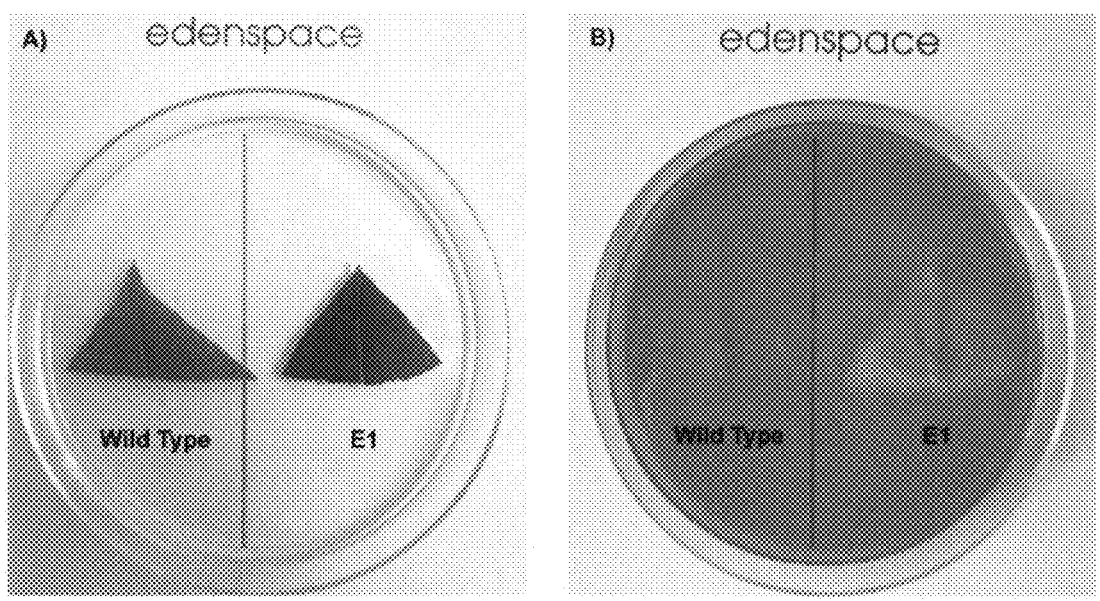
FIG. 20 shows two pictures allowing visualization of E1 hydrolysis of CMC (carboxyl-methyl-cellulose) using Congo Red staining. Leaf tips of untransformed (left) and transgenic E1 (right) tobacco (A) before and (B) after incubation at 65° C. for thirty minutes and the staining with Congo Red.

Screening Method for the Rapid Identification of Microbial Cellulase Enzymes that can Function in Plants Purified cellulose substrate carboxyl-methyl cellulose (CMC) was used with agar to form a solid media that was poured into Petri dishes. As already mentioned above, when hydrolyzed by cellulase enzymes, such as E1 endoglucanase from *Acidothermus cellulolyticus*, CMC is not longer reactive to the dye Congo Red. Transgenic tobacco biomass expressing the E1 gene were placed directly on the surface of the CMC plates and allowed to incubate at 65° C. for thirty minutes. This temperature is near the optimal temperature for E1 activity (Z. Dai et al., Mol. Breeding, 2000, 6: 277-285; Z. Dai et al., Transg. Res., 2000, 9: 43-54) and does not cause melting of the CMC plate. After incubation, the tobacco biomass was removed and the CMC plate was flooded with Congo Red to stain the cellulose in the media. In contrast to wild-type untransformed tobacco leaves (see FIG. 20A), E1 tobacco leaves were observed to clearly hydrolyze the adjacent CMC, preventing Congo Red from staining the media and producing a clear, leaf-shaped zone (see FIG. 20B).

This method can be used to quickly assess the cellulase activity of enzymes (e.g., microbial enzymes) transiently expressed by samples of leaves (or other plant tissues).

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method of saccharification comprising steps of:
   treating a plant part obtained from at least one transgenic plant with at least one thermostable lignocellulolytic enzyme, wherein the thermostable lignocellulolytic enzyme is expressed from a transgene present in the at least one transgenic plant, under conditions to activate the at least one thermostable lignocellulolytic enzyme thereby deconstructing lignocellulose to form a hydrolysate mixture; and
   incubating the hydrolysate mixture under conditions that promote conversion of fermentable sugars of the hydrolysate mixture,
   wherein the genome of the at least one transgenic plant is augmented with:
   a recombinant polynucleotide encoding the at least one thermostable lignocellulolytic enzyme operably linked to a promoter sequence,
   wherein the at least one thermostable lignocellulolytic enzyme exhibits optimal activity at a temperature greater than about 50° C.,
   wherein the at least one thermostable lignocellulolytic enzyme is produced at a level greater than 0.5% total soluble protein, greater than 5% total protein, greater than 10% total soluble protein, or greater than 20% total soluble protein, and
   wherein, prior to the treating step, the plant part is not pretreated or is pretreated under conditions of less heat or less acid, or that are otherwise less harsh or produce fewer toxic by-products than conditions used in pretreatment of biomass from non-transgenic plants.

2. The method of claim 1, wherein the plant part is substantially free of soil dirt.

3. The method of claim 1, wherein the plant part is pretreated by heating the plant part to a temperature greater than 50° C., greater than 75° C. or greater than 100° C.

4. The method of claim 1, wherein the plant part is pretreated by adding water to the hydrolysate mixture.

5. The method of claim 1, wherein the plant part is pretreated by chopping, grinding, shredding or pulverizing the plant part.

6. The method of claim 1 further comprising adding external lignocellulolytic enzymes to the plant part prior to the treating step.

7. The method of claim 1, wherein the method results in increased sugar or ethanol production compared to a method in which the plant part is obtained from a non-transgenic plant.

8. The method of claim 1 further comprising removing at least one unfermentable component from the hydrolysate.

9. The method of claim 8, wherein removing the at least one unfermentable component speeds up conversion of fermentable sugars.

10. The method of claim 8, wherein the at least one unfermentable component is selected from the group consisting of lignin, lignin-breakdown products, phenols, furans, and combinations thereof.

11. The method of claim 8, wherein removing the at least one unfermentable component from the hydrolysate mixture comprises separating/isolating and purifying the at least one unfermentable component.

12. The method of claim 10, wherein the at least one unfermentable component is phenol.

13. The method of claim 8, wherein the at least one unfermentable component, or a derivative thereof, is burned to produce heat or electricity.

14. The method of claim 13, wherein the heat produced is used in said method.

15. The method of claim 1 further comprising a step of:
    distilling the ethanol produced by conversion of fermentable sugars of the hydrolysate mixture so as to obtain distilled ethanol.

16. The method of claim 15, wherein at least one unfermentable component is added to distilled ethanol as a denaturant.

17. The method of claim 15, wherein at least one unfermentable component is added to ethanol produced by conversion of fermentable sugars of the hydrolysate mixture prior to the distilling step, is distilled with the ethanol, and remains in the distilled ethanol as a denaturant.

18. The method of claim 15, wherein at least one unfermentable component is processed into one or more compounds that can be used as denaturants.

19. The method of claim 18, wherein the one or more compounds that can be used as denaturants comprise alcohols.

20. The method of claim 19, wherein the one or more compounds that can be used as denaturants are selected from the group consisting of methanol and butanol.

21. The method of claim 1, wherein the distilled ethanol comprises one or more unfermentable components that act as denaturants.

22. The method of claim 15, wherein the method further produces a by-product that has higher food value than a by-product produced in a method using a plant part obtained from a non-transgenic plant.

23. The method of claim 22, wherein the by-product comprises dried distillers grain (DDG) that has increased levels of protein or oil, resulting from hydrolysis or removal of cellulose or hemicellulose or breakdown or removal of lignin.

24. The method of any one of claim 1 or 15 further comprising adding microorganisms to the plant part so as to induce simultaneous saccharification and fermentation.

25. The method of claim 24, wherein the microorganisms ferment six-carbon sugars or five-carbon sugars or both.

26. The method of any one of claim 1 or 15, wherein the step of incubating the hydrolysate mixture under conditions that promote conversion of fermentable sugars of the hydrolysate mixture comprises adding microorganisms to the hydrolysate mixture.

27. The method of claim 26, wherein the microorganisms ferment six-carbon sugars or five-carbon sugars or both.

28. The method of claim 1, wherein the plant part comprises plant parts obtained from two or more transgenic plants, wherein the transgenic plants are of the same or different species and produce the same or different lignocellulolytic enzymes.

29. The method of claim 28, wherein the plant parts are co-processed so as to combine the lignocellulolytic enzymes in a desired proportion to increase yield.

30. The method of claim 29, wherein the plant parts are co-processed so as to combine the lignocellulolytic enzymes in a desired proportion to increase yield by achieving more efficient hydrolysis of polysaccharides and breakdown and removal of lignin.

31. The method of claim 1 wherein the plant part comprises plant parts obtained from at least one transgenic plant and plant parts obtained from a non-transgenic plant, and the method is carried out using common equipment and facilities for harvesting, ensilement, chopping, crushing, milling, liquefaction, saccharification, fermentation, distillation, drying, storage or transportation.

32. The method of claim 1, wherein the plant part is selected from the group consisting of corn grain, corn stover, and combinations thereof.

33. The method of claim 1, wherein the genome of the transgenic plant is further augmented with one or more yeast genes to promote simultaneous saccharification and fermentation.

34. The method of claim 1 further comprising a step of: treating the plant part under conditions that promote starch hydrolysis.

35. The method of claim 34, wherein the step of treating the plant part under conditions that promote starch hydrolysis comprises using at least one amylase enzyme.

36. The method of claim 35, wherein the at least one amylase enzyme is selected from the group consisting of glucoamylase, a-amylase, and combinations thereof.

37. The method of claim 34, wherein the step of treating the plant part under conditions to activate the at least one lignocellulolytic enzyme and the step of treating the plant part under conditions to promote starch hydrolysis are performed simultaneously.

38. The method of claim 34, wherein the step of treating the plant part under conditions to activate the at least one lignocellulolytic enzyme and the step of treating the plant part under conditions to promote starch hydrolysis are performed sequentially.

39. The method of claim 34, wherein the method is carried out using common equipment and facilities for harvesting, ensilement, chopping, crushing, milling, liquefaction, saccharification, fermentation, distillation, drying, storage or transportation.

40. The method of claim 34, wherein the plant part comprises plant parts obtained from two or more transgenic plants, wherein the transgenic plants are of the same or different species and produce the same or different lignocellulolytic enzymes.

41. The method of claim 34, wherein the plant part comprises plant parts obtained from at least one transgenic plant and plant parts obtained from a nontransgenic plant.

42. The method of claim 34, wherein the plant part comprises one or more of corn grain, corn fiber and corn stover.

43. The method of claim 34, wherein the plant part comprises corn grain.

44. The method of claim 42, wherein the method is part of a dry milling process.

45. The method of claim 1, wherein the at least one thermostable lignocellulolytic enzyme is selected from the group consisting of a cellulase, a hemicellulase, a ligninase, and combinations thereof.

46. The method of claim 1, wherein the plant part is obtained from at least one transgenic plant, the genome of which is augmented with at least a first recombinant polynucleotide and a second recombinant polynucleotide,
the first recombinant polynucleotide encoding at least a first lignocellulolytic
enzyme operably linked to a first promoter sequence, and
the second recombinant polynucleotide encoding at least a second lignocellulolytic enzyme operably linked to a second promoter sequence,
wherein the first and second lignocellulolytic enzymes are each independently produced at a level greater than 0.5% total soluble protein, greater than 5% total soluble protein, greater than 10% total soluble protein or greater than 20% total soluble protein.

47. The method of claim 46, wherein the lignocellulolytic enzymes are each independently selected from the group consisting of a cellulase, a hemicellulase, a ligninase, and any combination thereof.

48. The method of claim 46, wherein the lignocellulolytic enzymes are each independently selected from the group consisting of a cellobiohydrolase, an endoglucanase, a β-D-glucosidase, a xylanase, an arabinofuranosidase, an acetyl xylan esterase, a glucuronidase, a mannanase, a galactanase, an arabinase, a lignin peroxidase, a manganese-dependent peroxidase, a hybrid peroxidase, a laccase, and any combination thereof.

49. The method of claim 46, wherein the lignocellulolytic enzymes comprise an endoglucanase and an endoxylanase, an endoglucanase and a glycoside hydrolase, an endoglucanase and a lignin-peroxidase, an endoxylanase and a glycoside hydrolase, an endoxylanase and a lignin-peroxidase or a glycoside hydrolase and a ligninperoxidase.

50. The method of claim 49, wherein the endoglucanase comprises E 1 endo-1,4-β-glucanase.

51. The method of claim 1, wherein the recombinant polynucleotide comprises a codon optimized polynucleotide encoding E1 endoglucanase, wherein the codon optimized polynucleotide encodes a polypeptide whose sequence comprises the sequence of SEQ ID NO: 4, wherein the codon optimized polynucleotide is optimized for expression in more than one plant.

52. The method of claim 1, wherein the recombinant polynucleotide comprises a codon optimized polynucleotide encoding the family 48 glycoside hydrolase, wherein the codon optimized polynucleotide encodes a polypeptide whose sequence comprises the sequence of SEQ ID NO: 5, wherein the codon optimized polynucleotide is optimized for expression in more than one plant.

53. The method of claim 1, wherein the recombinant polynucleotide comprises a codon optimized polynucleotide encoding family 10 glycoside hydrolase, wherein the codon optimized polynucleotide encodes a polypeptide whose sequence comprises the sequence of SEQ ID NO: 6, wherein the codon optimized polynucleotide is optimized for expression in more than one plant.

54. The method of any one of claim 51, 52 or 53, wherein the codon optimized polynucleotide is optimized for expression in maize, arabidopsis, and tobacco.

55. The method of claim 1, wherein the at least one thermostable lignocellulolytic enzyme is expressed constitutively or tissue-specifically.

56. The method of claim 1, wherein the at least one thermostable lignocellulolytic enzyme is expressed in a targeted sub-cellular compartment or organelle.

57. The method of claim 1, wherein the plant is a monocotyledonous plant.

58. The method of claim 1, wherein the plant is a dicotyledonous plant.

59. The method of claim 1, wherein the plant is a crop plant.

60. The method of claim 1, wherein the plant is selected from the group consisting of corn, switchgrass, sorghum, miscanthus, sugarcane, poplar, pine, wheat, rice, soy, cotton, barley, turf grass, tobacco, bamboo, rape, sugar beet, sunflower, willow, and eucalyptus.

61. The method of claim 1, the genome of which is further augmented with:
a recombinant polynucleotide encoding at least one amylase enzyme operably linked to a promoter sequence, wherein the polynucleotide is optimized for expression in the plant.

62. The method of claim 61, wherein the amylase enzyme comprises alpha amylase enzyme or glucoamylase enzyme.

63. The method of claim 1, the genome of which is further augmented with:
a recombinant polynucleotide encoding at least one enzyme for converting hard-to-ferment sugars to more easily fermentable sugars operably linked to a promoter sequence, wherein the polynucleotide is optimized for expression in the plant.

64. The method of claim 63, wherein the enzyme comprises an isomerase that converts xylose to xylulose.

65. The method of claim 1, the genome of which is further altered so as to minimize dispersal of the transgenes through plant reproduction.

66. The method of claim 65, the genome of which is altered so as to introduce male sterility in the plant or to delay plant flowering.

67. The method of claim 1, the genome of which is further altered so as to reduce the amount of one or more forms of lignin in the transgenic plant relative to cellulose and hemicellulose.

68. The method of claim 1, the genome of which is further altered so as to increase the amount of one or more forms of cellulose in the transgenic plant relative to lignin and hemicellulose.

69. The method of claim 1, the genome of which is further altered so as to increase the amount of one or more forms of hemicellulose in the transgenic plant relative to lignin and cellulose.

70. The method of claim 51, wherein the sequence of the codon optimized polynucleotide comprises the sequence of SEQ ID NO: 1.

71. The method of claim 52, wherein the sequence of the codon optimized polynucleotide comprises the sequence of SEQ ID NO: 2.

72. The method of claim 53, wherein the sequence of the codon optimized polynucleotide comprises the sequence of SEQ ID NO: 3.

73. The method of claim 1, wherein one or more unfermentable components is processed into butanol or methanol.

* * * * *

SEQUENCE LISTING

<160> NUMBER OF SEQ ID NOS: 6

<210> SEQ ID NO 1
<211> LENGTH: 1167
<212> TYPE: DNA
<213> ORGANISM: Artificial Sequence
<220> FEATURE:
<223> OTHER INFORMATION: Acidothermus cellulolyticus

<400> SEQUENCE: 1

```
atgggcttcg ttctcttttc tcaactcccc tccttccttc tcgtttctac tcttcttctg      60
ttcctcgtaa tctcacattc atgtcgcgcc gcaggcggtg gttattggca tacttccggc     120
agagagatac ttgacgctaa caacgttccc gtacgcatcg ctggtattaa ttggtttggt     180
ttcgagacgt gcaattatgt cgttcacggt ctttggtctc gcgattaccg ttcaatgctg     240
gatcaaataa aatctctcgg ctacaataca attcgccttc cctactcgga tgatatcttg     300
aaaccaggta ctatgcccaa ctcaattaat ttttatcaaa tgaatcaaga ccttcaaggc     360
ctgacatccc ttcaagttat ggacaagata gttgcttacg caggacaaat aggacttagg     420
attattctcg acagacacag acccgactgc tctggccaaa gcgctctctg gtatacttca     480
tccgtcagtg aagctacctg gatctctgat cttcaagcac ttgcccaacg ttacaaagga     540
aaccctactg ttgttggttt cgatcttcac aacgaacctc acgatcccgc ctgttggggc     600
tgcggagacc catctattga ctggagattg gccgccgaac gtgctggcaa cgcagtgctg     660
tccgtaaatc ccaacctgct tatatttgtc gaaggcgtac aatcctataa tggtgactcc     720
```

```
tattggtggg gcggaaactt gcaaggcgca ggacagtatc cagttgtcct caatgtcccg    780
aatcgtctcg tttactcagc acacgactac gctacttccg tatacccgca aacttggttc    840
agcgacccga cattcccaaa taacatgccc ggtatctgga ataaaaattg gggttatctc    900
ttcaaccaaa acatcgcgcc cgtttggctt ggagaattcg gcactactct gcaatcgact    960
acagaccaaa cttggctcaa gactcttgtc cagtacctca gacctacagc acaatacgga   1020
gcagactcat ttcaatggac attttggtcc tggaacccgg attctggcga tactggcggt   1080
attcttaaag atgattggca aactgttgac actgtcaagg acggctacct cgcacctatc   1140
aaatcctcga tattcgatcc agttggc                                       1167

<210> SEQ ID NO 2
<211> LENGTH: 3366
<212> TYPE: DNA
<213> ORGANISM: Artificial Sequence
<220> FEATURE:
<223> OTHER INFORMATION: Acidothermus celluloyticus

<400> SEQUENCE: 2
atgcccggcc tccgaagacg cctgagagct ggaatcgtga gcgcggctgc acttgggtct     60
ctggtctctg ggctcgtcgc tgtcgcgccc gtcgccacg ccgctgttac gttgaaagca    120
caatataaga ataatgattc cgcccccctcc gacaatcaga ttaagcctgg actccagctt    180
gtgaatactg gttcttcctc agttgatctc tcaacggtca ctgtaaggta ctggtttact    240
cgtgatggcg gttcatcaac gctcgtgtac aattgcgact gggccgcgat gggctgcggt    300
aacatccgcg cgtcattcgg atcagttaac cctgccacgc ccactgccga cacgtacctg    360
cagctgtcct tcactggtgg cacactggct gcaggaggct ctactggcga aatccaaaac    420
cgggtgaaca agagcgattg gtctaacttc gatgagacca atgactactc ttatggcact    480
aacaccactt tccaggattg gactaaggta accgtgtacg tgaatggtgt cctcgtctgg    540
ggaacagaac cgtcaggagc taccgcatcc ccttcagctt cagctactcc ttcgccatcc    600
agctcgccga caacaagtcc atcttcatct cccagtccaa gcagttcacc tacgccaaca    660
ccttcctcaa gttctccacc cccatccagc aatgatccta tattcaaag gtttctcacc    720 atgtacaaca agattcacga tccagccaac ggctacttct cacccaggg catacccta    780 cacagcgtcg aaactctcat cgtcgaggct cctgactacg gcacgaaaac tacatcggaa    840
gcctactcgt tttggctctg gctagaggct acctacggtg cggttaccgg caattggact    900
ccgttcaaca acgcgtggac gaccatggag acgtacatga ttccacaaca tgccgatcaa    960
ccgaacaatg cctcttataa cccgaacagt cctgcttcat atgcaccaga agaaccgctg   1020
ccatctatgt atcccgtcgc aatcgattct tcagtgccag ttggtcatga tccactcgca   1080
gcagagttgc aatctacata tggaaccccc gatatttatg ggatgcactg gttggccgac   1140
gtggacaaca tttatggcta tggcgactct ccaggaggcg gatgcgagct tggtccttca   1200
gcgaaaggcg tatcttatat caacaccttc agcgggggta gtcaagagag tgtctgggaa   1260
acagttacac agcctacgtg cgacaacgga agtacggtg gggctcatgg ttacgtcgat   1320
cttttcatcc agggatcaac accaccgcaa tggaaatata cggacgcacc cgatgctgac   1380
gcgcgggccg tgcaggcagc atactgggcg tacacctggg caagtgcgca aggcaaagct   1440
tccgcaatcg cccctacaat agccaaggct gctaaattgg gtgactatct tcgatactct   1500
ctcttcgata aatacttcaa acaggtgggc aactgttatc ctgccagttc gtgcccaggc   1560
gccaccggaa gacagtctga aacatacctg attggatggt attatgcttg gggtggaagt   1620
```

-continued

```
tctcagggct gggcttggcg catcggtgat ggcgctgctc attttggata ccaaaaccca    1680
cttgcggcct gggccatgtc aaacgtcact ccacttatcc cgctgtcccc caccgcaaag    1740
agcgactggg ccgcctctct ccagcgccaa ttggagttct accagtggct gcaatcagca    1800
gaaggtgcta ttgcgggcgg ggctaccaat tcctggaacg gcaactatgg cacacctcca    1860
gctggtgact ctacatttta cggcatggcg tacgattggg aacctgttta tcacgacccc    1920
ccttctaata attggttcgg cttttcaagca tggtccatgg agagagtcgc tgagtactac    1980
tacgttacag gcgacccaaa agccaaggcc ctgctagata agtgggttgc ttgggtcaag    2040
ccaaacgtaa ctacaggcgc atcatggtct atcccatcca atctgtcctg gtctggccaa    2100
ccagatacct ggaatccatc caacccgggg accaacgcga acctccatgt cactataacc    2160
tcttcgggac aagatgtcgg cgtggccgcg gctcttgcaa aaacgttgga gtactacgcc    2220
gcgaagtccg gagacaccgc gtccagagat ttggccaaag gcctcctcga tagcatttgg    2280
aacaatgatc aagacagctt gggagtaagc acgccagaga caaggactga ctattcccgc    2340
tttactcaag tttacgaccc gaccaccggc gatggcctct atattccttc tggctggaca    2400
ggtactatgc ccaacggcga ccaaatcaag ccaggcgcta catttctttc cattcgctcg    2460
tggtatacga aggaccctca atggtcaaag gttcaggcat atcttaacgg cggccctgca    2520
ccaaccttta attaccacag gttctgggcc gaatctgatt tcgccatggc taacgctgac    2580
ttcggtatgc tcttcccatc tggaagcccg tcaccaaccc cctcacctac tcctacatct    2640
tcgccctccc cgacgccttc gtcttcacca acaccctctc cctcccctc tcctaccggc    2700
gacacaactc cgcctagtgt gcccaccggg ctccaggtca ccggcaccac aacgtcatca    2760
gtcagcctgt cttggaccgc atctaccgac aacgttggtg tggctcatta caacgtttat    2820
aggaatggca ctttggtcgg acagccaacc gcgacatctt tcaccgacac tggtttggcg    2880
gcgggaaccct cttacactta tacagtagct gctgtggacg ctgcaggtaa tacctctgca    2940
caatctagcc cagtgaccgc cacaaccgcc tctccctccc cttcaccatc gccttctccc    3000
acacctactt catcaccatc ccccacacct agccctaccc cctctccaac atcaacatcg    3060
ggcgcatcgt gcaccgccac atacgtagtc aactccgatt ggggctccgg tttcaccaca    3120
actgttactg tgaccaacac tggcacccgt gcgacttccg gctggacggt tacgtggtcc    3180
ttcgctggca atcaaaccgt tacaaactac tggaataccg cactcacgca gtcgggcaag    3240
agtgtcacgg ccaaaaacct cagctataat aatgttatcc aaccagggca gtctacgacc    3300
ttcggattca acggttccta ttcggggaca aataccgctc ctacactcag ttgtactgcc    3360
tcctaa                                                               3366
```

<210> SEQ ID NO 3
<211> LENGTH: 2046
<212> TYPE: DNA
<213> ORGANISM: Artificial Sequence
<220> FEATURE:
<223> OTHER INFORMATION: Acidothermus cellulolyticus

<400> SEQUENCE: 3

```
atgcaccatg ctatgcggcg tatggtaaca tctgcctcag ttgtcggcgt cgctactctg      60
gcggccgcta ccgtcccttat cacaggagga atcgcccatg ccgcatctac tctaaagcag     120
ggagccgaag ctaatggaag atattttgga gtctcagctt ccgtgaatac ccttaacaat     180
agtgccgcag caaatcttgt cgcaacccaa ttcgacatgc ttaccccaga gaacgagatg     240
aaatgggata cagtggaaag ctccagaggt tcctttaatt tcgggccagg agatcaaatc     300
```

```
gttgcatttg ctacagccca taatatgcgc gttagagggc ataatctggt atggcattct    360
caacttccag gatgggtctc gtcacttcca ctgagccagg tgcagtctgc tatggagagt    420
catatcacag cagaggtcac gcactacaag ggcaaaatat acgcatggga cgttgtgaac    480
gagcctttg atgactctgg taaccttcgt acagatgttt ctaccaggc aatgggtgca      540
gggtacatcg ctgacgctct gcgaactgcg catgctgctg acccaaacgc aaagctctac    600
cttaacgact ataatattga gggtattaac gctaaaagtg acgctatgta caacctcatc    660
aaacaactta agtcacaggg agtccctatt gatggcgtag gattcgaaag ccacttcatt    720
gtgggccaag tgccctccac actccaacag aaatatgcagc gttttgctga tctcggagtc    780
gatgttgcca taacagaatt agatgacagg atgcctactc cgccttccca acaaaacctt    840
aatcaacagg ccaccgatga tgctaacgtg gtaaaagctt gcttggcggt tgctcgatgt    900
gtaggaatta cacagtggga tgtaagcgac gcagattctt gggttcctgg caccttctca    960
ggtcagggcg ccgcaactat gtttgatagc aatttacaac caaagcctgc tttcactgcc   1020
gtcttgaacg cgctttctgc atccgcctct gtatcacctt ctccgtcccc gtcaccctcc   1080
ccttctccaa gcccatctcc gtcaccatca ccttcaccta gcccatcacc atctccatca   1140
ccttccccctt cctcttctcc agtcagtggc ggtgttaaag ttcaatataa gaataacgat   1200
tccgctccgg gagacaacca gataaaacct ggcctgcaag tagttaatac tggatcgtca   1260
tcggttgatc tgagtacggt taccgttaga tactggttca cacgagacgg aggatcttcc   1320
acattggttt acaattgcga ctgggctgtt atgggttgtg gtaatattcg cgctagcttt   1380
ggatcagtta atccagcaac ccctacggct gatacgtatc tacaactctc cttcacagga   1440
ggcacactac ccgcaggagg atcaaccggt gagatacagt ccagggttaa caaaagcgac   1500
tggtcaaaact tcactgagac caatgactac agctatggta ctaacaccac cttccaagat   1560
tggtcaaagg tcactgtata cgttaatggt cgattggtct ggggcaccga accttccgga   1620
acatccccct ctccaacacc atctcctagt ccaaccccat ctccaagccc ttccccatct   1680
cccagtcctt caccttcgcc atcccctca ccatccccat ctccgtcttc ttctccgagt   1740
tcgggctgcg tggcatctat gagagttgat tctagctggc ctggcggttt tacagccact   1800
gttactgtgt ccaacactgg aggcgtctct acttcaggct ggcaagttgg ctggagctgg   1860
ccttcaggcg atagtttagt aaacgcgtgg aatgcagttg tttctgttac aggtaccagt   1920
gttagagctg tgaatgcaag ctataatgga gtgatccccg caggaggatc aaccactttc   1980
ggtttccagg cgaatggcac accaggcaca ccgacgttta cttgtactac ctcagcagat   2040
ctctaa                                                              2046
```

<210> SEQ ID NO 4
<211> LENGTH: 360
<212> TYPE: PRT
<213> ORGANISM: Artificial Sequence
<220> FEATURE:
<223> OTHER INFORMATION: Acidothermus cellulolyticus

<400> SEQUENCE: 4

Met Ala Gly Gly Gly Tyr Trp His Thr Ser Gly Arg Glu Ile Leu Asp
1               5                   10                  15

Ala Asn Asn Val Pro Val Arg Ile Ala Gly Ile Asn Trp Phe Gly Phe
            20                  25                  30

Glu Thr Cys Asn Tyr Val Val His Gly Leu Trp Ser Arg Asp Tyr Arg
        35                  40                  45

```
Ser Met Leu Asp Gln Ile Lys Ser Leu Gly Tyr Asn Thr Ile Arg Leu
     50                  55                  60

Pro Tyr Ser Asp Asp Ile Leu Lys Pro Gly Thr Met Pro Asn Ser Ile
 65                  70                  75                  80

Asn Phe Tyr Gln Met Asn Gln Asp Leu Gln Gly Leu Thr Ser Leu Gln
                     85                  90                  95

Val Met Asp Lys Ile Val Ala Tyr Ala Gly Gln Ile Gly Leu Arg Ile
                100                 105                 110

Ile Leu Asp Arg His Arg Pro Asp Cys Ser Gly Gln Ser Ala Leu Trp
            115                 120                 125

Tyr Thr Ser Ser Val Ser Glu Ala Thr Trp Ile Ser Asp Leu Gln Ala
130                 135                 140

Leu Ala Gln Arg Tyr Lys Gly Asn Pro Thr Val Val Gly Phe Asp Leu
145                 150                 155                 160

His Asn Glu Pro His Asp Pro Ala Cys Trp Gly Cys Gly Asp Pro Ser
                165                 170                 175

Ile Asp Trp Arg Leu Ala Ala Glu Arg Ala Gly Asn Ala Val Leu Ser
            180                 185                 190

Val Asn Pro Asn Leu Leu Ile Phe Val Glu Gly Val Gln Ser Tyr Asn
        195                 200                 205

Gly Asp Ser Tyr Trp Trp Gly Gly Asn Leu Gln Gly Ala Gly Gln Tyr
    210                 215                 220

Pro Val Val Leu Asn Val Pro Asn Arg Leu Val Tyr Ser Ala His Asp
225                 230                 235                 240

Tyr Ala Thr Ser Val Tyr Pro Gln Thr Trp Phe Ser Asp Pro Thr Phe
                245                 250                 255

Pro Asn Asn Met Pro Gly Ile Trp Asn Lys Asn Trp Gly Tyr Leu Phe
            260                 265                 270

Asn Gln Asn Ile Ala Pro Val Trp Leu Gly Glu Phe Gly Thr Thr Leu
        275                 280                 285

Gln Ser Thr Thr Asp Gln Thr Trp Leu Lys Thr Leu Val Gln Tyr Leu
    290                 295                 300

Arg Pro Thr Ala Gln Tyr Gly Ala Asp Ser Phe Gln Trp Thr Phe Trp
305                 310                 315                 320

Ser Trp Asn Pro Asp Ser Gly Asp Thr Gly Gly Ile Leu Lys Asp Asp
                325                 330                 335

Trp Gln Thr Val Asp Thr Val Lys Asp Gly Tyr Leu Ala Pro Ile Lys
            340                 345                 350

Ser Ser Ile Phe Asp Pro Val Gly
        355                 360

<210> SEQ ID NO 5
<211> LENGTH: 1120
<212> TYPE: PRT
<213> ORGANISM: Artificial Sequence
<220> FEATURE:
<223> OTHER INFORMATION: Acidothermus celluloyticus

<400> SEQUENCE: 5

Met Gly Leu Arg Arg Arg Leu Arg Ala Gly Ile Val Ser Ala Ala Ala
 1               5                  10                  15

Leu Gly Ser Leu Val Ser Gly Leu Val Ala Val Ala Pro Val Ala His
                20                  25                  30

Ala Ala Val Thr Leu Lys Ala Gln Tyr Lys Asn Asn Asp Ser Ala Pro
            35                  40                  45
```

```
Ser Asp Asn Gln Ile Lys Pro Gly Leu Gln Leu Val Asn Thr Gly Ser
 50                  55                  60

Ser Ser Val Asp Leu Ser Thr Val Thr Val Arg Tyr Trp Phe Thr Arg
 65                  70                  75                  80

Asp Gly Gly Ser Ser Thr Leu Val Tyr Asn Cys Asp Trp Ala Ala Met
                 85                  90                  95

Gly Cys Gly Asn Ile Arg Ala Ser Phe Gly Ser Val Asn Pro Ala Thr
                100                 105                 110

Pro Thr Ala Asp Thr Tyr Leu Gln Leu Ser Phe Thr Gly Gly Thr Leu
            115                 120                 125

Ala Ala Gly Gly Ser Thr Gly Glu Ile Gln Asn Arg Val Asn Lys Ser
        130                 135                 140

Asp Trp Ser Asn Phe Asp Glu Thr Asn Asp Tyr Ser Tyr Gly Thr Asn
145                 150                 155                 160

Thr Thr Phe Gln Asp Trp Thr Lys Val Thr Val Tyr Val Asn Gly Val
                165                 170                 175

Leu Val Trp Gly Thr Glu Pro Ser Gly Ala Thr Ala Ser Pro Ser Ala
            180                 185                 190

Ser Ala Thr Pro Ser Pro Ser Ser Pro Thr Thr Ser Pro Ser Ser
        195                 200                 205

Ser Pro Ser Pro Ser Ser Pro Thr Pro Thr Pro Ser Ser Ser Ser
    210                 215                 220

Pro Pro Pro Ser Ser Asn Asp Pro Tyr Ile Gln Arg Phe Leu Thr Met
225                 230                 235                 240

Tyr Asn Lys Ile His Asp Pro Ala Asn Gly Tyr Phe Ser Pro Gln Gly
                245                 250                 255

Ile Pro Tyr His Ser Val Glu Thr Leu Ile Val Glu Ala Pro Asp Tyr
            260                 265                 270

Gly His Glu Thr Thr Ser Glu Ala Tyr Ser Phe Trp Leu Trp Leu Glu
        275                 280                 285

Ala Thr Tyr Gly Ala Val Thr Gly Asn Trp Thr Pro Phe Asn Asn Ala
        290                 295                 300

Trp Thr Thr Met Glu Thr Tyr Met Ile Pro Gln His Ala Asp Gln Pro
305                 310                 315                 320

Asn Asn Ala Ser Tyr Asn Pro Asn Ser Pro Ala Ser Tyr Ala Pro Glu
                325                 330                 335

Glu Pro Leu Pro Ser Met Tyr Pro Val Ala Ile Asp Ser Ser Val Pro
            340                 345                 350

Val Gly His Asp Pro Leu Ala Ala Glu Leu Gln Ser Thr Tyr Gly Thr
        355                 360                 365

Pro Asp Ile Tyr Gly Met His Trp Leu Ala Asp Val Asp Asn Ile Tyr
370                 375                 380

Gly Tyr Gly Asp Ser Pro Gly Gly Cys Glu Leu Gly Pro Ser Ala
385                 390                 395                 400

Lys Gly Val Ser Tyr Ile Asn Thr Phe Gln Arg Gly Ser Gln Glu Ser
                405                 410                 415

Val Trp Glu Thr Val Thr Gln Pro Thr Cys Asp Asn Gly Lys Tyr Gly
            420                 425                 430

Gly Ala His Gly Tyr Val Asp Leu Phe Ile Gln Gly Ser Thr Pro Pro
        435                 440                 445

Gln Trp Lys Tyr Thr Asp Ala Pro Asp Ala Asp Ala Arg Ala Val Gln
    450                 455                 460

Ala Ala Tyr Trp Ala Tyr Thr Trp Ala Ser Ala Gln Gly Lys Ala Ser
465                 470                 475                 480
```

```
Ala Ile Ala Pro Thr Ile Ala Lys Ala Ala Lys Leu Gly Asp Tyr Leu
                485                 490                 495

Arg Tyr Ser Leu Phe Asp Lys Tyr Phe Lys Gln Val Gly Asn Cys Tyr
            500                 505                 510

Pro Ala Ser Ser Cys Pro Gly Ala Thr Gly Arg Gln Ser Glu Thr Tyr
        515                 520                 525

Leu Ile Gly Trp Tyr Tyr Ala Trp Gly Gly Ser Ser Gln Gly Trp Ala
    530                 535                 540

Trp Arg Ile Gly Asp Gly Ala Ala His Phe Gly Tyr Gln Asn Pro Leu
545                 550                 555                 560

Ala Ala Trp Ala Met Ser Asn Val Thr Pro Leu Ile Pro Leu Ser Pro
                565                 570                 575

Thr Ala Lys Ser Asp Trp Ala Ala Ser Leu Gln Arg Gln Leu Glu Phe
            580                 585                 590

Tyr Gln Trp Leu Gln Ser Ala Glu Gly Ala Ile Ala Gly Gly Ala Thr
        595                 600                 605

Asn Ser Trp Asn Gly Asn Tyr Gly Thr Pro Pro Ala Gly Asp Ser Thr
    610                 615                 620

Phe Tyr Gly Met Ala Tyr Asp Trp Glu Pro Val Tyr His Asp Pro Pro
625                 630                 635                 640

Ser Asn Asn Trp Phe Gly Phe Gln Ala Trp Ser Met Glu Arg Val Ala
                645                 650                 655

Glu Tyr Tyr Val Thr Gly Asp Pro Lys Ala Lys Ala Leu Leu Asp
            660                 665                 670

Lys Trp Val Ala Trp Val Lys Pro Asn Val Thr Thr Gly Ala Ser Trp
        675                 680                 685

Ser Ile Pro Ser Asn Leu Ser Trp Ser Gly Gln Pro Asp Thr Trp Asn
    690                 695                 700

Pro Ser Asn Pro Gly Thr Asn Ala Asn Leu His Val Thr Ile Thr Ser
705                 710                 715                 720

Ser Gly Gln Asp Val Gly Val Ala Ala Leu Ala Lys Thr Leu Glu
                725                 730                 735

Tyr Tyr Ala Ala Lys Ser Gly Asp Thr Ala Ser Arg Asp Leu Ala Lys
            740                 745                 750

Gly Leu Leu Asp Ser Ile Trp Asn Asn Asp Gln Asp Ser Leu Gly Val
        755                 760                 765

Ser Thr Pro Glu Thr Arg Thr Asp Tyr Ser Arg Phe Thr Gln Val Tyr
    770                 775                 780

Asp Pro Thr Thr Gly Asp Gly Leu Tyr Ile Pro Ser Gly Trp Thr Gly
785                 790                 795                 800

Thr Met Pro Asn Gly Asp Gln Ile Lys Pro Gly Ala Thr Phe Leu Ser
                805                 810                 815

Ile Arg Ser Trp Tyr Thr Lys Asp Pro Gln Trp Ser Lys Val Gln Ala
            820                 825                 830

Tyr Leu Asn Gly Gly Pro Ala Pro Thr Phe Asn Tyr His Arg Phe Trp
        835                 840                 845

Ala Glu Ser Asp Phe Ala Met Ala Asn Ala Asp Phe Gly Met Leu Phe
    850                 855                 860

Pro Ser Gly Ser Pro Ser Pro Thr Pro Ser Pro Thr Pro Thr Ser Ser
865                 870                 875                 880

Pro Ser Pro Thr Pro Ser Ser Ser Pro Thr Pro Ser Pro Ser Pro Ser
                885                 890                 895

Pro Thr Gly Asp Thr Thr Pro Pro Ser Val Pro Thr Gly Leu Gln Val
            900                 905                 910
```

```
Thr Gly Thr Thr Thr Ser Ser Val Ser Leu Ser Trp Thr Ala Ser Thr
        915                 920                 925

Asp Asn Val Gly Val Ala His Tyr Asn Val Tyr Arg Asn Gly Thr Leu
    930                 935                 940

Val Gly Gln Pro Thr Ala Thr Ser Phe Thr Asp Thr Gly Leu Ala Ala
945                 950                 955                 960

Gly Thr Ser Tyr Thr Tyr Thr Val Ala Val Asp Ala Ala Gly Asn
        965                 970                 975

Thr Ser Ala Gln Ser Ser Pro Val Thr Ala Thr Thr Ala Ser Pro Ser
        980                 985                 990

Pro Ser Pro Ser Pro Ser Pro Thr Pro Thr Ser Ser Pro Ser Pro Thr
        995                1000                1005

Pro Ser Pro Thr Pro Ser Pro Thr Ser Thr Ser Gly Ala Ser Cys
       1010                1015                1020

Thr Ala Thr Tyr Val Val Asn Ser Asp Trp Gly Ser Gly Phe Thr
       1025                1030                1035

Thr Thr Val Thr Val Thr Asn Thr Gly Thr Arg Ala Thr Ser Gly
       1040                1045                1050

Trp Thr Val Thr Trp Ser Phe Ala Gly Asn Gln Thr Val Thr Asn
       1055                1060                1065

Tyr Trp Asn Thr Ala Leu Thr Gln Ser Gly Lys Ser Val Thr Ala
       1070                1075                1080

Lys Asn Leu Ser Tyr Asn Asn Val Ile Gln Pro Gly Gln Ser Thr
       1085                1090                1095

Thr Phe Gly Phe Asn Gly Ser Tyr Ser Gly Thr Asn Thr Ala Pro
       1100                1105                1110

Thr Leu Ser Cys Thr Ala Ser
       1115                1120

<210> SEQ ID NO 6
<211> LENGTH: 678
<212> TYPE: PRT
<213> ORGANISM: Artificial Sequence
<220> FEATURE:
<223> OTHER INFORMATION: Acidothermus cellulolyticus

<400> SEQUENCE: 6

Met His His Ala Met Arg Arg Met Val Thr Ser Ala Ser Val Val Gly
1               5                   10                  15

Val Ala Thr Leu Ala Ala Ala Thr Val Leu Ile Thr Gly Gly Ile Ala
            20                  25                  30

His Ala Ala Ser Thr Leu Lys Gln Gly Ala Glu Ala Asn Gly Arg Tyr
        35                  40                  45

Phe Gly Val Ser Ala Ser Val Asn Thr Leu Asn Asn Ser Ala Ala Ala
    50                  55                  60

Asn Leu Val Ala Thr Gln Phe Asp Met Leu Thr Pro Glu Asn Glu Met
65                  70                  75                  80

Lys Trp Asp Thr Val Glu Ser Ser Arg Gly Ser Phe Asn Phe Gly Pro
                85                  90                  95

Gly Asp Gln Ile Val Ala Phe Ala Thr Ala His Asn Met Arg Val Arg
            100                 105                 110

Gly His Asn Leu Val Trp His Ser Gln Leu Pro Gly Trp Val Ser Ser
        115                 120                 125

Leu Pro Leu Ser Gln Val Gln Ser Ala Met Glu Ser His Ile Thr Ala
    130                 135                 140
```

-continued

```
Glu Val Thr His Tyr Lys Gly Lys Ile Tyr Ala Trp Asp Val Val Asn
145                 150                 155                 160

Glu Pro Phe Asp Asp Ser Gly Asn Leu Arg Thr Asp Val Phe Tyr Gln
            165                 170                 175

Ala Met Gly Ala Gly Tyr Ile Ala Asp Ala Leu Arg Thr Ala His Ala
        180                 185                 190

Ala Asp Pro Asn Ala Lys Leu Tyr Leu Asn Asp Tyr Asn Ile Glu Gly
    195                 200                 205

Ile Asn Ala Lys Ser Asp Ala Met Tyr Asn Leu Ile Lys Gln Leu Lys
210                 215                 220

Ser Gln Gly Val Pro Ile Asp Gly Val Gly Phe Glu Ser His Phe Ile
225                 230                 235                 240

Val Gly Gln Val Pro Ser Thr Leu Gln Gln Asn Met Gln Arg Phe Ala
            245                 250                 255

Asp Leu Gly Val Asp Val Ala Ile Thr Glu Leu Asp Asp Arg Met Pro
        260                 265                 270

Thr Pro Pro Ser Gln Gln Asn Leu Asn Gln Gln Ala Thr Asp Asp Ala
    275                 280                 285

Asn Val Val Lys Ala Cys Leu Ala Val Ala Arg Cys Val Gly Ile Thr
290                 295                 300

Gln Trp Asp Val Ser Asp Ala Asp Ser Trp Val Pro Gly Thr Phe Ser
305                 310                 315                 320

Gly Gln Gly Ala Ala Thr Met Phe Asp Ser Asn Leu Gln Pro Lys Pro
            325                 330                 335

Ala Phe Thr Ala Val Leu Asn Ala Leu Ser Ala Ser Ala Ser Val Ser
        340                 345                 350

Pro Ser Pro Ser Pro Ser Pro Ser Pro Ser Pro Ser Pro Ser Pro Ser
    355                 360                 365

Pro Ser Pro Ser Pro Ser Pro Ser Pro Ser Pro Ser Pro Ser Pro Ser
370                 375                 380

Ser Ser Pro Val Ser Gly Gly Val Lys Val Gln Tyr Lys Asn Asn Asp
385                 390                 395                 400

Ser Ala Pro Gly Asp Asn Gln Ile Lys Pro Gly Leu Gln Val Val Asn
            405                 410                 415

Thr Gly Ser Ser Ser Val Asp Leu Ser Thr Val Thr Val Arg Tyr Trp
        420                 425                 430

Phe Thr Arg Asp Gly Gly Ser Ser Thr Leu Val Tyr Asn Cys Asp Trp
    435                 440                 445

Ala Val Met Gly Cys Gly Asn Ile Arg Ala Ser Phe Gly Ser Val Asn
450                 455                 460

Pro Ala Thr Pro Thr Ala Asp Thr Tyr Leu Gln Leu Ser Phe Thr Gly
465                 470                 475                 480

Gly Thr Leu Pro Ala Gly Gly Ser Thr Gly Glu Ile Gln Ser Arg Val
            485                 490                 495

Asn Lys Ser Asp Trp Ser Asn Phe Thr Glu Thr Asn Asp Tyr Ser Tyr
        500                 505                 510

Gly Thr Asn Thr Thr Phe Gln Asp Trp Ser Lys Val Thr Val Tyr Val
    515                 520                 525

Asn Gly Arg Leu Val Trp Gly Thr Glu Pro Ser Gly Thr Ser Pro Ser
530                 535                 540

Pro Thr Pro Ser Pro Ser Pro Thr Ser Pro Ser Pro Ser Pro Ser Ser
545                 550                 555                 560

Pro Ser Pro Ser Pro Ser Pro Ser Pro Ser Pro Ser Pro Ser Pro Ser
            565                 570                 575
```

```
Ser Ser Pro Ser Ser Gly Cys Val Ala Ser Met Arg Val Asp Ser Ser
            580                 585                 590

Trp Pro Gly Gly Phe Thr Ala Thr Val Thr Val Ser Asn Thr Gly Gly
        595                 600                 605

Val Ser Thr Ser Gly Trp Gln Val Gly Trp Ser Trp Pro Ser Gly Asp
        610             615                 620

Ser Leu Val Asn Ala Trp Asn Ala Val Val Ser Val Thr Gly Thr Ser
625                 630                 635                 640

Val Arg Ala Val Asn Ala Ser Tyr Asn Gly Val Ile Pro Ala Gly Gly
                645                 650                 655

Ser Thr Thr Phe Gly Phe Gln Ala Asn Gly Thr Pro Gly Thr Pro Thr
            660                 665                 670

Phe Thr Cys Thr Thr Ser
            675
```